(12) United States Patent
Aharoni et al.

(10) Patent No.: US 8,133,273 B2
(45) Date of Patent: Mar. 13, 2012

(54) INJECTABLE INTRAOCULAR IMPLANTS

(75) Inventors: Eli Aharoni, Tel Aviv (IL); Yossi Gross, Moshav Mazor (IL); Gideon Dotan, Yehud (IL); Iden Eisenberg, Ness-Ziona (IL)

(73) Assignee: Visioncare Ophthalmic Technologies Inc., Saratoga, CA (US)

( * ) Notice: Subject to any disclaimer, the term of this patent is extended or adjusted under 35 U.S.C. 154(b) by 763 days.

(21) Appl. No.: 11/996,707

(22) PCT Filed: Jul. 27, 2006

(86) PCT No.: PCT/IL2006/000873
§ 371 (c)(1),
(2), (4) Date: Aug. 11, 2008

(87) PCT Pub. No.: WO2007/013080
PCT Pub. Date: Feb. 1, 2007

(65) Prior Publication Data
US 2009/0036982 A1    Feb. 5, 2009

Related U.S. Application Data

(63) Continuation of application No. 11/193,781, filed on Jul. 28, 2005.

(51) Int. Cl.
*A61F 2/16* (2006.01)
*A61F 9/00* (2006.01)
(52) U.S. Cl. ................... 623/6.12; 606/107
(58) Field of Classification Search .......... 623/6.12; 606/107
See application file for complete search history.

(56) References Cited

U.S. PATENT DOCUMENTS

| | | | |
|---|---|---|---|
| 3,515,461 | A | 6/1970 | Rayces et al. |
| 4,074,368 | A | 2/1978 | Levy, Jr. et al. |
| 4,172,297 | A | 10/1979 | Schlegel et al. |
| 4,373,218 | A | 2/1983 | Schachar |
| 4,527,294 | A | 7/1985 | Heslin |
| 4,581,031 | A | 4/1986 | Koziol et al. |
| 4,666,446 | A | 5/1987 | Koziol et al. |
| 4,687,484 | A | 8/1987 | Kaplan |
| 4,759,761 | A | 7/1988 | Portnoy |
| 4,816,030 | A | 3/1989 | Robinson |
| 4,833,890 | A | 5/1989 | Kelman |
| 4,892,543 | A | 1/1990 | Turley |
| 4,911,714 | A | 3/1990 | Poley |
| 4,911,715 | A | 3/1990 | Kelman |
| 4,968,127 | A | 11/1990 | Russell et al. |

(Continued)

FOREIGN PATENT DOCUMENTS

DE        3428895        2/1986
(Continued)

OTHER PUBLICATIONS

An Office Action dated Aug. 29, 2009, which issued during the prosecution of Applicant's Canadian Patent Application No. 2,455,076.

(Continued)

*Primary Examiner* — David Isabella
*Assistant Examiner* — Leslie Coburn
(74) *Attorney, Agent, or Firm* — Fish & Richardson P.C.

(57) ABSTRACT

An injectable intraocular implant including an optics portion and a resilient, flexible haptics portion mounted coaxially with the optics portion and a method for inserting the implant into the eye.

18 Claims, 40 Drawing Sheets

U.S. PATENT DOCUMENTS

| | | | |
|---|---|---|---|
| 4,976,732 | A | 12/1990 | Vorosmarthy |
| 4,994,082 | A | 2/1991 | Richards et al. |
| 5,044,743 | A | 9/1991 | Ting |
| 5,108,429 | A | 4/1992 | Wiley |
| 5,190,552 | A * | 3/1993 | Kelman ............ 606/107 |
| 5,222,981 | A | 6/1993 | Werblin |
| 5,275,604 | A * | 1/1994 | Rheinish et al. ........ 606/107 |
| 5,354,335 | A | 10/1994 | Lipshitz et al. |
| 5,384,606 | A | 1/1995 | Koch et al. |
| 5,391,202 | A | 2/1995 | Lipshitz et al. |
| 5,616,148 | A * | 4/1997 | Eagles et al. ............ 606/107 |
| 5,628,798 | A | 5/1997 | Eggleston et al. |
| 5,653,751 | A | 8/1997 | Samiy et al. |
| 5,769,889 | A | 6/1998 | Kelman |
| 5,769,890 | A | 6/1998 | McDonald |
| 5,814,103 | A | 9/1998 | Lipshitz et al. |
| 5,876,442 | A | 3/1999 | Lipshitz et al. |
| 5,928,283 | A | 7/1999 | Gross et al. |
| 5,964,802 | A | 10/1999 | Anello et al. |
| 6,007,579 | A | 12/1999 | Lipshitz et al. |
| 6,066,171 | A | 5/2000 | Lipshitz et al. |
| 6,197,057 | B1 | 3/2001 | Peyman et al. |
| 6,358,280 | B1 | 3/2002 | Herrick |
| 6,400,989 | B1 | 6/2002 | Eckmiller |
| 6,464,725 | B2 | 10/2002 | Skotton |
| 6,569,199 | B1 | 5/2003 | Dotan et al. |
| 6,596,026 | B1 | 7/2003 | Gross et al. |
| 6,847,847 | B2 | 1/2005 | Nisch et al. |
| 6,902,577 | B2 | 6/2005 | Lipshitz et al. |
| 6,913,620 | B2 | 7/2005 | Lipshitz et al. |
| 6,972,032 | B2 | 12/2005 | Aharoni et al. |
| 7,001,427 | B2 | 2/2006 | Aharoni et al. |
| 7,008,448 | B2 | 3/2006 | Lipshitz et al. |
| 7,079,900 | B2 | 7/2006 | Greenburg et al. |
| 7,276,080 | B2 | 10/2007 | Murakami et al. |
| 2001/0018612 | A1 | 8/2001 | Carson et al. |
| 2002/0143395 | A1 | 10/2002 | Skottun |
| 2003/0109926 | A1 | 6/2003 | Portney |
| 2003/0187502 | A1 | 10/2003 | Lipshitz |
| 2003/0187503 | A1 | 10/2003 | Lipshitz et al. |
| 2004/0181279 | A1 | 9/2004 | Nun |
| 2005/0125000 | A1 | 6/2005 | Tourrette et al. |

FOREIGN PATENT DOCUMENTS

| | | |
|---|---|---|
| DE | 4403326 | 6/1995 |
| DE | 19501444 | 7/1996 |
| EP | 0162573 | 11/1985 |
| EP | 0212616 | 3/1987 |
| EP | 0419740 | 4/1991 |
| EP | 0897702 | 2/1999 |
| EP | 1092402 | 4/2001 |
| EP | 1475055 | 11/2004 |
| FR | 2666735 | 3/1992 |
| GB | 1303579 | 1/1973 |
| GB | 2181355 | 4/1987 |
| JP | 2005515807 | 6/2005 |
| WO | 8301566 | 5/1983 |
| WO | 9407435 | 4/1994 |
| WO | WO-0004849 | 2/2000 |
| WO | 0038593 | 7/2000 |

OTHER PUBLICATIONS

An Office Action dated Sep. 8, 2009, which issued during the prosecution of Applicant's Japanese Patent Application No. 2004-560169.

An Office Action dated Sep. 9, 2009, which issued during the prosecution of Applicant's U.S. Appl. No. 11/069,581.

Gray, Henry. "The Tunics of the Eye." http://www.bartleby.com., (2008).

An English Translation of first Office Action dated Apr. 19, 2011, which issued during the prosecution of Japanese Patent Application No. 2008-523540.

* cited by examiner

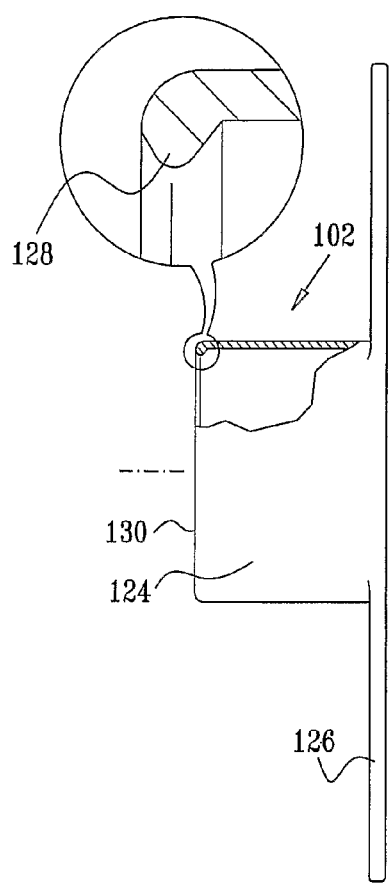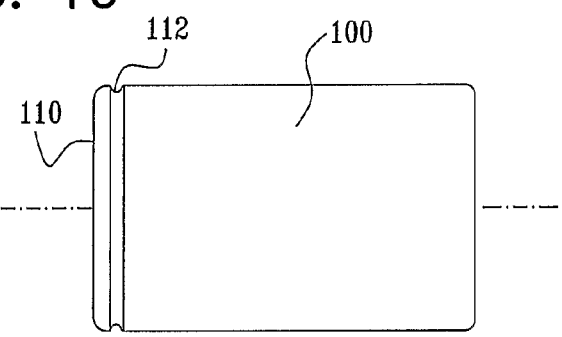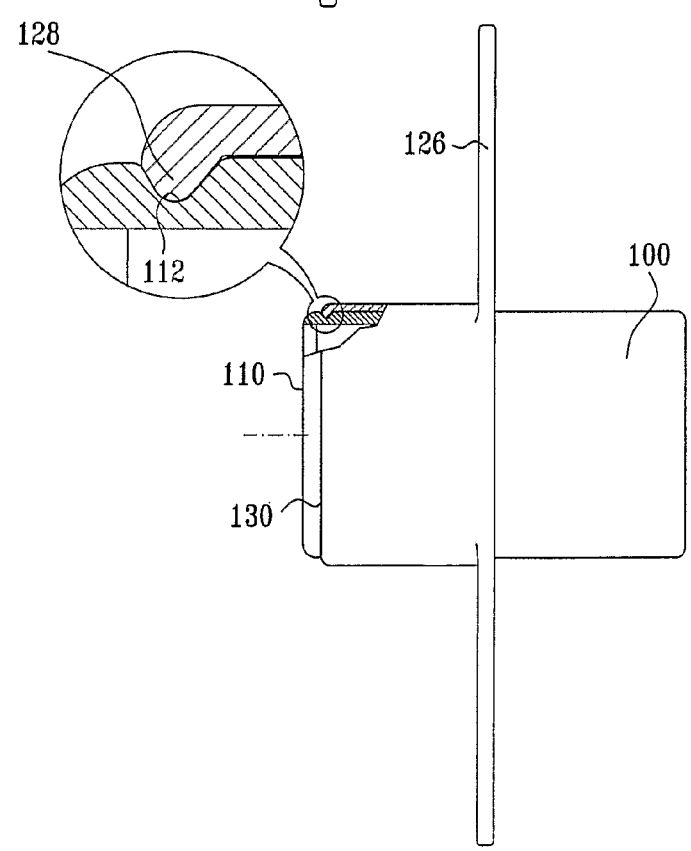
FIG. 1C
FIG. 1D

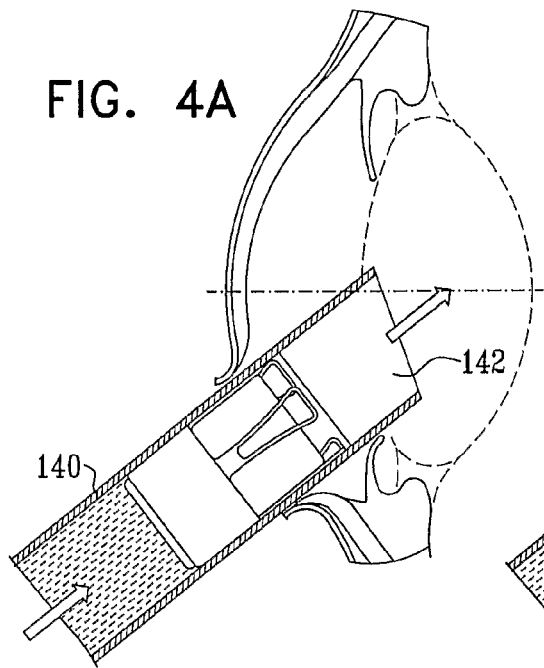
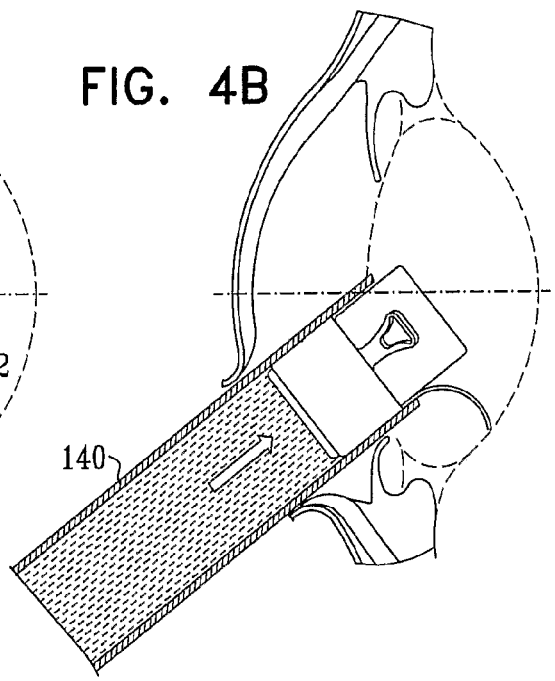
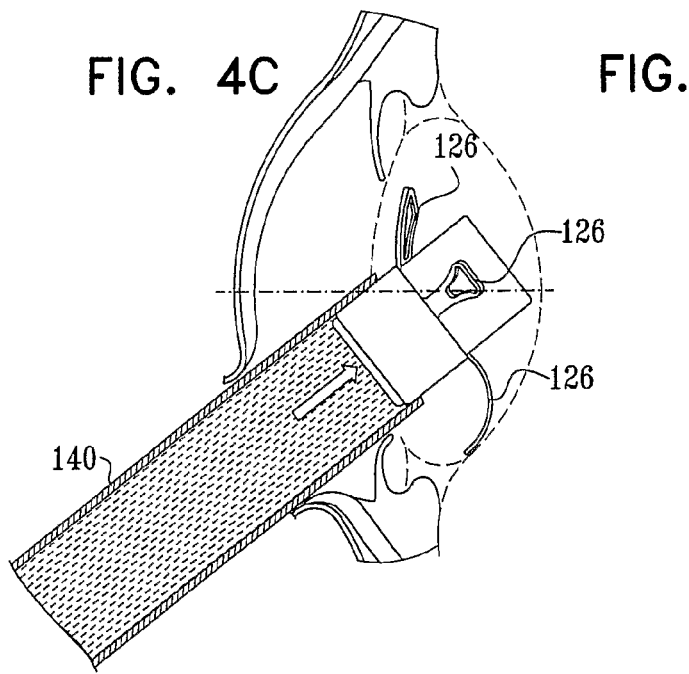
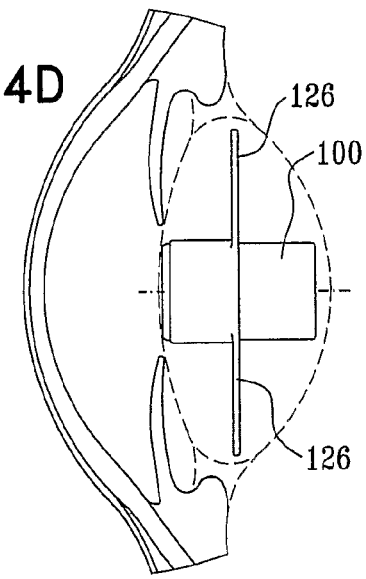

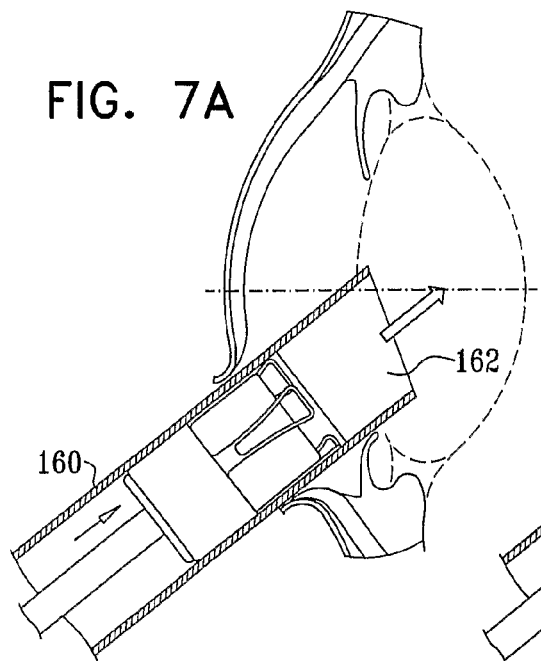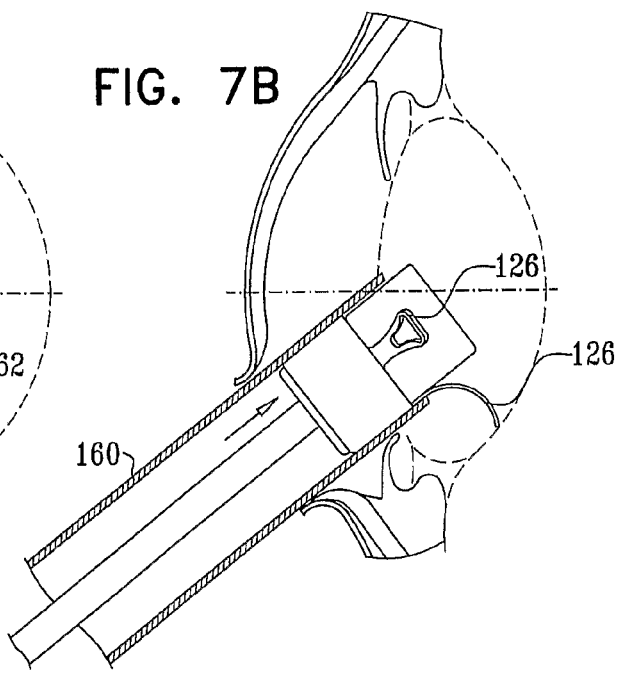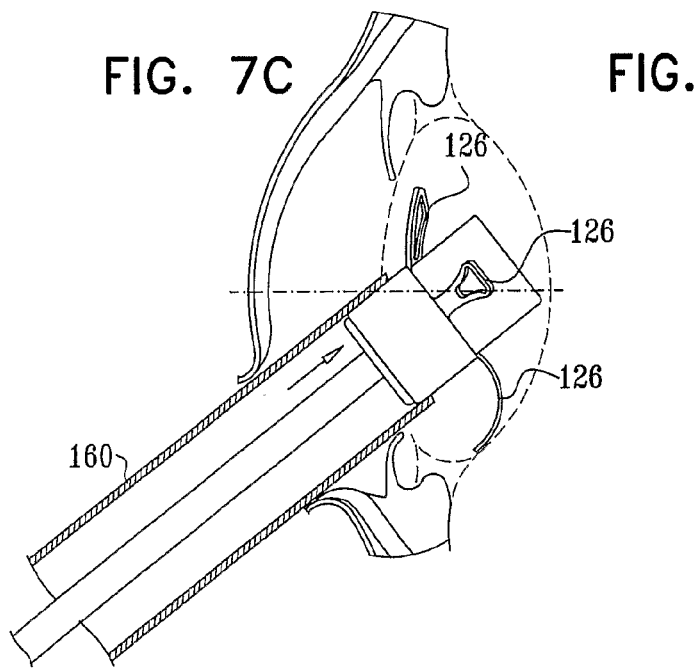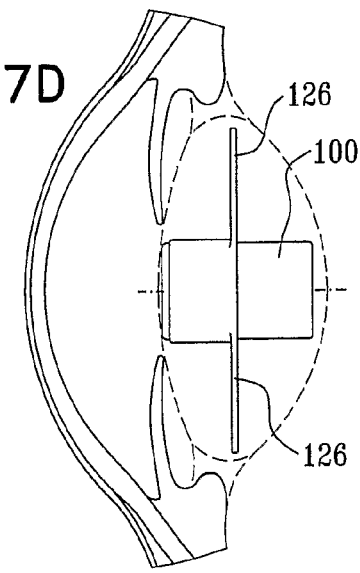

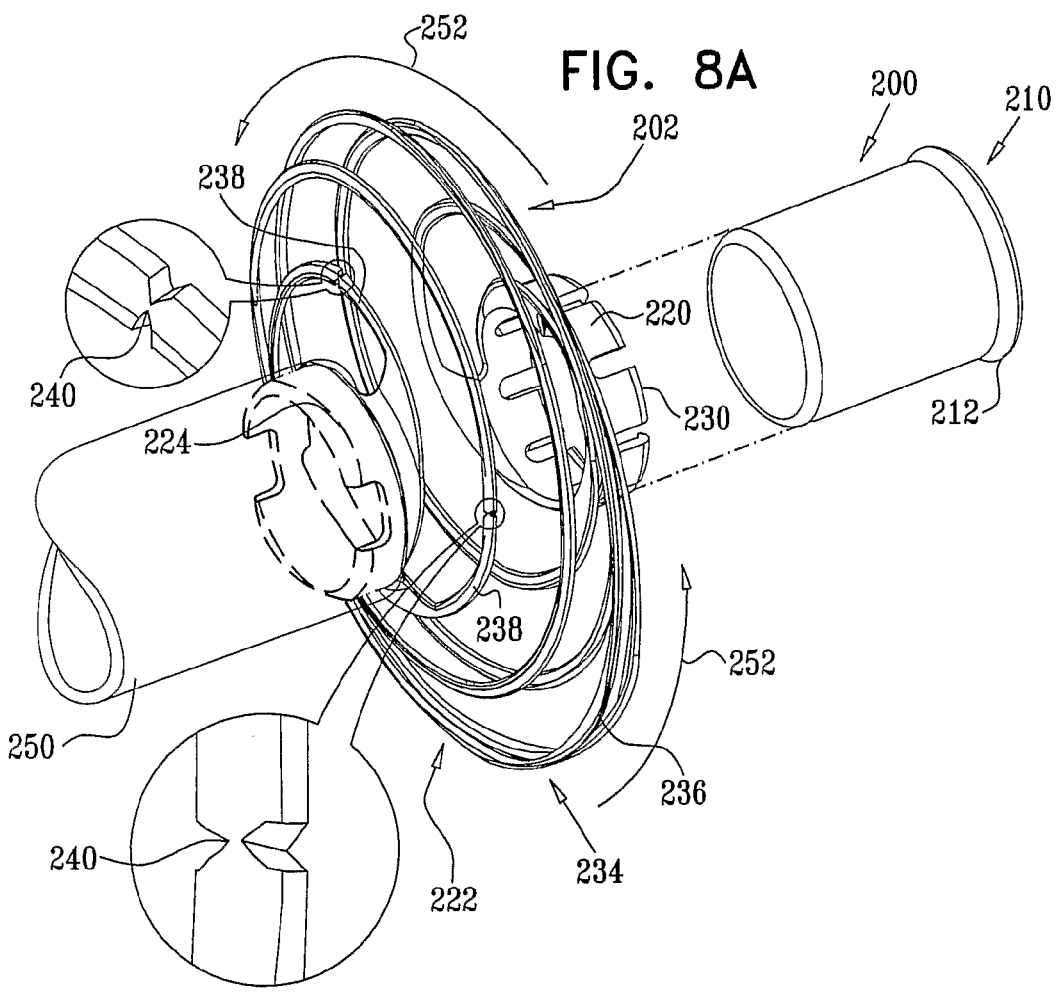
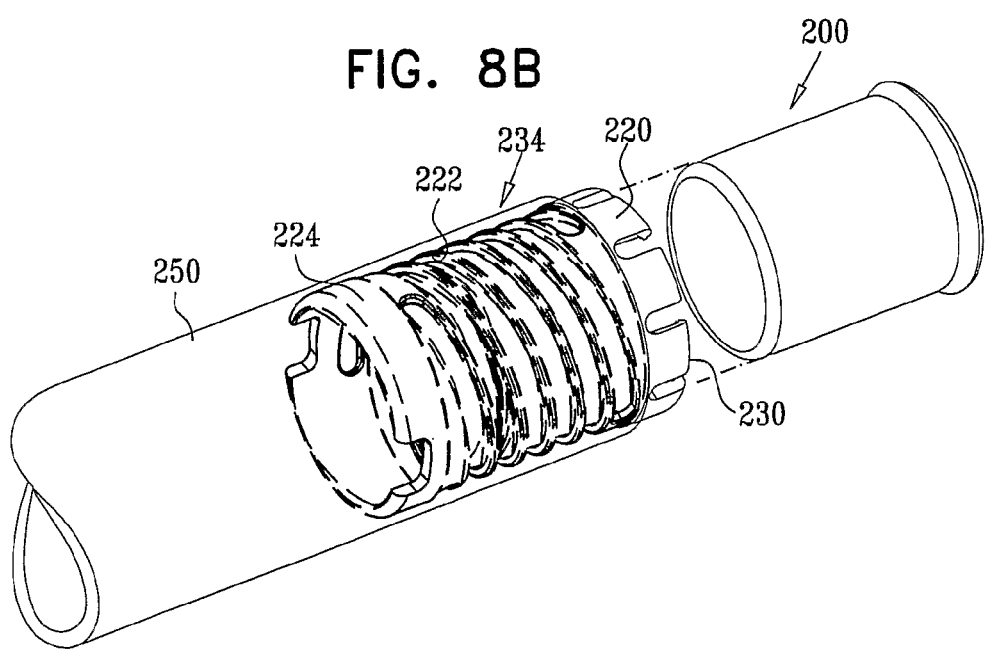

TO VACUUM PUMP

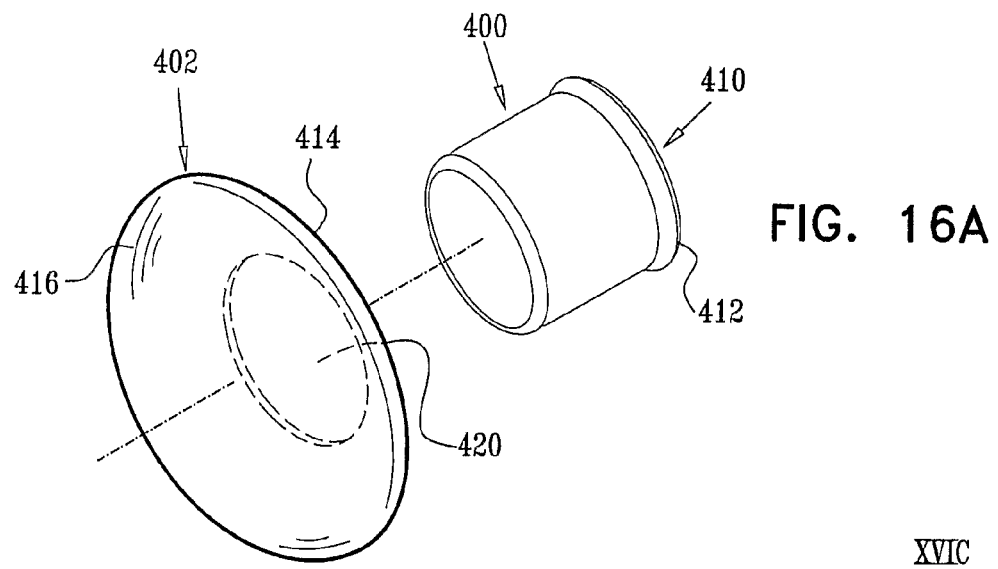
FIG. 16A
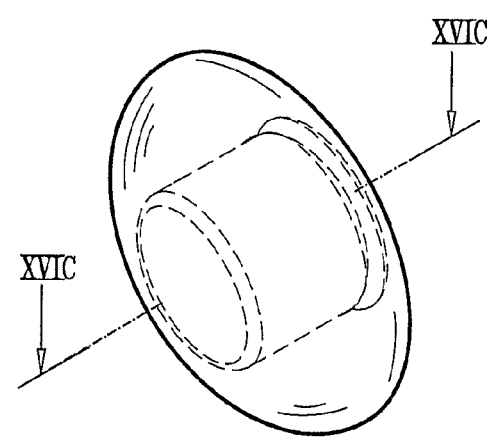
FIG. 16B
FIG. 16C
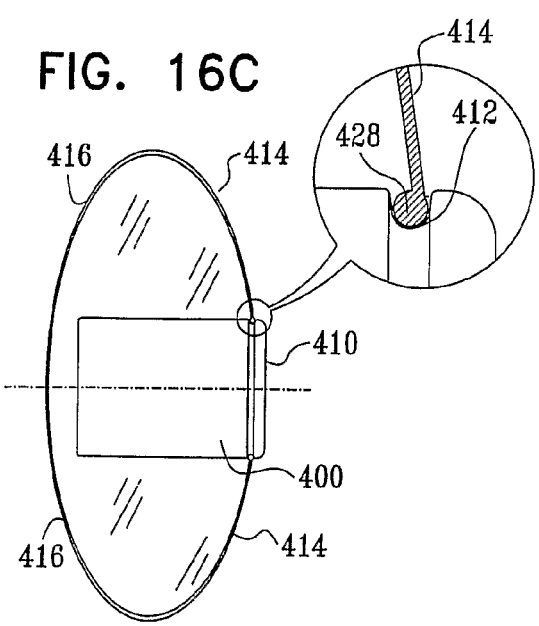

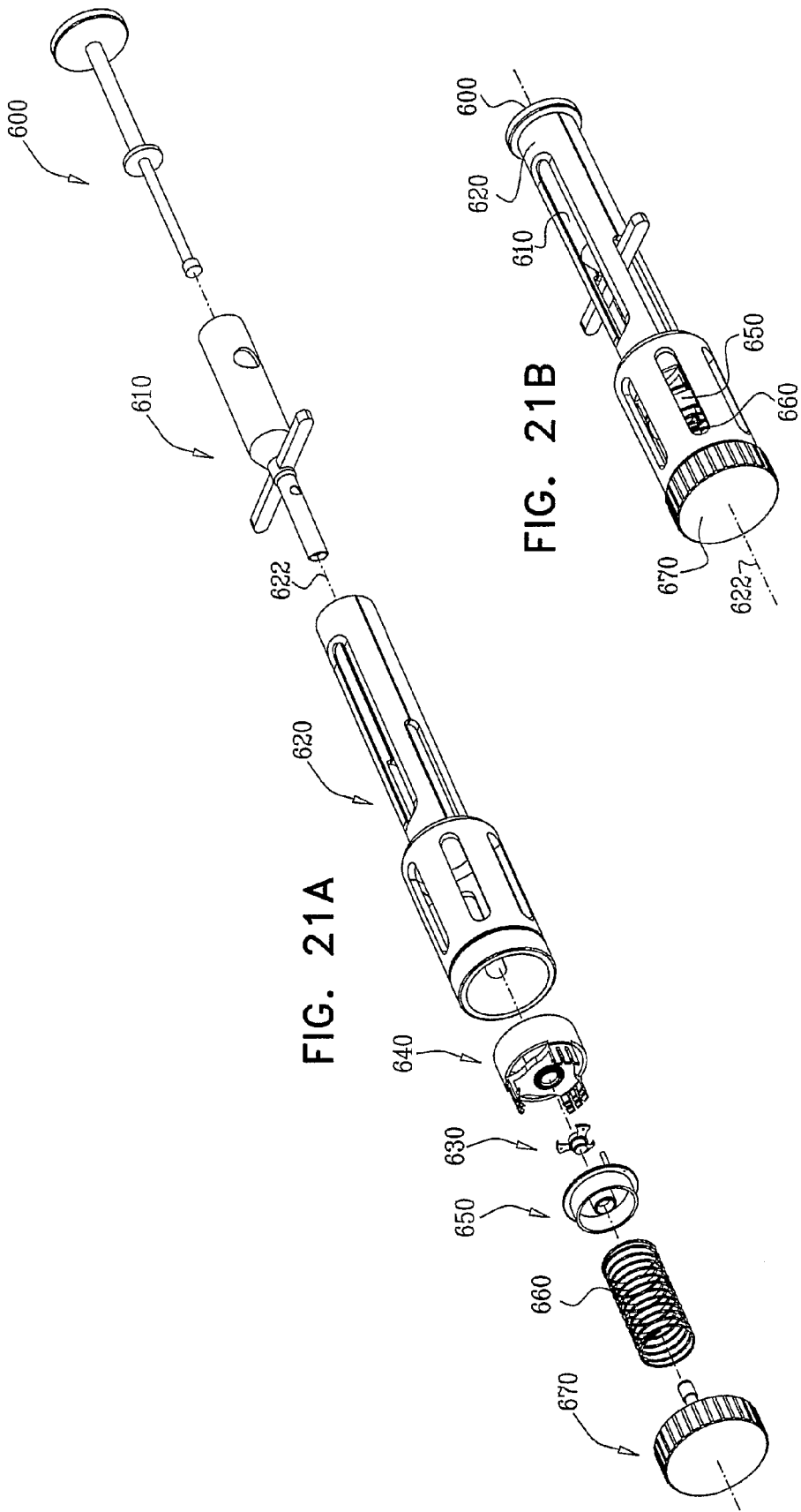

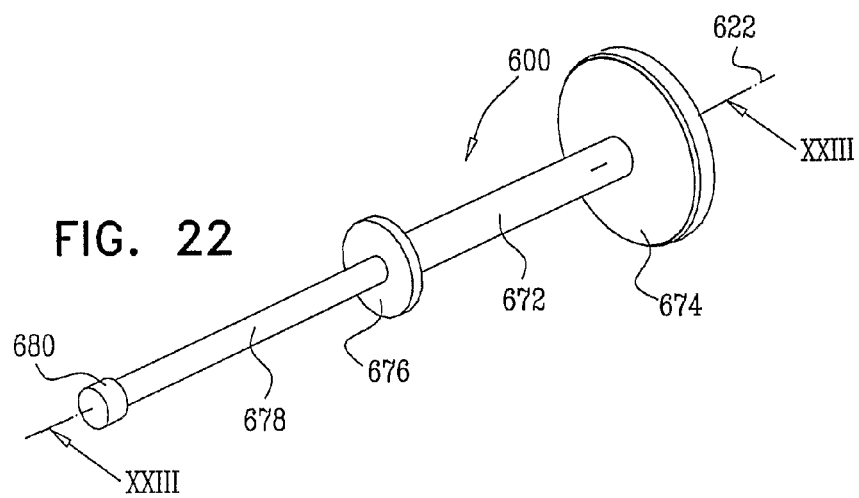
FIG. 22
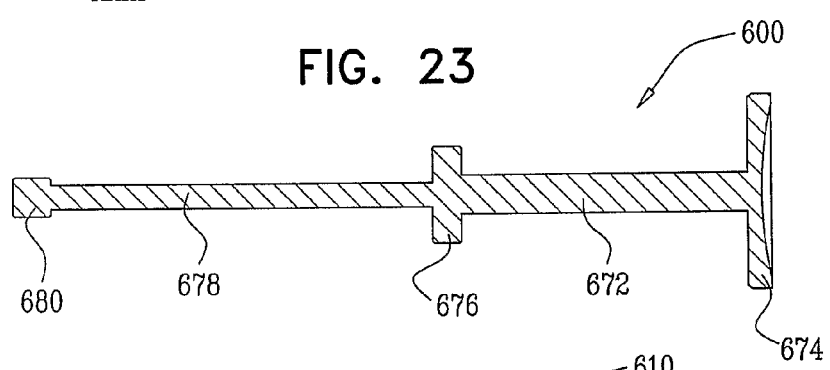
FIG. 23
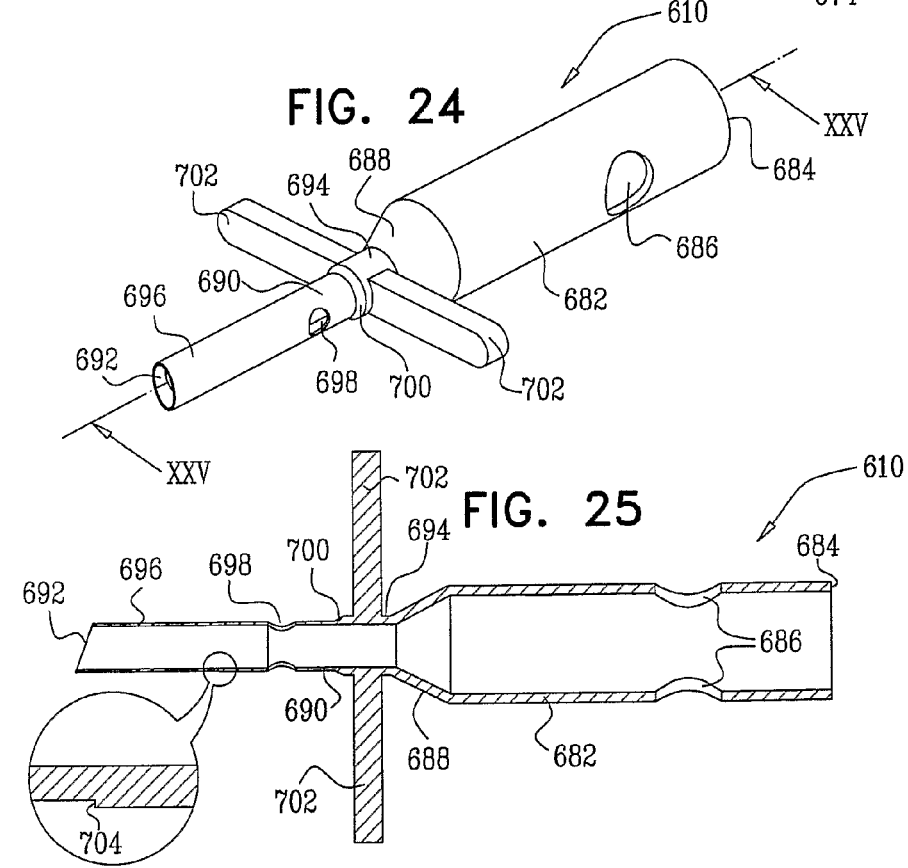
FIG. 24
FIG. 25

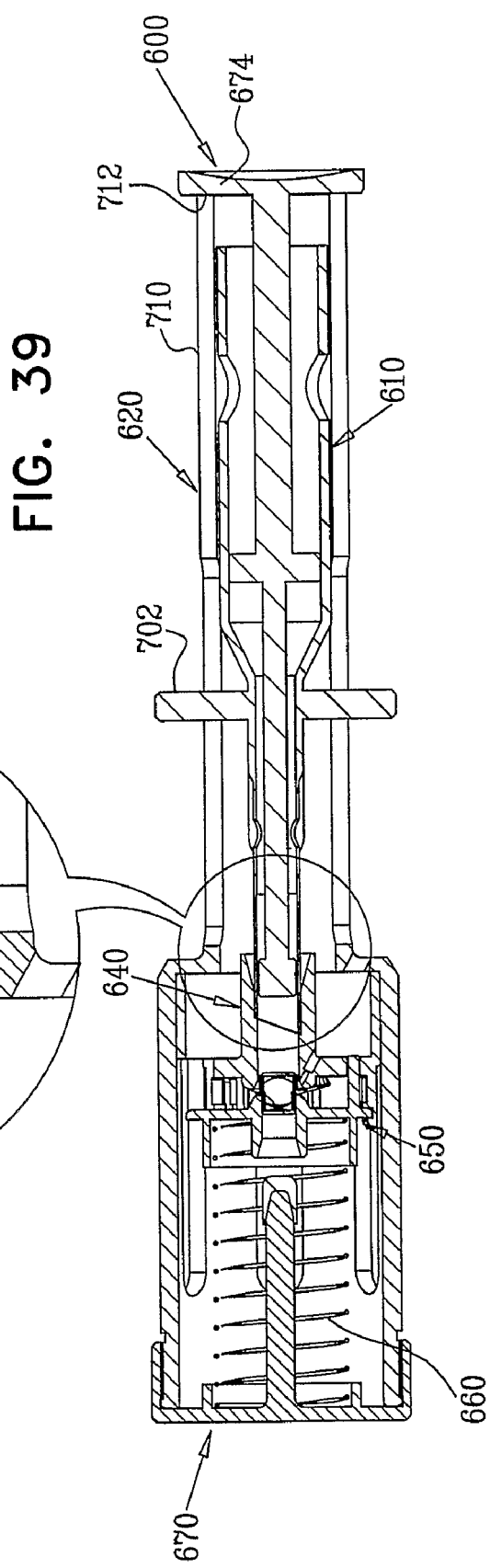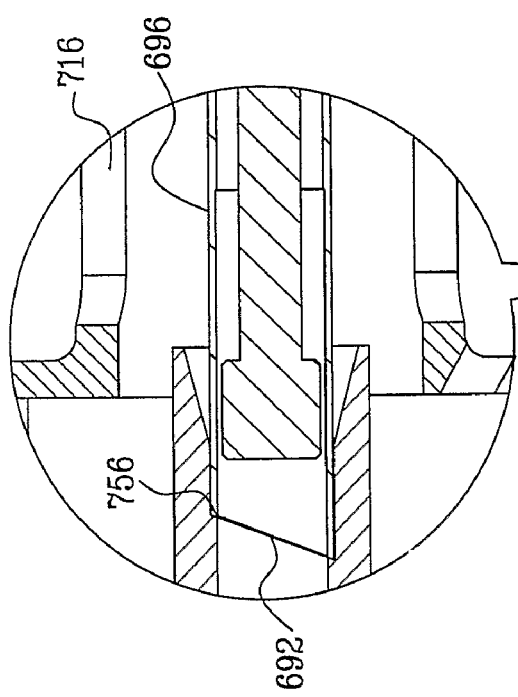
FIG. 39

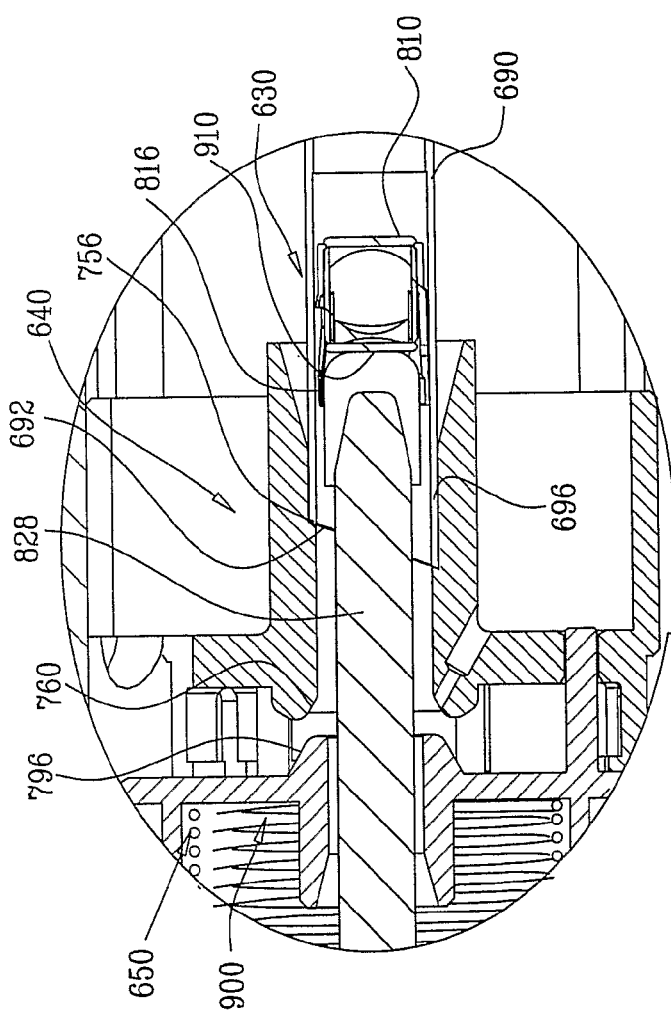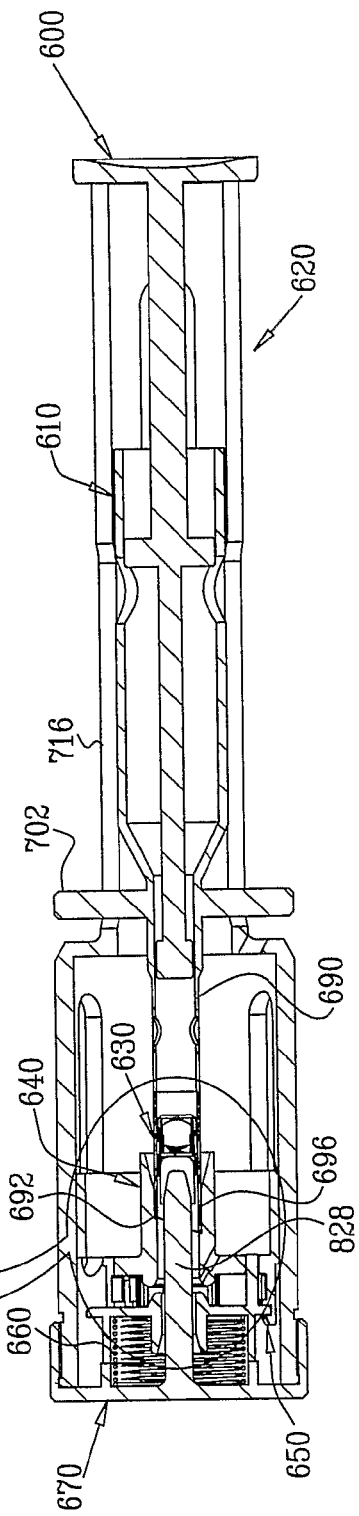
FIG. 41

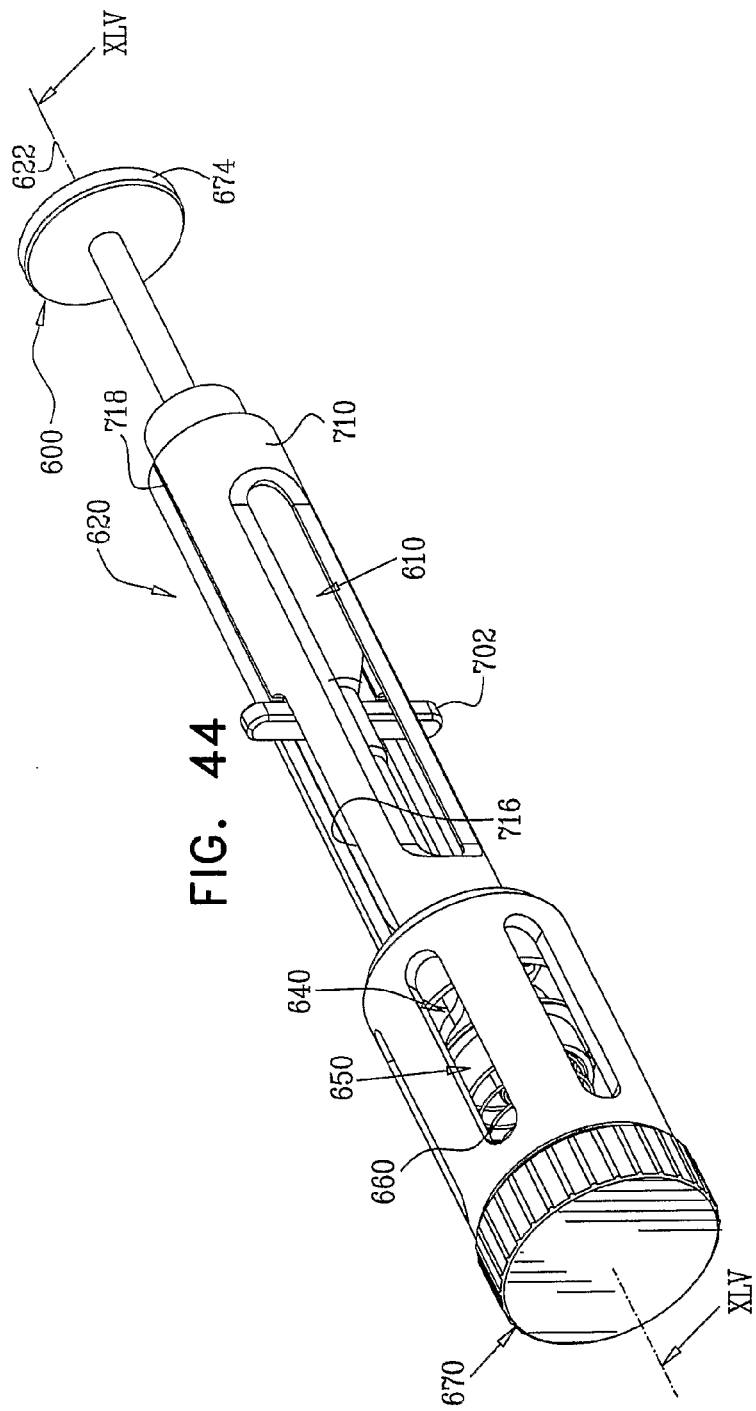
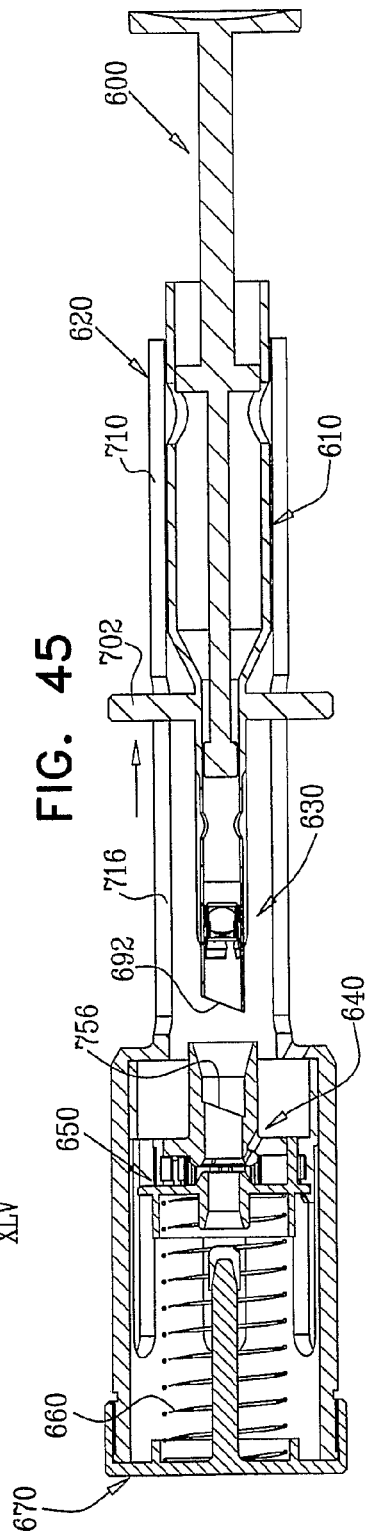
FIG. 44
FIG. 45

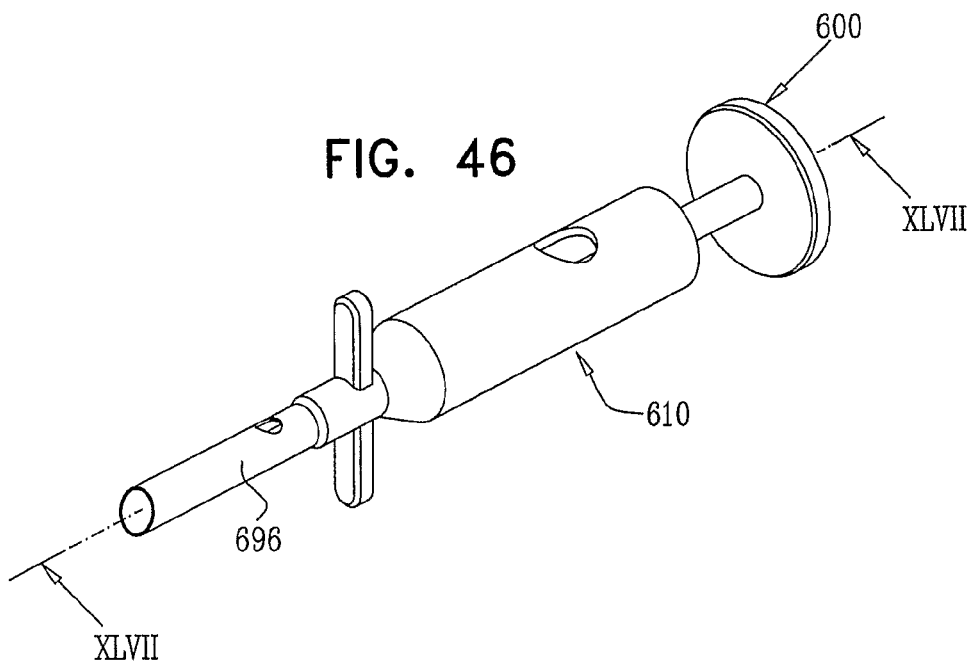
FIG. 46
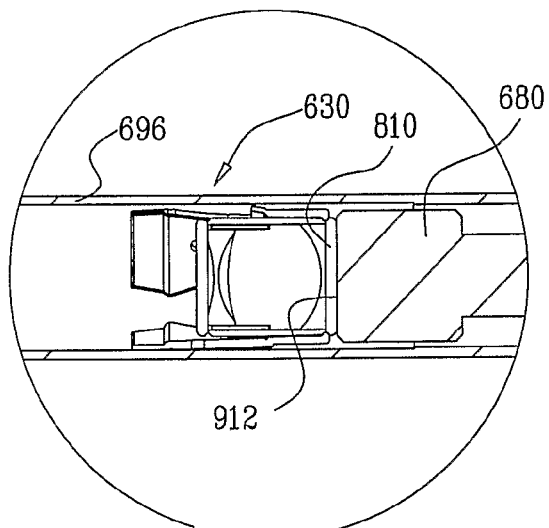
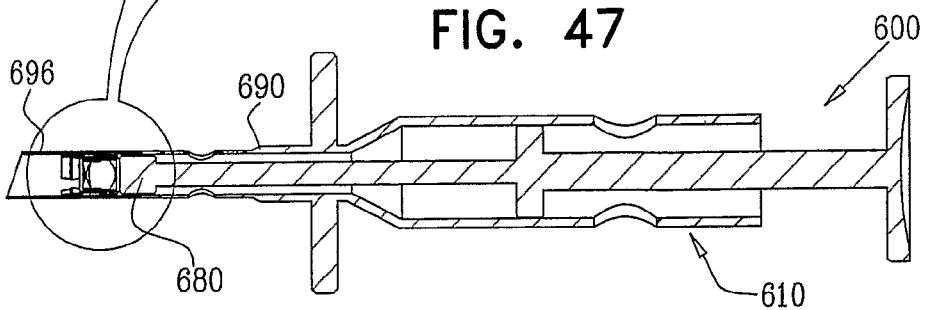
FIG. 47

INJECTABLE INTRAOCULAR IMPLANTS

CROSS-REFERENCE TO RELATED APPLICATIONS

This application is the U.S. National Phase Application of International Application No. PCT/IL2006/000873, filed on Jul. 27, 2006 which claims benefit of U.S. patent application Ser. No. 11/193,781, filed Jul. 28, 2005, entitled COMPRESSED HAPTICS, the disclosure of which is hereby incorporated by reference and priority of which is hereby claimed pursuant to 37 CFR 1.78(a)(4) and (5)(i). The International Application was published in English on Feb. 1, 2007 as WO 2007/013080 A2 under PCT Article 21(2).

FIELD OF THE INVENTION

The present invention relates to ocular implants generally and more particularly to intraocular implants.

BACKGROUND OF THE INVENTION

The following patent publications are believed to represent the current state of the art:

U.S. Pat. Nos. 5,814,103; 5,876,442; 5,928,283; 6,007,579; 6,066,171; 5,653,751; 6,596,026; 6,464,725; 5,391,202; 5,384,606; 4,074,368; 4,994,082; 5,628,798; 5,222,981; 4,172,297; 5,769,890; 4,892,543; 4,373,218; 4,968,127; 4,759,761; 4,976,732 and 5,769,889;

Published U.S. Application 2001/018,612;

Published PCT Applications WO 94/07,435; WO 00/38593 and WO 83/01566;

Foreign Patent Publications DE 4,403,326; EP 1,092,402; EP 0,419,740; GB 2,181,355; EP 0,897,702; EP 0,212,616; DE 3,428,895 and DE 19,501,444.

SUMMARY OF THE INVENTION

The present invention seeks to provide an improved intraocular implant.

There is thus provided in accordance with a preferred embodiment of the present invention an injectable intraocular implant including an optics portion and a resilient, flexible haptics portion mounted coaxially with the optics portion.

In accordance with a preferred embodiment of the present invention the optics portion and the haptics portion are arranged for mutual snap fit engagement. Preferably, the optics portion includes a telescope. Additionally or alternatively, the haptics portion is formed of biocompatible plastic.

In accordance with another preferred embodiment of the present invention the haptics portion includes a cylindrical portion having integrally formed therewith a plurality of outwardly extending haptics wings. Alternatively, the haptics portion includes an outwardly extending helical portion including at least one helical section. Preferably, each of the at least one helical section includes a haptics spiral portion, a residual spiral portion and a frangible portion connecting the haptics spiral portion and the residual spiral portion.

In accordance with yet another preferred embodiment of the present invention the haptics portion includes a hollow, generally cylindrical structure defining a generally circular inward facing wall portion and a generally circular outward facing wall portion. Preferably, the inward facing wall portion defines a generally circular optics engagement aperture therein. Additionally or alternatively, the inward facing wall portion and the outward facing wall portion each define a generally circular optics engagement aperture therein. Additionally or alternatively, each of the haptics wings is tinted so as to block passage of parasitic light therethrough.

There is also provided in accordance with another preferred embodiment of the present invention a method for inserting an intraocular implant into an eye including providing an injectable intraocular implant including an optics portion and a resilient, flexible haptics portion mounted coaxially with the optics portion, locating the injectable intraocular implant in a delivery tube of a syringe, inserting the delivery tube into a lens capsule of an eye and injecting the injectable intraocular implant into the lens capsule.

In accordance with a preferred embodiment of the present invention the injecting includes utilizing fluid pressure to force the implant into the lens capsule. Preferably, the fluid is biocompatible fluid. Additionally or alternatively, the haptics portion includes haptics wings and the locating includes folding the haptics wings over the optics portion.

In accordance with another preferred embodiment of the present invention the locating includes arranging the implant with an outward facing end of the optics portion arranged rearward in the delivery tube. Preferably, the haptics portion includes an outwardly extending helical portion and the locating includes winding the helical portion into a coil. Additionally, the injecting includes rotating the syringe.

In accordance with yet another preferred embodiment of the present invention the outwardly extending helical portion includes a haptics spiral portion, a residual spiral portion and a frangible portion connecting the haptics spiral portion and the residual spiral portion and the rotating causes the frangible portion to break, thereby separating the haptics spiral portion from the residual spiral portion.

In accordance with still another preferred embodiment of the present invention the haptics portion includes an outward facing wall portion and the locating includes pulling the outward facing wall portion over an outward facing end of the optics portion. Preferably, the locating includes sealing a fluid flow passageway in the syringe. Additionally, the injecting includes unsealing the fluid flow passageway.

In accordance with a further preferred embodiment of the present invention the locating includes drawing the haptics portion into a delivery syringe. Preferably, the method also includes puncturing the haptics portion.

There is further provided in accordance with a further preferred embodiment of the present invention an intraocular implant injection assembly including an intraocular implant positioning subassembly, an intraocular implant including haptics and having an optical axis, the intraocular implant being mounted in the intraocular implant positioning subassembly in one of at least one first predetermined azimuthal orientation with respect to the subassembly, a housing retaining the intraocular implant positioning subassembly, in one of at least one second predetermined azimuthal orientation with respect to the housing and a syringe having an angled forward edge, the syringe being retained in the housing, such that the angled forward edge is in one of at least one third predetermined azimuthal orientation with respect to the housing.

There is yet further provided in accordance with yet a further preferred embodiment of the present invention an intraocular implant injection assembly including an intraocular implant positioning subassembly, an intraocular implant including haptics and having an optical axis, the intraocular implant being mounted in the intraocular implant positioning subassembly in one of at least one first predetermined azimuthal orientation with respect to the subassembly, a housing retaining the intraocular implant positioning subassembly, in one of at least one second predetermined azimuthal orientation with respect to the housing and a syringe having a user-sensible azimuthal orientation indicator, the syringe being retained in the housing, in one of at least one third predetermined azimuthal orientation with respect to the housing.

In accordance with a preferred embodiment of the present invention, the syringe has an angled forward edge and is retained in the housing, such that the angled forward edge is in one of at least one fourth predetermined azimuthal orientation with respect to the housing.

In accordance with another preferred embodiment of the present invention, the intraocular implant positioning subassembly includes a rearward positioning element including an azimuthal registration aperture and a forward positioning element including an azimuthal registration pin operative to engage the azimuthal registration aperture and to prevent relative rotation between the rearward positioning element and the forward positioning element. Preferably, the forward positioning element includes a circumferential flange and the rearward positioning element includes a plurality of snap-fit engagement elements, operative to engage the circumferential flange by snap-fit engagement.

In accordance with yet another preferred embodiment of the present invention a slanted portion of the haptics lies between a forward, inwardly facing, tapered portion of the rearward positioning element and a rearward, outwardly facing, tapered portion of the forward positioning element. Preferably, the tapered portion of the rearward positioning element and the tapered portion of the forward positioning element are configured to guide the haptics while the intraocular implant is loaded into the syringe, thereby maintaining mechanical integrity of the haptics.

In accordance with still another preferred embodiment of the present invention the intraocular implant positioning subassembly includes a plurality of intraocular implant positioning protrusions operative to retain the intraocular implant in the one of at least one first predetermined azimuthal orientation with respect to the subassembly. Preferably, the intraocular implant positioning subassembly includes an angled shoulder having an angular orientation which is generally identical to that of the forward angled edge and which is adapted to engage the forward angled edge, thereby to provide at least one predetermined azimuthal orientation of the syringe with respect to the intraocular implant positioning subassembly.

In accordance with a further preferred embodiment of the present invention the forward angled edge of the syringe is configured to allow the haptics to unfold sequentially as the intraocular implant is injected into an eye. Preferably, the housing includes at least one longitudinal slot, arranged to slidably accommodate the user-sensible azimuthal orientation indicator. Additionally or alternatively, the housing is formed of a resilient material and is at least partially bifurcated to permit insertion thereinto of the syringe.

In accordance with yet a further preferred embodiment of the present invention the intraocular implant injection assembly also includes an intraocular implant displacer adapted to engage the housing. Preferably, the intraocular implant displacer includes a shaft portion operative to push the intraocular implant from the positioning subassembly into the syringe. Additionally or alternatively the haptics are adapted to fold over a body portion of the intraocular implant and symmetrically about the optical axis, and to extend forwardly of the body portion when the intraocular implant is located within the syringe.

In accordance with still a further preferred embodiment of the present invention the intraocular implant includes a capsular body portion and the haptics are adapted to urge the capsular body portion away from the cornea when the intraocular implant is implanted in the eye. Preferably, the haptics include a plurality of haptics wings, each being tinted so as to block passage of parasitic light therethrough.

There is also provided in accordance with another preferred embodiment of the present invention an intraocular implant injection assembly including an intraocular implant including haptics, a syringe having an angled forward edge and an intraocular implant azimuthal positioner operative to retain the intraocular implant in one of at least one predetermined azimuthal orientation with respect to the angled forward edge of the syringe.

There is additionally provided in accordance with yet another preferred embodiment of the present invention an intraocular implant injection assembly including an intraocular implant including haptics, a syringe having a user-sensible azimuthal orientation indicator and an intraocular implant azimuthal positioner operative to retain the intraocular implant in one of at least one predetermined azimuthal orientation with respect to the syringe. Preferably, the syringe has an angled forward edge and the intraocular implant azimuthal positioner is operative to retain the intraocular implant in the one of at least one predetermined azimuthal orientation with respect to the angled forward edge of the syringe.

In accordance with a preferred embodiment of the present invention the intraocular implant azimuthal positioner includes a rearward positioning element including an azimuthal registration aperture and a forward positioning element including an azimuthal registration pin operative to engage the azimuthal registration aperture and to prevent relative rotation between the rearward positioning element and the forward positioning element. Preferably, the forward positioning element includes a circumferential flange and the rearward positioning element includes a plurality of snap-fit engagement elements, operative to engage the circumferential flange by snap-fit engagement.

In accordance with another preferred embodiment of the present invention a slanted portion of the haptics lies between a forward, inwardly facing, tapered portion of the rearward positioning element and a rearward, outwardly facing, tapered portion of the forward positioning element. Preferably, the tapered portion of the rearward positioning element and the tapered portion of the forward positioning element are configured to guide the haptics while the intraocular implant is loaded into the syringe, thereby maintaining mechanical integrity of the haptics.

In accordance with yet another preferred embodiment of the present invention the intraocular implant azimuthal positioner includes a plurality of intraocular implant positioning protrusions operative to retain the intraocular implant in the one of at least one predetermined azimuthal orientation with respect to the syringe. Preferably, the intraocular implant azimuthal positioner includes an angled shoulder having an angular orientation which is generally identical to that of the angled forward edge and which is adapted to engage the angled forward edge, thereby to provide the one of at least one predetermined azimuthal orientation between the intraocular implant and the syringe.

In accordance with a further preferred embodiment of the present invention the intraocular implant injection assembly also includes an intraocular implant displacer including a shaft portion operative to push the intraocular implant from the intraocular implant azimuthal positioner into the syringe. Preferably, the haptics are adapted to fold over a body portion of the intraocular implant and symmetrically about the optical axis, and to extend forwardly of the body portion when the intraocular implant is located within the syringe. Additionally or alternatively, the angled forward edge of the syringe is configured to allow the haptics to sequentially unfold when the intraocular implant is injected into an eye.

In accordance with yet a further preferred embodiment of the present invention the intraocular implant includes a capsular body portion and the haptics are adapted to urge the capsular body portion away from the cornea when the intraocular implant is implanted in the eye. Preferably, the haptics include a plurality of haptics wings, each being tinted so as to block passage of parasitic light therethrough.

There is further provided in accordance with a further preferred embodiment of the present invention a method for injecting an intraocular implant into an eye, the method including providing an intraocular implant including haptics and having an optical axis, arranging the intraocular implant inside an injector having an injector axis, such that the optical axis is parallel to the injector axis and injecting the intraocular implant into the eye by displacing the intraocular implant along an injection axis which is coaxial with the optical axis. Preferably, the arranging includes arranging the intraocular implant inside the injector such that the optical axis is coaxial with the injector axis.

There is yet further provided in accordance with a yet further preferred embodiment of the present invention a system for injecting an intraocular implant into an eye, including an intraocular implant including haptics and having an optical axis, an injector having an injector axis, adapted to have the intraocular implant arranged therein such that the optical axis is parallel to the injector axis and an intraocular implant displacer operative to inject the intraocular implant into the eye by displacing the intraocular implant along an injection axis which is coaxial with the optical axis. Preferably, the intraocular implant arranged in the injector such that the injector axis is coaxial with the optical axis.

BRIEF DESCRIPTION OF THE DRAWINGS

The present invention will be understood and appreciated more fully from the following detailed description, taken in conjunction with the drawings in which:

FIGS. 1C and 1D are simplified respective exploded and assembled side view illustrations of the injectable intraocular implant of FIGS. 1A and 1B;

FIGS. 4A, 4B, 4C and 4D are simplified sectional illustrations of four stages of the injection of the intraocular implant of FIGS. 1A-1D in the delivery syringe arrangement of FIGS. 2 and 3 into the eye of a patient;

FIGS. 7A, 7B, 7C and 7D are simplified sectional illustrations of four stages of the injection of the intraocular implant of FIGS. 1A-1D in the delivery syringe arrangement of FIGS. 5 and 6 into the eye of a patient;

FIGS. 8A and 8B are simplified respective exploded and assembled pictorial illustrations of an injectable intraocular implant constructed and operative in accordance with another preferred embodiment of the present invention;

FIGS. 16A and 16B are simplified respective exploded and assembled pictorial illustrations of an injectable intraocular implant constructed and operative in accordance with still another preferred embodiment of the present invention;

FIG. 16C is a simplified assembled side view illustration of the injectable intraocular implant of FIGS. 16A and 16B;

FIGS. 21A and 21B are, respectively, a simplified exploded view illustration and a simplified pictorial illustration of an injection assembly for an intraocular implant, constructed and operative in accordance with a further preferred embodiment of the present invention;

FIG. 22 is a simplified pictorial illustration of a plunger forming part of the injection assembly of FIGS. 21A and 21B;

FIG. 23 is a simplified sectional illustration of the plunger of FIG. 22, taken along section lines XXIII-XXIII in FIG. 22;

FIG. 24 is a simplified pictorial illustration of a syringe forming part of the injection assembly of FIGS. 21A and 21B;

FIG. 25 is a simplified sectional illustration of the syringe of FIG. 24, taken along section lines XXV-XXV in FIG. 24;

FIG. 39 is a simplified sectional illustration of the injection assembly of FIG. 38, taken along section lines XXXIX-XXXIX in FIG. 38;

FIG. 41 is a simplified sectional illustration of the injection assembly of FIG. 40, taken along section lines XLI-XLI in FIG. 40;

FIG. 44 is a simplified pictorial illustration of the injection assembly of FIGS. 42 and 43 in a full syringe retraction orientation;

FIG. 45 is a simplified sectional illustration of the injection assembly of FIG. 44, taken along section lines XLV-XLV in FIG. 44;

FIG. 46 is a simplified pictorial illustration of the syringe of FIGS. 21A and 21B in a ready to use orientation;

FIG. 47 is a simplified sectional illustration of the syringe of FIG. 46, taken along section lines XLVII-XLVII in FIG. 46.

DETAILED DESCRIPTION OF PREFERRED EMBODIMENTS

Figure 1A:
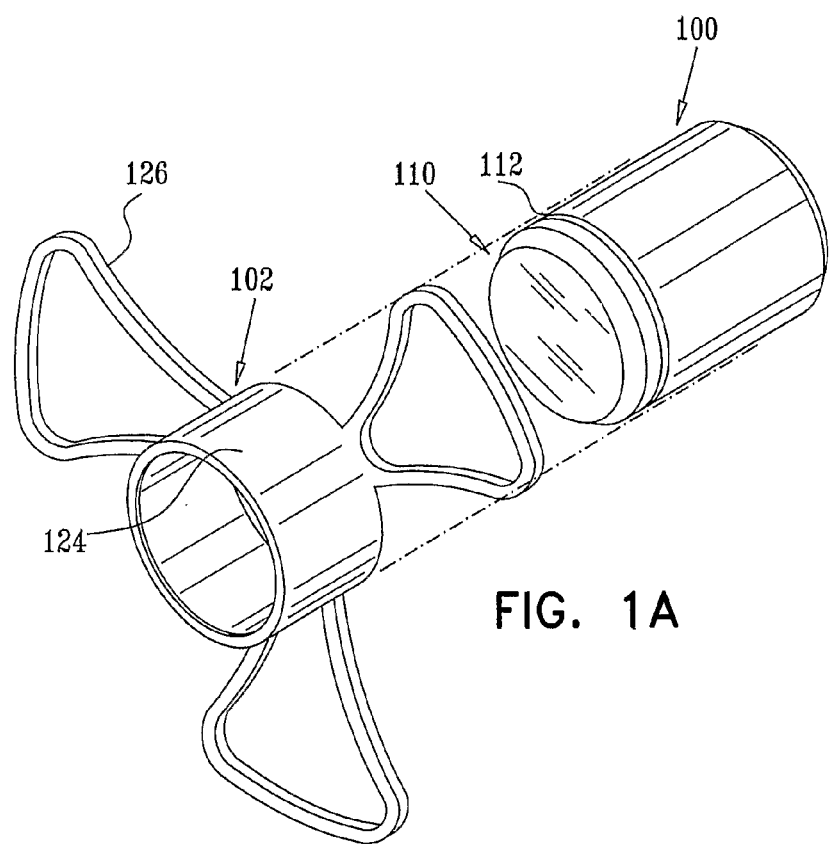
FIGS. 1A and 1B are simplified respective exploded and assembled pictorial illustrations of an injectable intraocular implant constructed and operative in accordance with a preferred embodiment of the present invention.
Figure 1B:
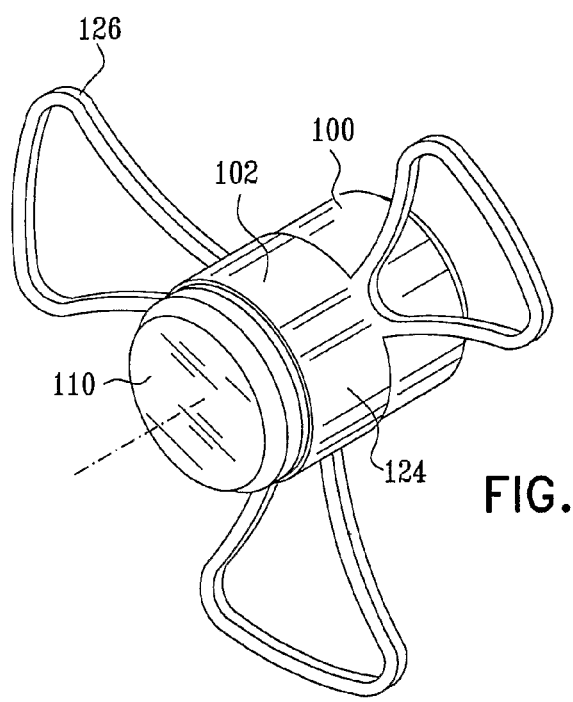

Reference is now made to FIGS. 1A-1D, which illustrate an injectable intraocular implant constructed and operative in accordance with a preferred embodiment of the present invention. It is seen that the implant preferably includes an optics portion 100 and a haptics portion 102 which is preferably snap-fitted onto the optics portion 100.

The optics portion 100 may be any suitable optics portion and is preferably, but not necessarily, a telescope. Preferred intraocular implants are described in applicants/assignee's published patent documents listed hereinbelow, the disclosures of which are hereby incorporated by reference:

U.S. Pat. Nos. 5,391,202; 5,354,335; 5,814,103; 5,876,442; 5,928,283; 6,007,579; 6,066,171; 6,569,199 and 6,596,026, and U.S. published applications U.S. Ser. Nos. 10/342,160 and 10/321,793.

The optics portion 100 may incorporate any one or more of the features described in the abovementioned patent documents in any suitable combination and is preferably in the form of a cylinder having adjacent one end thereof, hereinafter referred to as the outward facing end 110, a peripheral groove 112. The haptics portion 102 is preferably formed of a resilient, flexible material, such as biocompatible plastic, and includes a cylindrical portion 124 having integrally formed therewith a plurality of outwardly extending haptics wings 126. Cylindrical portion 124 is preferably formed with an inwardly directed peripheral protrusion 128 adjacent one end thereof, hereinafter referred to as the outward facing end 130. Protrusion 128 is arranged for normally non-removable snap-fit engagement with groove 112 on optics portion 100, when cylindrical portion 124 is in coaxial surrounding relationship with optics portion 100 as shown.

It is appreciated that the haptics wings 126 are preferably at least partially opaque, so as to block passage of parasite light therethrough.

It is appreciated that the peripheral groove 112 of the optics portion 100 may be located at any suitable location therealong and the inwardly directed peripheral protrusion 128 of cylindrical portion 124 of haptics portion 102 may be located at any suitable location therealong to provide normally non-removable snap-fit engagement of optics portion 100 and haptics portion 102.

Figure 2:
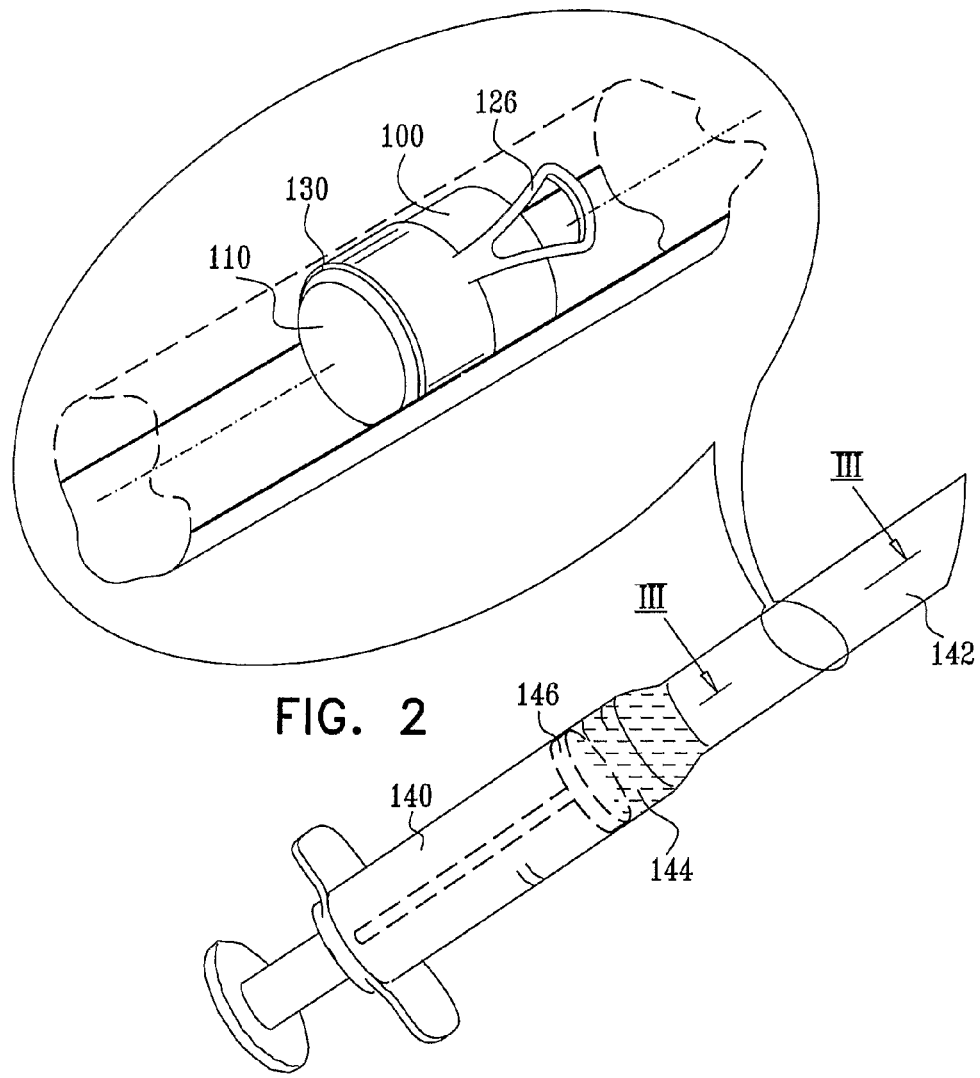
FIGS. 2 and 3 are simplified pictorial and sectional illustrations of the injectable intraocular implant of FIGS. 1A-1D located in a fluid-filled hypodermic delivery syringe.
Figure 3:
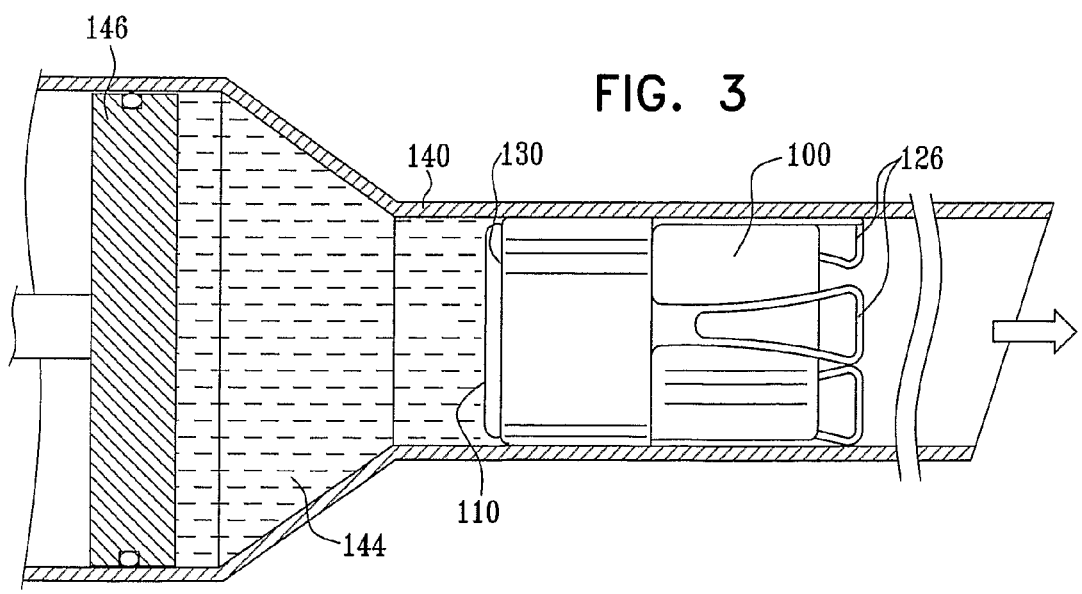

Reference is now made to FIGS. 2 and 3, which are simplified pictorial and sectional illustrations of the injectable intraocular implant of FIGS. 1A-1D located in a fluid-filled hypodermic delivery syringe 140. It is seen that haptics wings 126 are folded over the optics portion 100 and that the implant is arranged with outward facing ends 110 and 130 arranged rearward in a delivery tube 142 of delivery syringe 140. Fluid, such as biocompatible fluid 144, is located forward of a piston 146 of delivery syringe 140 and rearward of the implant.

Reference is now made to FIGS. 4A, 4B, 4C and 4D, which are simplified sectional illustrations of four stages of the injection of the intraocular implant of FIGS. 1A-1D in the delivery syringe arrangement of FIGS. 2 and 3 into the eye of a patient. FIG. 4A shows initial insertion of the tip of the delivery tube 142 of delivery syringe 140 into the lens capsule of the eye. FIG. 4B shows the implant being forced out of the delivery syringe 140 into the lens capsule. FIG. 4C shows unfolding of haptics wings 126 inside the lens capsule and FIG. 4D shows proper orientation of the implant, including fully deployed haptics wings 126, within the lens capsule.

Figure 5:
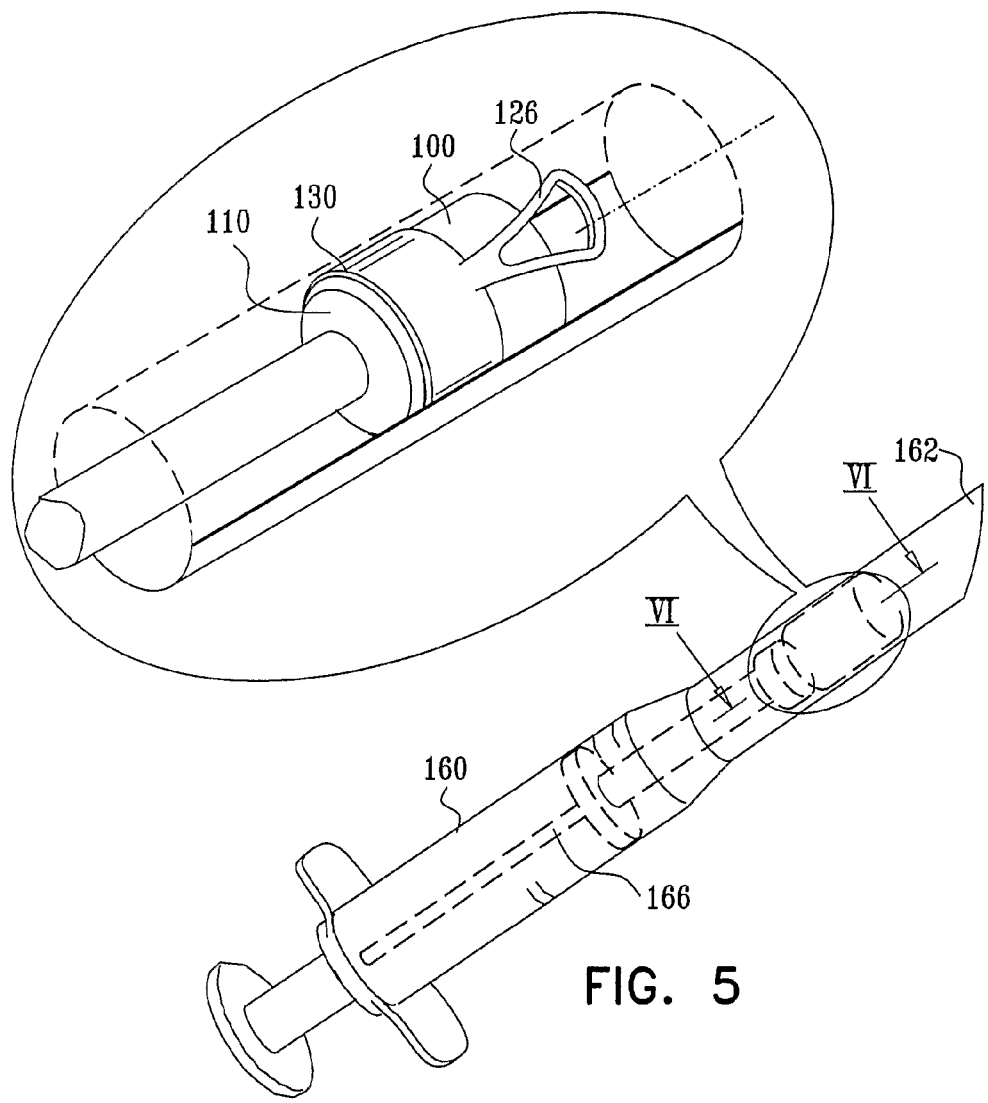
FIGS. 5 and 6 are simplified pictorial and sectional illustrations of the injectable intraocular implant of FIGS. 1A-1D located in a specially designed, non fluid-filled hypodermic delivery syringe.
Figure 6:
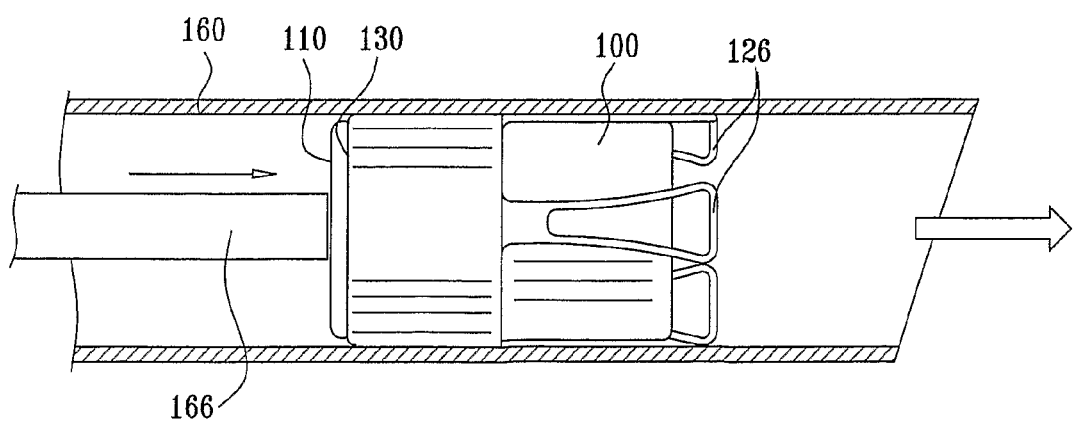

Reference is now made to FIGS. 5 and 6, which are simplified pictorial and sectional illustrations of the injectable intraocular implant of FIGS. 1A-1D located in a specially designed, non fluid-filled hypodermic delivery syringe 160. It is seen that haptics wings 126 are folded over the optics portion 100 and that the implant is arranged with outward facing ends 110 and 130 arranged rearward in a delivery tube 162 of delivery syringe 160. A piston 166 of delivery syringe 160 engages outward facing end 110 of the optics portion 100 of the implant.

Reference is now made to FIGS. 7A, 7B, 7C and 7D, which are simplified sectional illustrations of four stages of the injection of the intraocular implant of FIGS. 1A-1D in the delivery syringe arrangement of FIGS. 5 and 6 into the eye of a patient. FIG. 7A shows initial insertion of the tip of the delivery tube 162 of delivery syringe 160 into the lens capsule of the eye. FIG. 7B shows the implant being forced out of the delivery syringe 160 into the lens capsule. FIG. 7C shows unfolding of haptics wings 126 inside the lens capsule and FIG. 7D shows proper orientation of the implant, including fully deployed haptics wings 126, within the lens capsule.

Reference is now made to FIGS. 5A-8D, which illustrate an injectable intraocular implant constructed and operative in accordance with another preferred embodiment of the present invention. It is seen that the implant preferably includes an optics portion 200 and a haptics portion 202 which is preferably snap-fitted onto the optics portion 200.

The optics portion 200 may be any suitable optics portion and is preferably, but not necessarily, a telescope. Preferred intraocular implants are described in applicants/assignee's published patent documents listed hereinbelow, the disclosures of which are hereby incorporated by reference:

U.S. Pat. Nos. 5,391,202; 5,354,335; 5,814,103; 5,876,442; 5,928,283; 6,007,579; 6,066,171; 6,569,199 and 6,596,026, and U.S. published applications U.S. Ser. Nos. 10/342,160 and 10/321,793.

The optics portion 200 may incorporate any one or more of the features described in the abovementioned patent documents in any suitable combination and is preferably in the form of a cylinder having adjacent one end thereof, hereinafter referred to as the inward facing end 210, a peripheral groove 212. The haptics portion 202 is preferably formed of a resilient, flexible material, such as biocompatible plastic, and includes a generally cylindrical optics engagement portion 220 integrally formed with an outwardly extending helical portion 222 and a generally cylindrical end portion 224.

Cylindrical optics engagement portion 220 is preferably formed with an inwardly directed peripheral protrusion 228 adjacent one end thereof, hereinafter referred to as the inward facing end 230. Protrusion 228 is arranged for normally non-removable snap-fit engagement with groove 212 on optics portion 200, when cylindrical optics engagement portion 220 is in coaxial surrounding relationship with optics portion 200 as shown.

It is appreciated that the peripheral groove 212 of the optics portion 200 may be located at any suitable location therealong and the inwardly directed peripheral protrusion 228 of cylindrical optics engagement portion 220 of haptics portion 202 may be located at any suitable location therealong to provide normally non-removable snap-fit engagement of optics portion 200 and haptics portion 202.

As seen in FIG. 8A, outwardly extending helical portion 222 preferably includes at least one, and preferably two or more, helical section 234 joined at one end to generally cylindrical optics engagement portion 220 and at an opposite end thereof to generally cylindrical end portion 224. Each of the at least one helical sections 234 preferably include a haptics spiral portion 236 connected to residual spiral portion 238 at a notched frangible portion 240. Notched frangible portions 240 provide for separation of haptics spiral portions 236 from residual spiral portion 238, as described hereinbelow with reference to FIG. 11B.

Alternatively, notched frangible portion 240 and residual spiral portion 238 may be obviated and haptics spiral portion 236 may be joined directly to generally cylindrical end portion 224. In this embodiment, end portion 224 is also injected into the lens capsule of an eye, as described hereinbelow with reference to FIGS. 12A-12D.

Figure 8C:
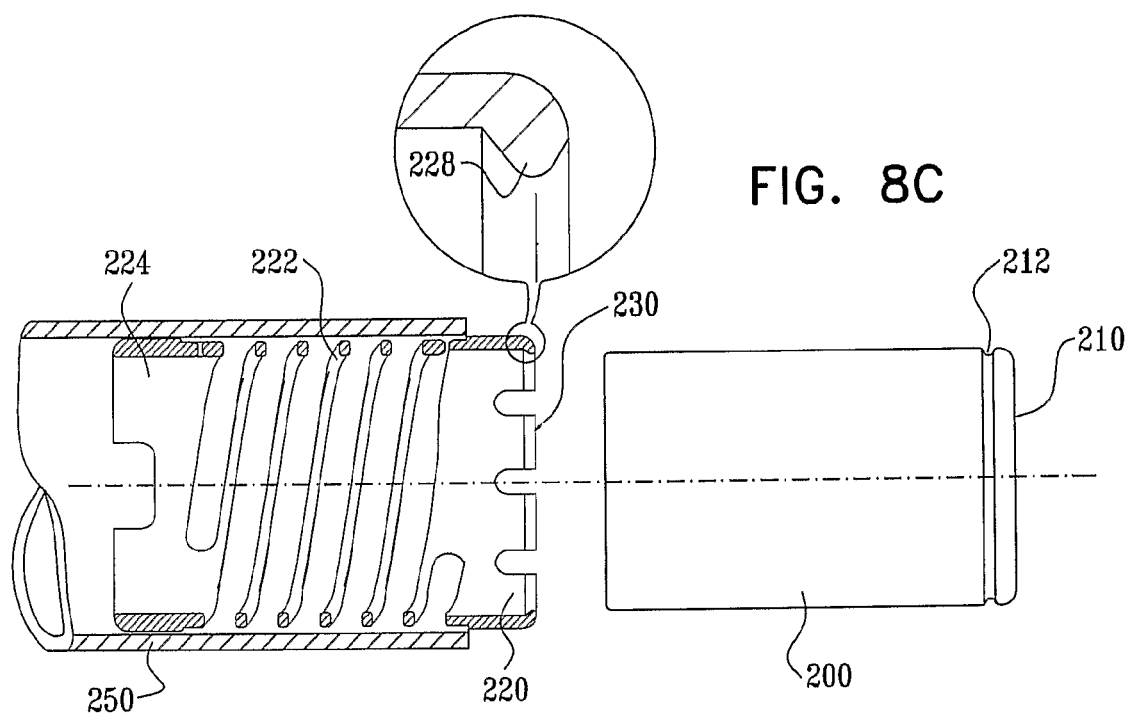
FIGS. 8C and 8D are simplified respective exploded and assembled side view illustrations of the injectable intraocular implant of FIGS. 8A and 8B.
Figure 8D:
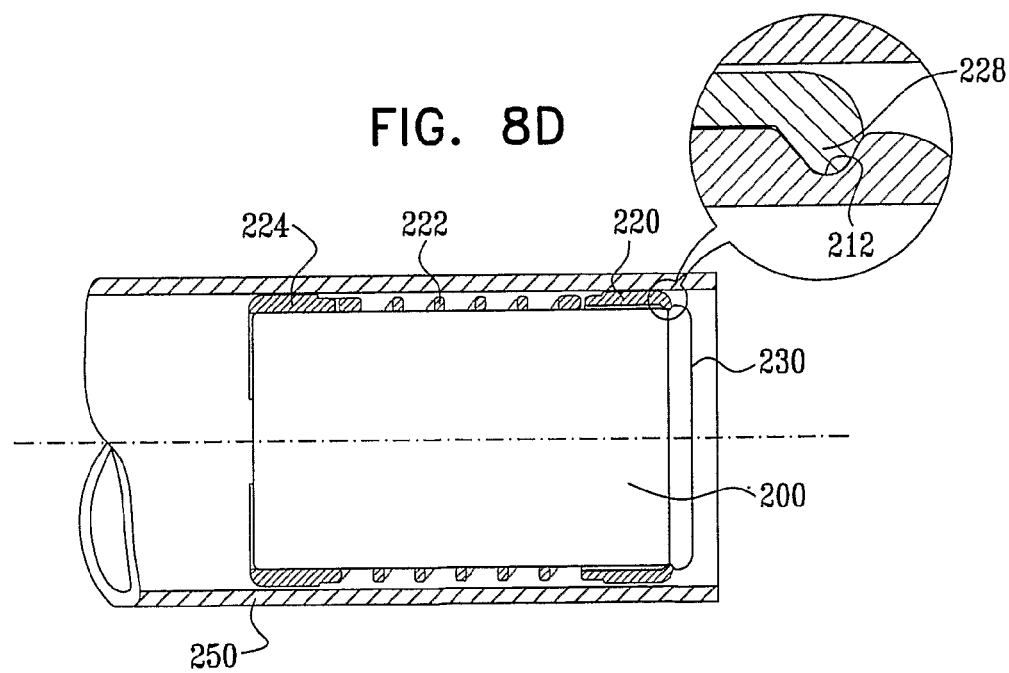

As seen further in FIGS. 8A, 8B and 8C, prior to injection of the intraocular implant of FIGS. 8A-8D into an eye, generally cylindrical end portion 224 is placed into a delivery syringe 250 and outwardly extending helical portion 222 is wound, as indicated by arrows 252 (FIG. 8A), into a tightly coiled position inside delivery syringe 250. As seen in FIG. 8D, cylindrical optics engagement portion 220 is then placed into snap fit engagement with optics portion 200.

Figure 9:
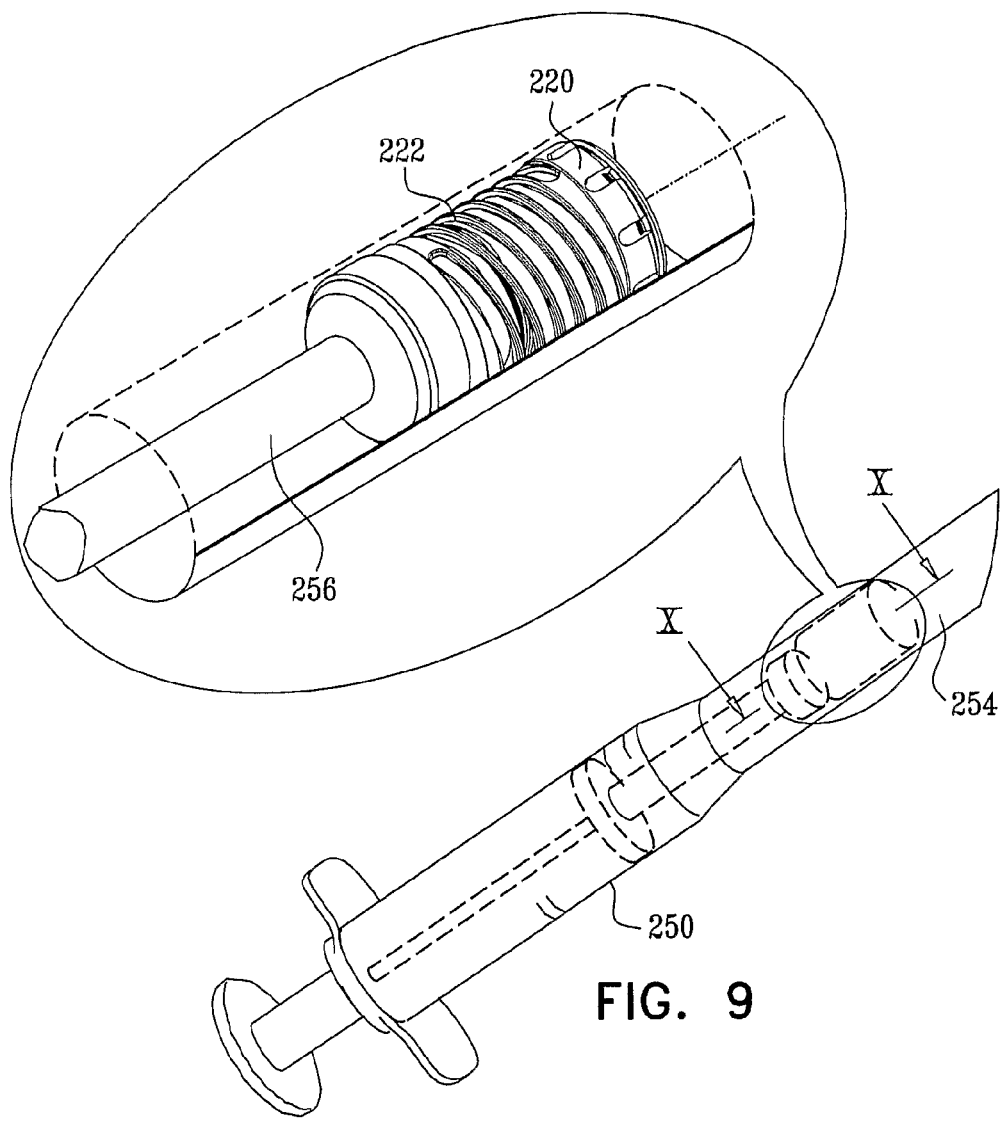
FIGS. 9 and 10 are simplified pictorial and sectional illustrations of the injectable intraocular implant of FIGS. 8A-8D located in a hypodermic delivery syringe.
Figure 10:
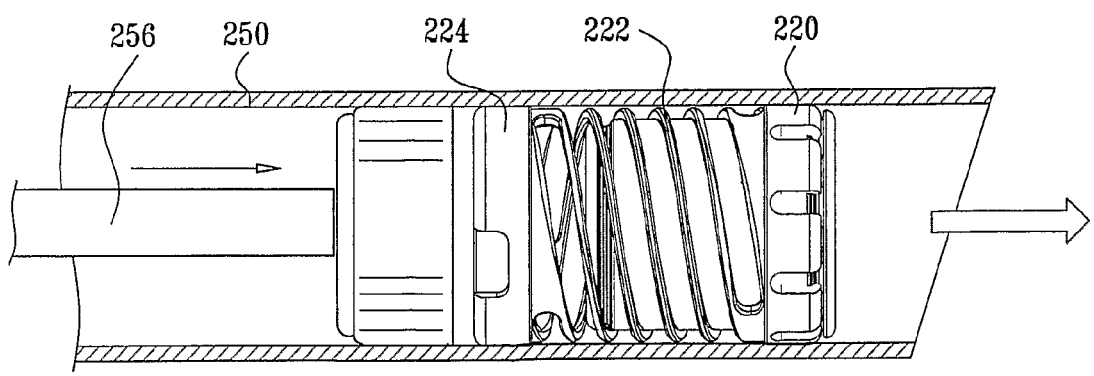

Reference is now made to FIGS. 9 and 10, which are simplified pictorial and sectional illustrations of the injectable intraocular implant of FIGS. 8A-8D located in delivery syringe 250. It is seen that outwardly extending helical portion 222 of haptics portion 202 is coiled over the optics portion 200 and that the implant is arranged with inward facing ends 210 and 230 arranged forwardly in a delivery tube 254 of delivery syringe 250. A piston 256 of delivery syringe 250 engages generally cylindrical end portion 224 of haptics portion 202.

Reference is now made to FIGS. 11A, 11B, 11C and 11D, which are simplified sectional illustrations of four stages of the injection of the intraocular implant of FIGS. 8A-8D in the delivery syringe arrangement of FIGS. 9 and 10 into the eye of a patient.

Figure 11A:
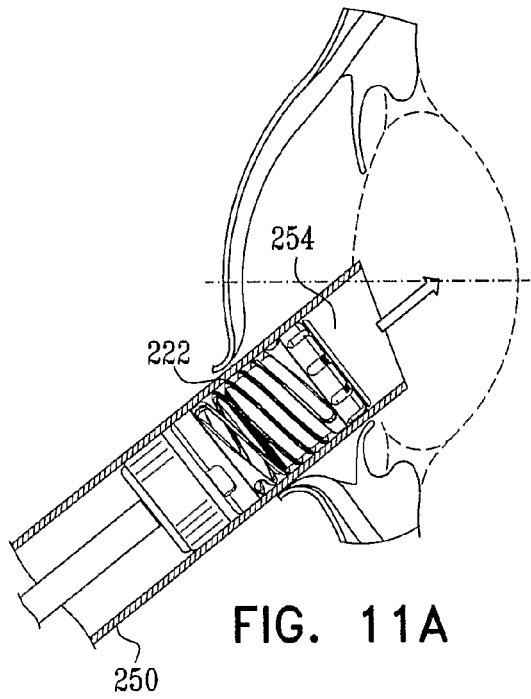
FIGS. 11A, 11B, 11C and 11D are simplified sectional illustrations of four stages of the injection of the intraocular implant of FIGS. 8A-8D in the delivery syringe arrangement of FIGS. 9 and 10 into the eye of a patient.

FIG. 11A shows initial insertion of the tip of the delivery tube 254 of delivery syringe 250 into the lens capsule of the eye.

Figure 11B:
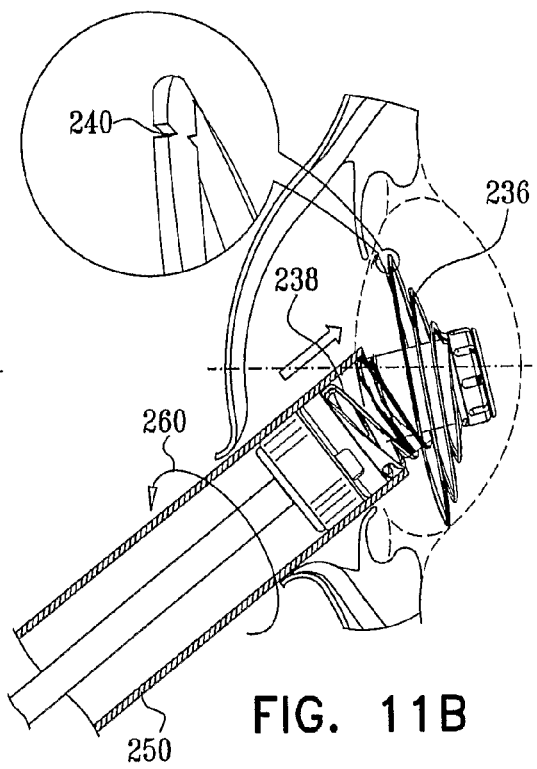

FIG. 11B shows the implant being forced out of the delivery syringe 250 into the lens capsule. As seen in FIG. 11B, haptics spiral portion 236 uncoils and extends outwardly into the lens capsule upon exiting delivery syringe 250. Following the exiting of notched frangible portion 240 from delivery syringe 250, delivery syringe 250 is rotated, as designated by arrow 260, causing frangible portion 240 to break and separating haptics spiral portion 236 and residual spiral portion 238.

Figure 11C:
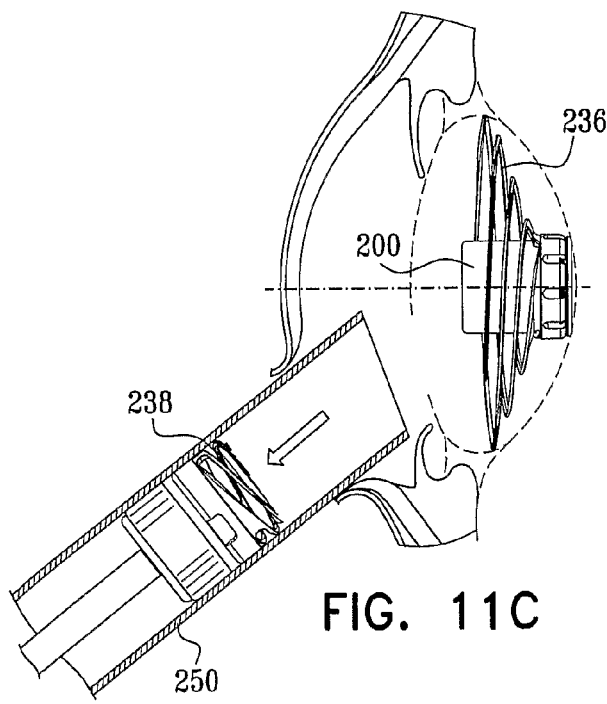

As seen in FIG. 11C, following the separation of haptics spiral portion 236 and residual spiral portion 238, haptics spiral portion 236 remains in the lens capsule together with optics portion 200, while residual spiral portion 238 remains within delivery syringe 250, which is then removed from the eye.

Figure 11D:
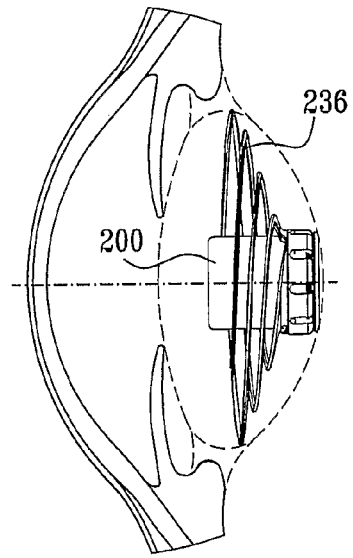

FIG. 11D shows proper orientation of the implant, including fully deployed haptics spiral portion 236 of haptics portion 202 and optics portion 200, within the lens capsule.

Reference is now made to FIGS. 12A, 12B, 12C and 12D, which are simplified sectional illustrations of four stages of the injection of the intraocular implant of FIGS. 8A-8D in the delivery syringe arrangement of FIGS. 9 and 10 into the eye of a patient in accordance with another preferred embodiment of the present invention. In the embodiment of FIGS. 12A-12D, haptics spiral portion 236 of the at least one helical section 234 is preferably joined at one end to generally cylindrical optics engagement portion 220 and at an opposite end thereof to generally cylindrical end portion 224, and helical section 234 preferably does not include a notched frangible portion 240 and residual spiral portion 238. Alternatively, helical section 234 may also include a notched frangible portion 240 and a residual spiral portion 238 joined to end portion 224.

Figure 12A:
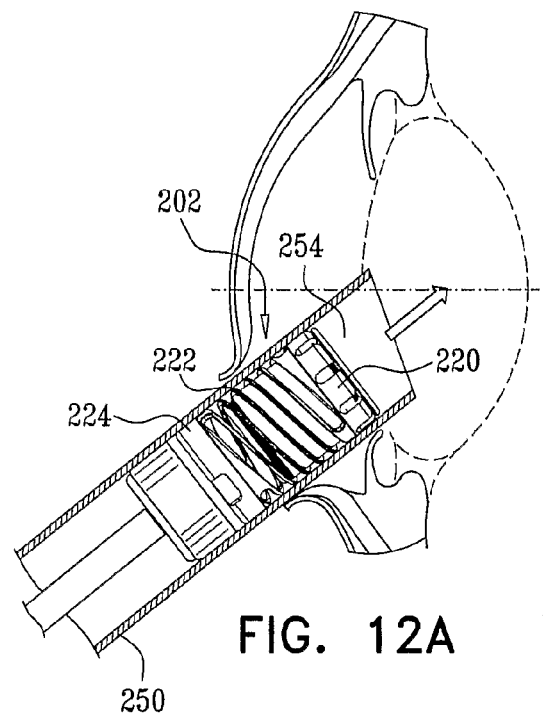
FIGS. 12A, 12B, 12C and 12D are simplified sectional illustrations of four stages of the injection of the intraocular implant of FIGS. 5A-8D in the delivery syringe arrangement of FIGS. 9 and 10 into the eye of a patient in accordance with another preferred embodiment of the present invention.

FIG. 12A shows initial insertion of the tip of the delivery tube 254 of delivery syringe 250 into the lens capsule of the eye.

Figure 12B:
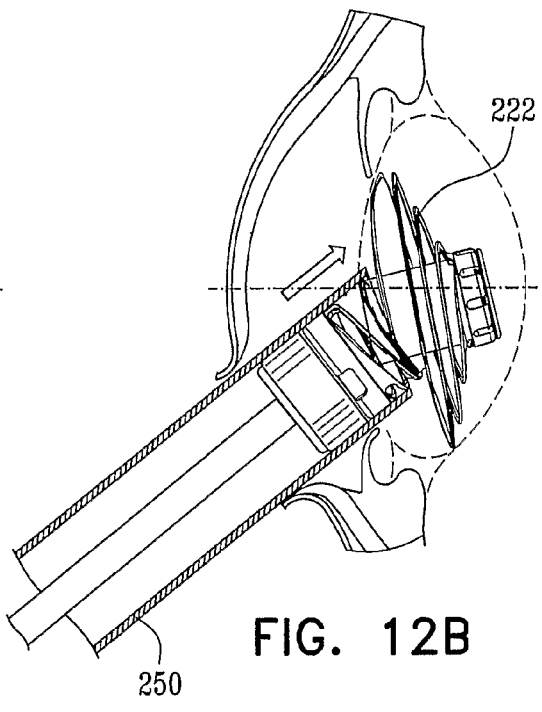

FIG. 12B shows the implant being forced out of the delivery syringe 250 into the lens capsule. As seen in FIG. 12B, haptics spiral portion 236 uncoils and extends outwardly into the lens capsule upon exiting delivery syringe 250. The embodiment of FIG. 12B differs from the embodiment of FIG. 11B in that delivery syringe 250 is not rotated to break notched frangible portion 240 and the entire haptics portion 202 is injected into the lens capsule.

Figure 12C:
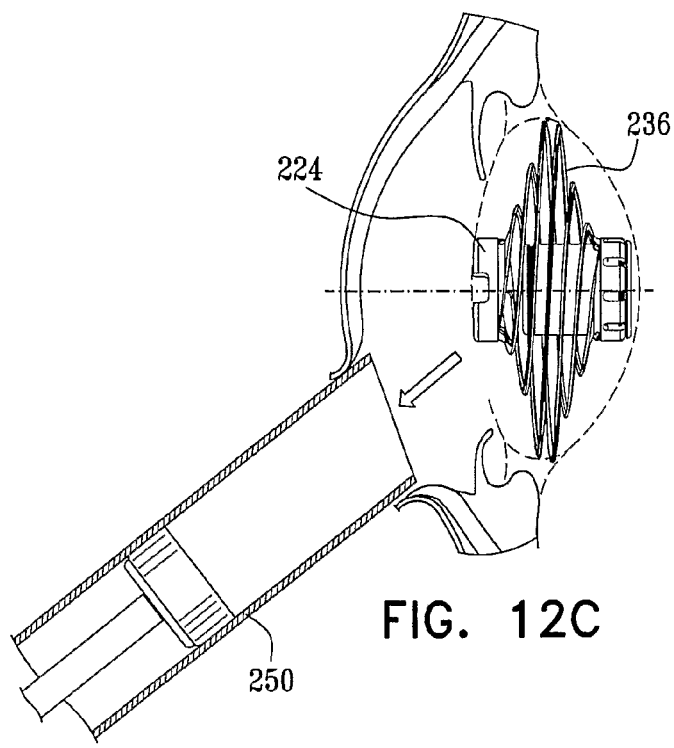
Figure 12D:
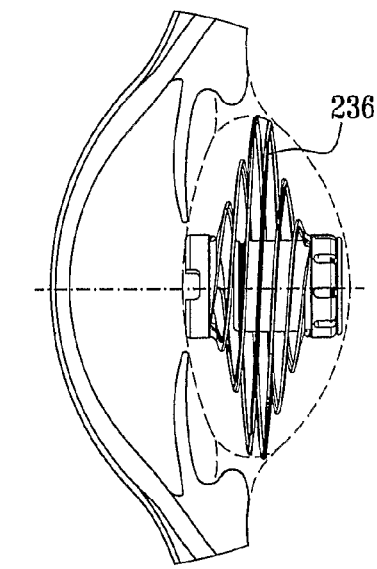

As seen in FIGS. 12C-12D, following the injection of haptics portion 202 and optics portion 200, delivery syringe 250 is removed from the eye and outwardly extending helical portion 222 uncoils to its original form providing proper orientation of the implant, including fully deployed haptics spiral portion 236 of haptics portion 202 and optics portion 200, within the lens capsule.

Figure 13A:
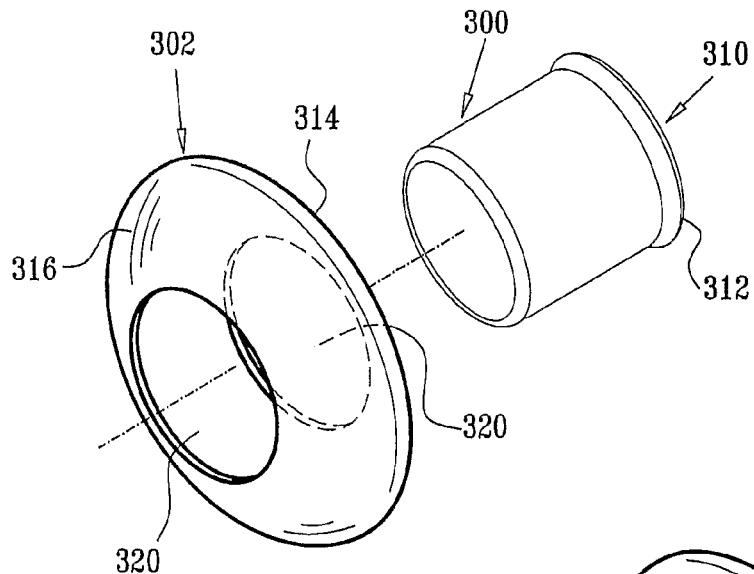
FIGS. 13A and 13B are simplified respective exploded and assembled pictorial illustrations of an injectable intraocular implant constructed and operative in accordance with yet another preferred embodiment of the present invention.
Figure 13B:
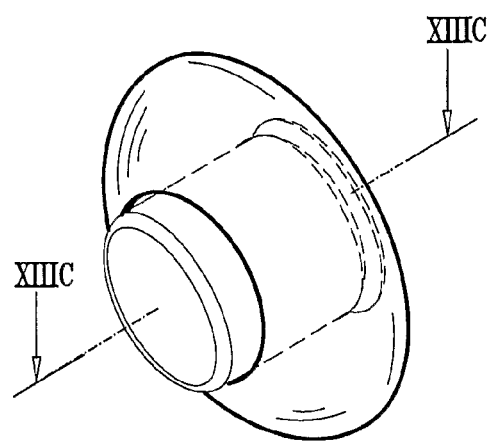
Figure 13C:
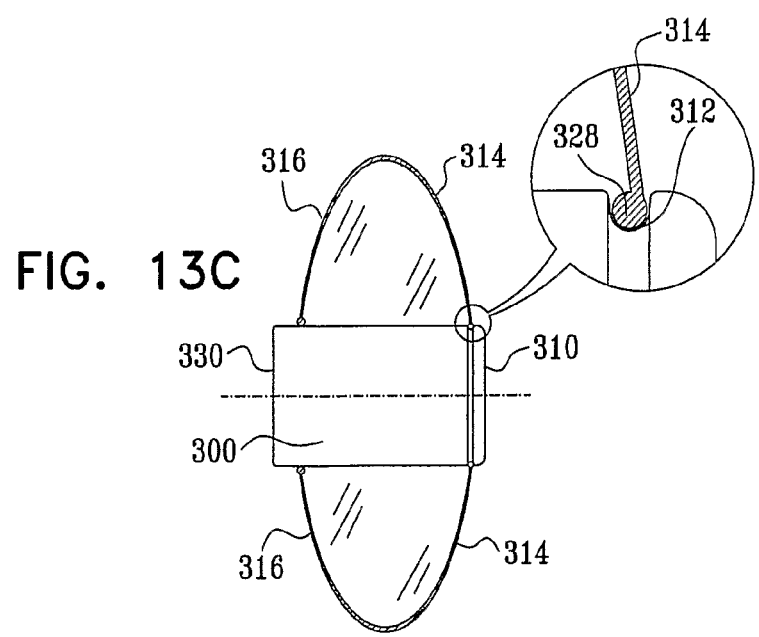
FIG. 13C is a simplified assembled side view illustration of the injectable intraocular implant of FIGS. 13A and 13B.

Reference is now made to FIGS. 13A-13C, which illustrate an injectable intraocular implant constructed and operative in accordance with yet another preferred embodiment of the present invention. It is seen that the implant preferably includes an optics portion 300 and a haptics portion 302 which is preferably snap-fitted onto the optics portion 300.

The optics portion 300 may be any suitable optics portion and is preferably, but not necessarily, a telescope. Preferred intraocular implants are described in applicants/assignee's published patent documents listed hereinbelow, the disclosures of which are hereby incorporated by reference:

U.S. Pat. Nos. 5,391,202; 5,354,335; 5,814,103; 5,876,442; 5,928,283; 6,007,579; 6,066,171; 6,569,199 and 6,596,026, and U.S. published applications U.S. Ser. Nos. 10/342,160 and 10/321,793.

The optics portion 300 may incorporate any one or more of the features described in the abovementioned patent documents in any suitable combination and is preferably in the form of a cylinder having adjacent one end thereof, hereinafter referred to as the inward facing end 310, a peripheral groove 312.

The haptics portion 302 is preferably formed of a resilient, flexible material, with a hollow, generally cylindrical structure defining a generally circular inward facing wall portion 314 and a generally circular outward facing wall portion 316. Each of wall portions 314 and 316 preferably define a generally circular optics engagement aperture 320 therein. Each of wall portions 314 and 316 is preferably formed with an inwardly directed peripheral protrusion 328 adjacent optics engagement aperture 320 thereof. Protrusion 328 of wall portion 314 is arranged for normally non-removable snap-fit engagement with groove 312 of optics portion 300, when haptics portion 302 is in coaxial surrounding relationship with optics portion 300 as shown.

Protrusion 328 of wall portion 316 is arranged for engagement of wall portion 316 with a delivery syringe as described further hereinbelow.

It is appreciated that while haptics portion 302 is preferably formed of a transparent material, it may be formed with non-transparent portions as suitable to eliminate and/or reduce glare.

Figure 14A:
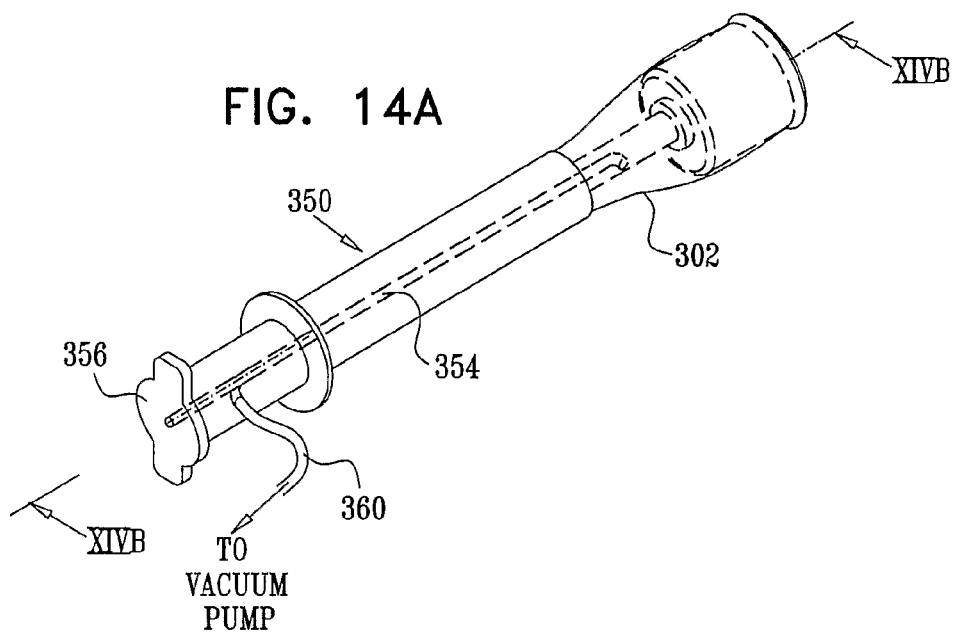
FIGS. 14A and 14B are simplified pictorial and sectional illustrations of the injectable intraocular implant of FIGS. 13A-13C located in a delivery syringe.
Figure 14B:
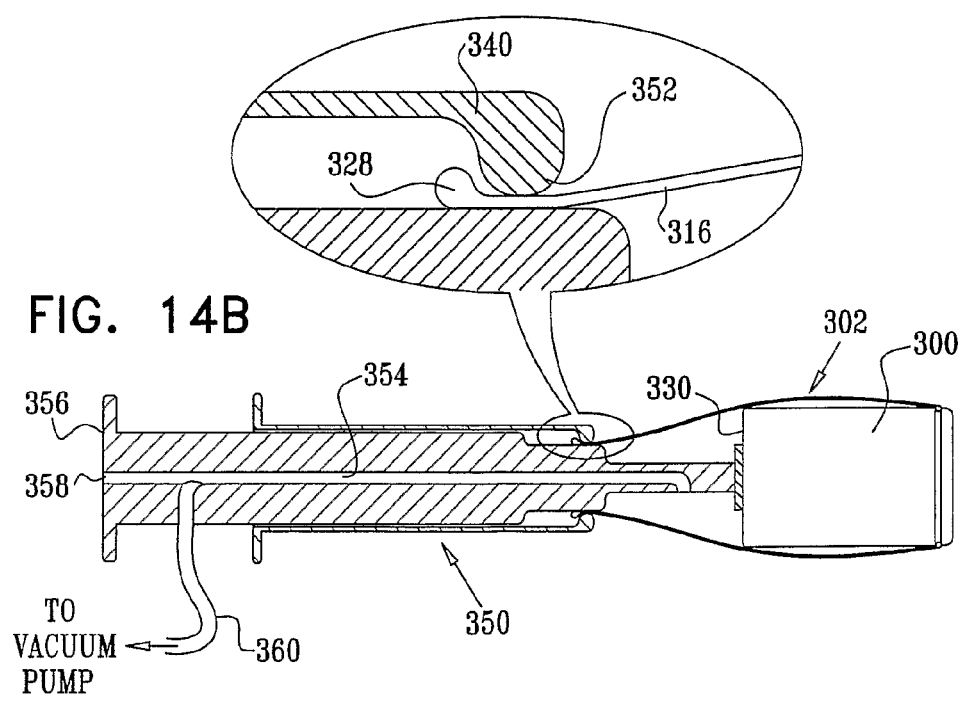

Reference is now made to FIGS. 14A and 14B, which are simplified pictorial and sectional illustrations of the injectable intraocular implant of FIGS. 13A-13C located in a delivery syringe and to FIGS. 15A, 15B, 15C and 15D, which are simplified sectional illustrations of four stages of the injection of the intraocular implant of FIGS. 13A-13C in the delivery syringe arrangement of FIGS. 14A and 14B into the eye of a patient.

As seen in FIGS. 14A-14B, prior to injection of the intraocular implant of FIGS. 13A-13C into an eye, outward facing wall portion 316 of haptics portion 302 is pulled over an outward facing end 330 of optics portion 300 and drawn into engagement with an outer wall 340 of a delivery syringe 350. As seen particularly in FIG. 14B, outer wall 340 preferably includes an inwardly directed peripheral protrusion 352 which engages protrusion 328 of wall portion 316 and thereby secures wall portion 316 of haptics portion 302 to delivery syringe 350. As seen further in FIGS. 14A-14B, the pulling of wall portion 316 causes haptics portion 302 to be temporarily deformed into an elongated generally cylindrical orientation overlying optics portion 300.

Delivery syringe 350 preferably also includes a fluid flow passageway 354 in fluid communication with a rearward facing wall 356 of syringe 350 at a location 358. Fluid flow passageway 354 is also preferably in fluid communication with a vacuum pump (not shown) via a tube 360.

Figure 15A:
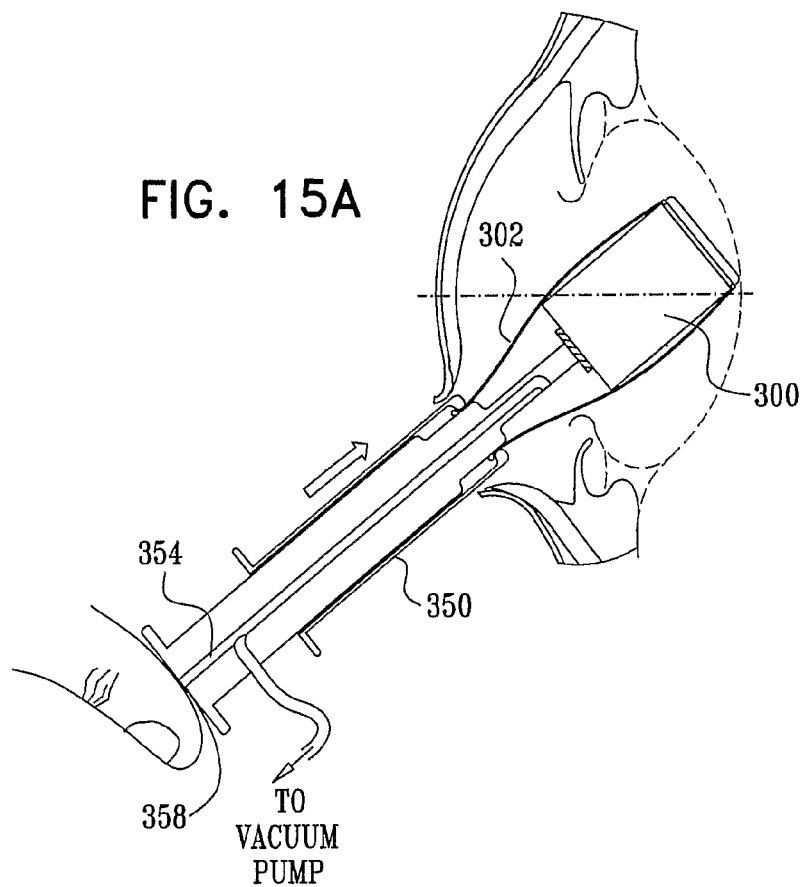
FIGS. 15A, 15B, 15C and 15D are simplified sectional illustrations of four stages of the injection of the intraocular implant of FIGS. 13A-13C in the delivery syringe arrangement of FIGS. 14A and 14B into the eye of a patient.

As seen in FIG. 15A, prior to insertion of the injectable intraocular implant into the lens capsule, fluid flow passageway 354 is temporarily sealed by covering location 358, and the vacuum pump is operated to remove air contained within haptics portion 302. FIG. 15A shows initial insertion of delivery syringe 350 into the lens capsule of the eye. It is appreciated that the operation of the vacuum pump allows haptics portion 302 to closely overly optics portion 300.

Figure 15B:
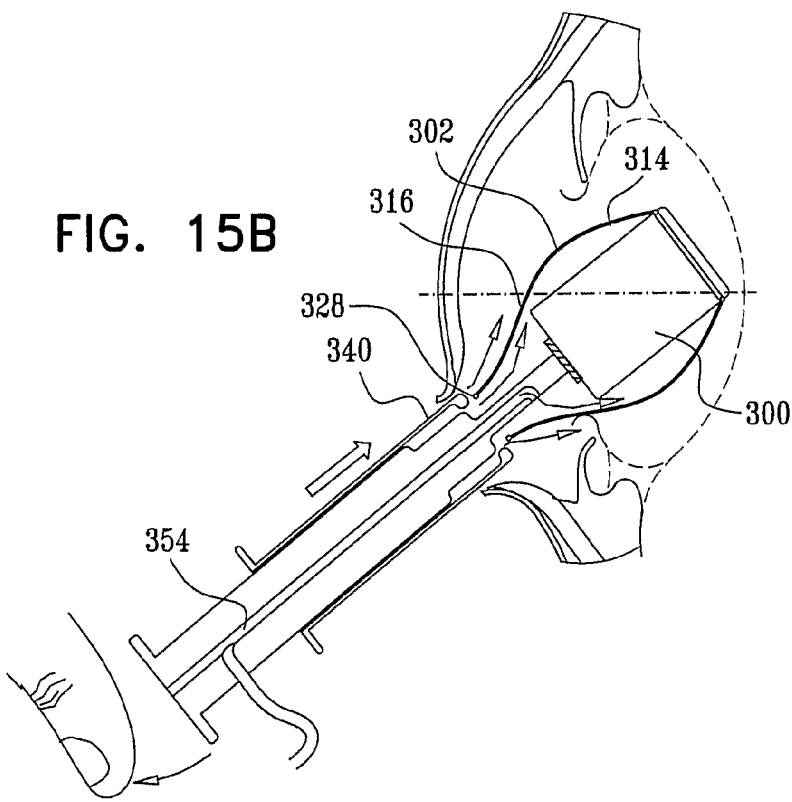
Figure 15C:
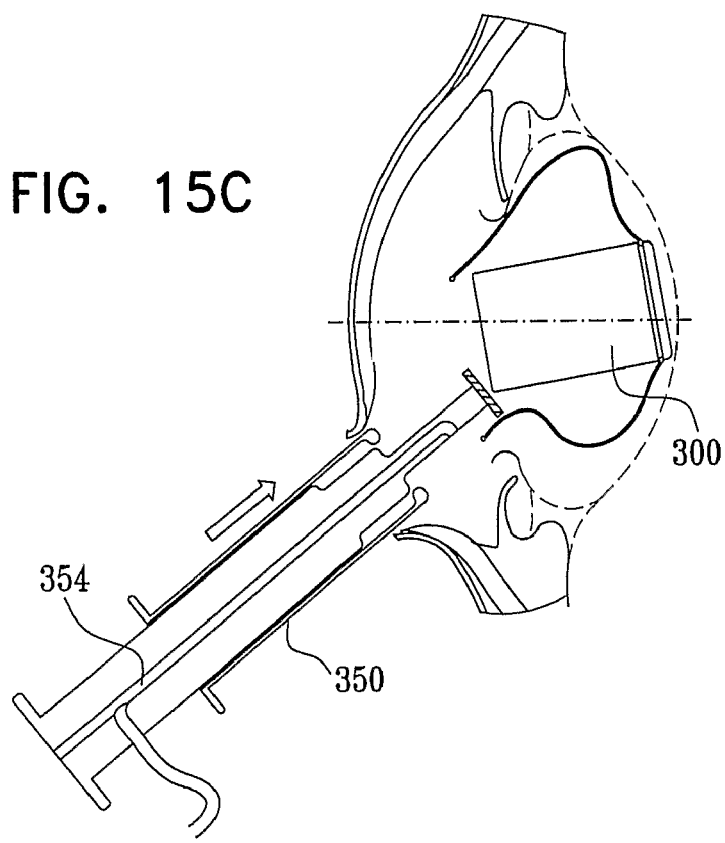

As seen further in FIGS. 15B-15C, following placement of the implant into the lens capsule, haptics portion 302 of the implant expands outwardly from the optics portion 300 as wall portions 314 and 316 of haptics portion 302 return to their original generally circular orientation. As seen in FIG. 15B, the unsealing of fluid flow passageway 354 allows air to flow therethrough and into the space formed between haptics portion 302 and optics portion 300, causing expansion of haptics portion 302 and causing outer wall 340 of delivery syringe 350 to disengage from protrusion 328 of wall portion 316 of haptics portion 302.

Figure 15D:
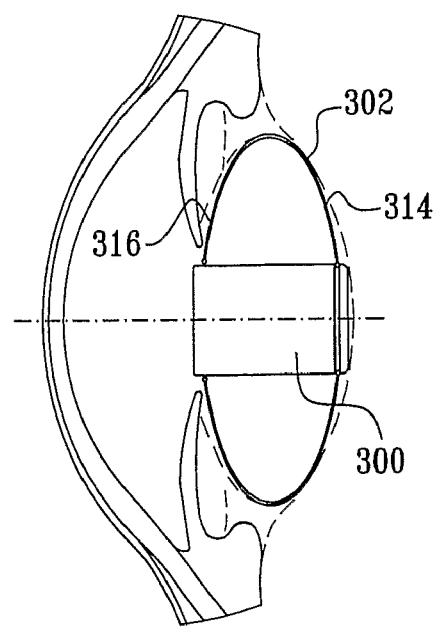

As seen in FIG. 15D, following the injection of haptics portion 302 and optics portion 300, delivery syringe 350 is removed from the eye and haptics portion 302 returns to its original form providing proper orientation of the implant, including fully deployed haptics portion 302 and optics portion 300, within the lens capsule.

Reference is now made to FIGS. 16A-16C, which illustrate an injectable intraocular implant constructed and operative in accordance with yet another preferred embodiment of the present invention. It is seen that the implant preferably includes an optics portion 400 and a haptics portion 402 which is preferably snap-fitted or shrink-fitted onto the optics portion 400.

The optics portion 400 may be any suitable optics portion and is preferably, but not necessarily, a telescope. Preferred intraocular implants are described in applicants/assignee's published patent documents listed hereinbelow, the disclosures of which are hereby incorporated by reference:

U.S. Pat. Nos. 5,391,202; 5,354,335; 5,814,103; 5,876,442; 5,928,283; 6,007,579; 6,066,171; 6,569,199 and 6,596,026, and U.S. published applications U.S. Ser. Nos. 10/342,160 and 10/321,793.

The optics portion 400 may incorporate any one or more of the features described in the abovementioned patent documents in any suitable combination and is preferably in the form of a cylinder having adjacent one end thereof, hereinafter referred to as the inward facing end 410, a peripheral groove 412.

The haptics portion 402 is preferably formed of a resilient, flexible material, with a hollow, generally cylindrical structure defining a generally circular inward facing wall portion 414 and a generally circular outward facing wall portion 416. Wall portion 414 preferably defines a generally circular optics engagement aperture 420 therein. Wall portion 414 is preferably formed with an inwardly directed peripheral protrusion 428 adjacent optics engagement aperture 420. Protrusion 428 of wall portion 414 is arranged for normally non-removable snap-fit or tension-fit engagement with groove 412 of optics portion 400, when haptics portion 402 is in coaxial surrounding relationship with optics portion 400 as shown.

It is appreciated that while haptics portion 402 is preferably formed of a transparent material, it may be formed with non-transparent portions as suitable to eliminate and/or reduce glare.

Figure 17A:
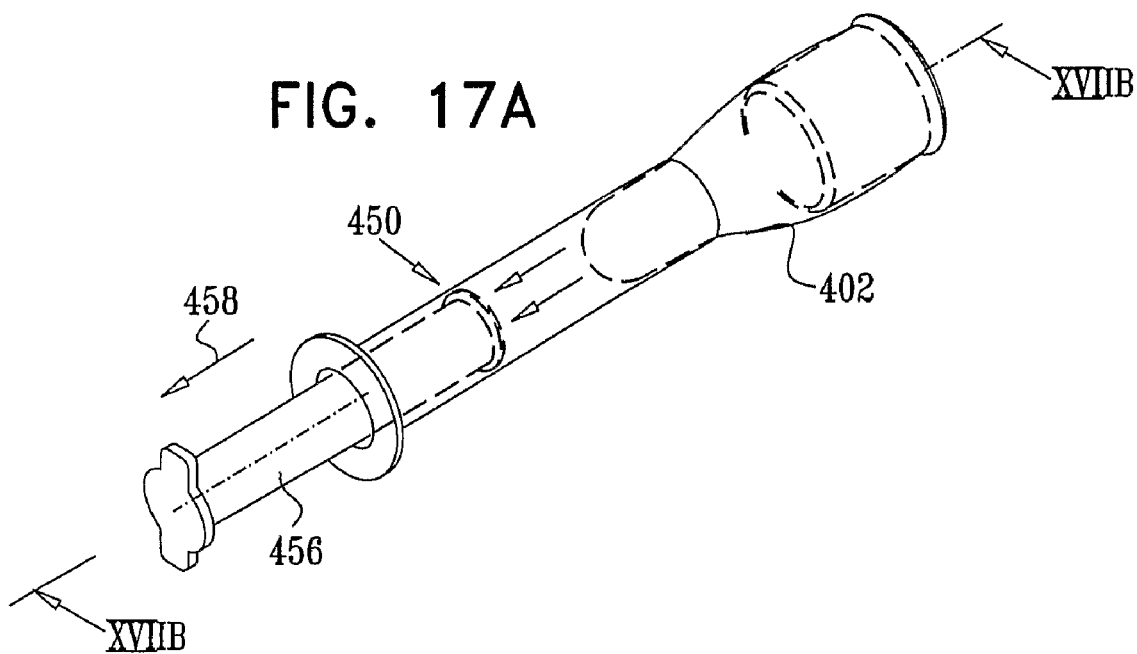
FIGS. 17A and 17B are simplified pictorial and sectional illustrations of the injectable intraocular implant of FIGS. 16A-16C located in a delivery syringe.
Figure 17B:
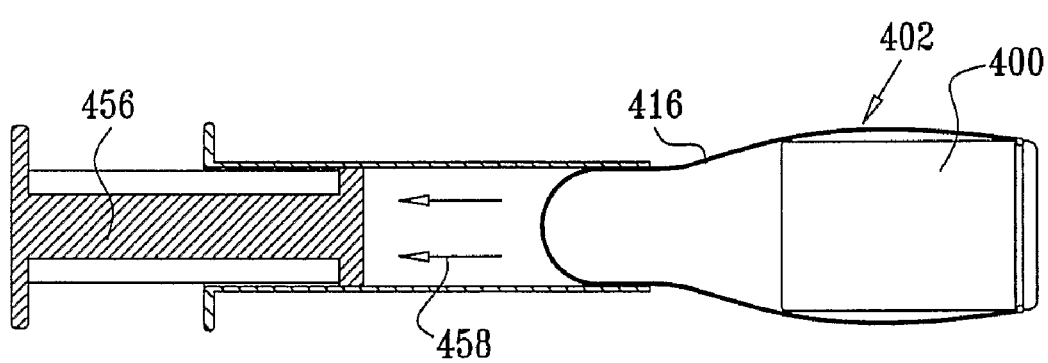

Reference is now made to FIGS. 17A and 17B, which are simplified pictorial and sectional illustrations of the injectable intraocular implant of FIGS. 16A-16C located in a delivery syringe and to FIGS. 18A, 18B, 18C and 18D, which are simplified sectional illustrations of four stages of the injection of the intraocular implant of FIGS. 16A-16C in the delivery syringe arrangement of FIGS. 17A and 17B into the eye of a patient.

As seen in FIGS. 17A-17B, prior to injection of the intraocular implant of FIGS. 16A-16C into an eye, outward facing wall portion 416 of haptics portion 402 is drawn into a vacuum delivery syringe 450 by extending a plunger 456 in the direction of arrow 458. As seen in FIGS. 17A-17B, the drawing of wall portion 416 into delivery syringe 450 causes haptics portion 402 to be temporarily deformed into an elongated generally cylindrical orientation overlying optics portion 400.

Figure 18A:
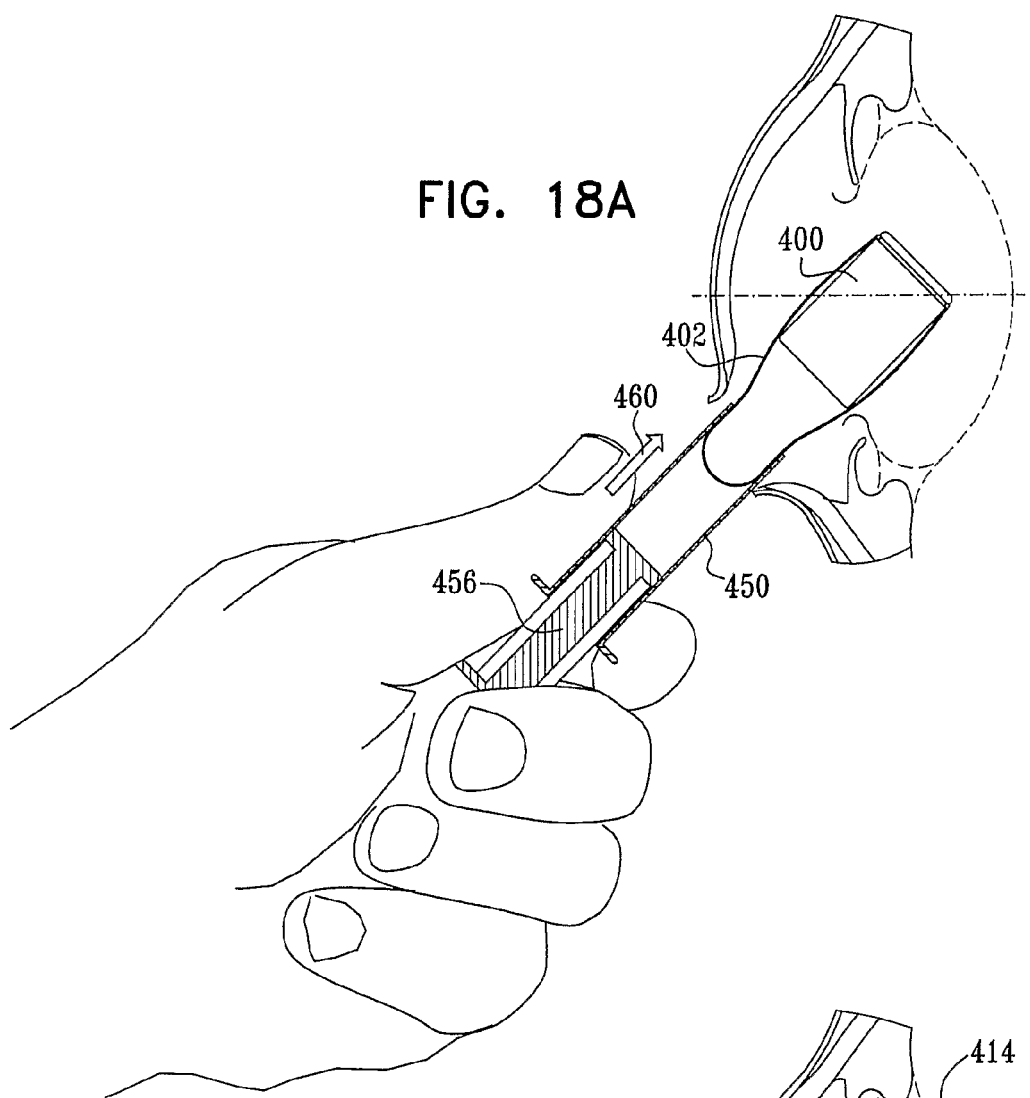
FIGS. 18A, 18B, 18C and 18D are simplified sectional illustrations of four stages of the injection of the intraocular implant of FIGS. 16A-16C in the delivery syringe arrangement of FIGS. 17A and 17B into the eye of a patient.

FIG. 18A shows initial insertion of delivery syringe 450 into the lens capsule of the eye, in the direction of arrow 460. It is appreciated that maintaining plunger 456 in the position of FIGS. 17A-17B maintains the vacuum inside delivery syringe 450 and allows haptics portion 402 to closely overly optics portion 400 during initial insertion of syringe 450 into the lens capsule.

Figure 18B:
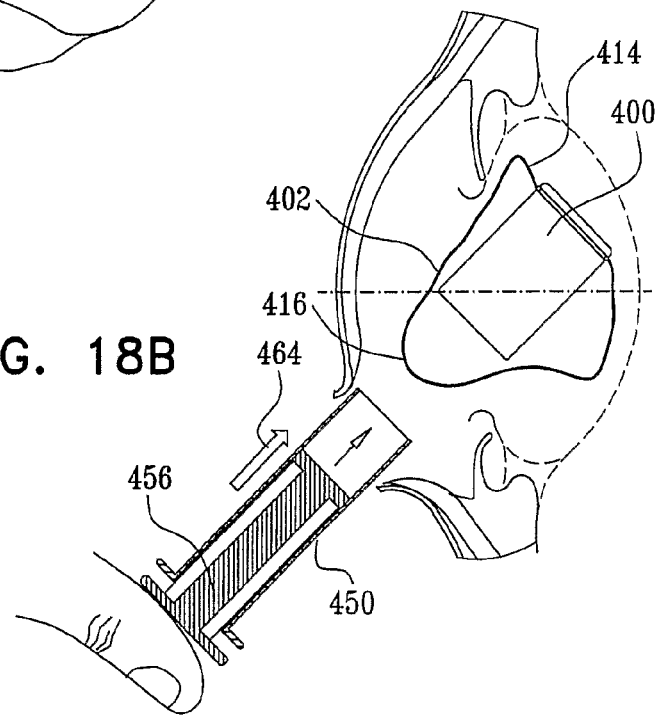

As seen further in FIG. 18B, following placement of the implant into the lens capsule, plunger 456 is pushed in the direction of arrow 464 and haptics portion 402 of the implant is released from syringe 450. Following release of the implant from delivery syringe 450, haptics portion 402 expands outwardly from the optics portion 400 as wall portions 414 and 416 of haptics portion 402 return to their original generally circular orientation.

Figure 18C:
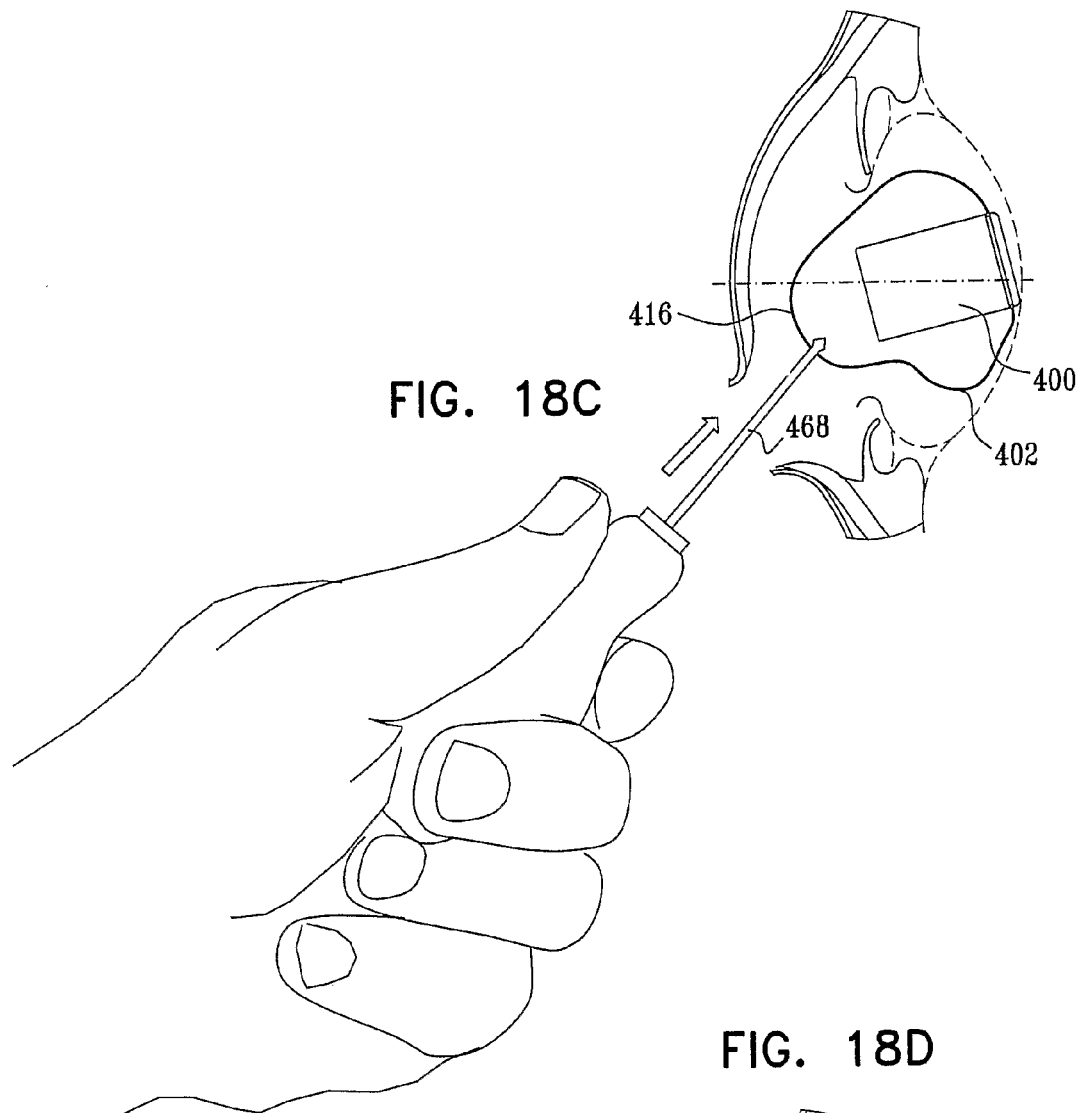
Figure 18D:
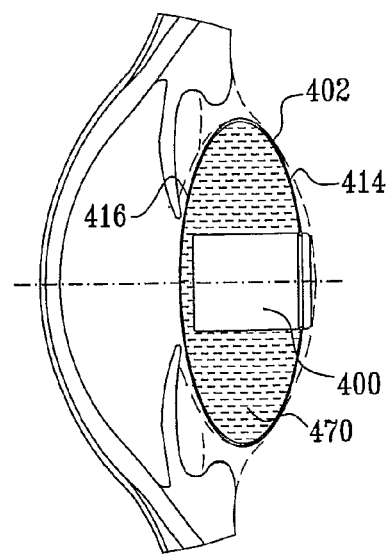

As seen further in FIG. 18C, following release of the implant and removal of delivery syringe 450, an aperture is made in wall portion 416, preferably through puncturing wall portion 416 with a hook 468, to allow aqueous fluid from the eye to flow into the area between optics portion 400 and haptics portion 402. As seen further in FIG. 18D, following the removal of hook 468, haptics portion 402 fills with aqueous fluid 470 and returns to its original form providing proper orientation of the implant, including fully deployed haptics portion 402 and optics portion 400, within the lens capsule.

Figure 19A:
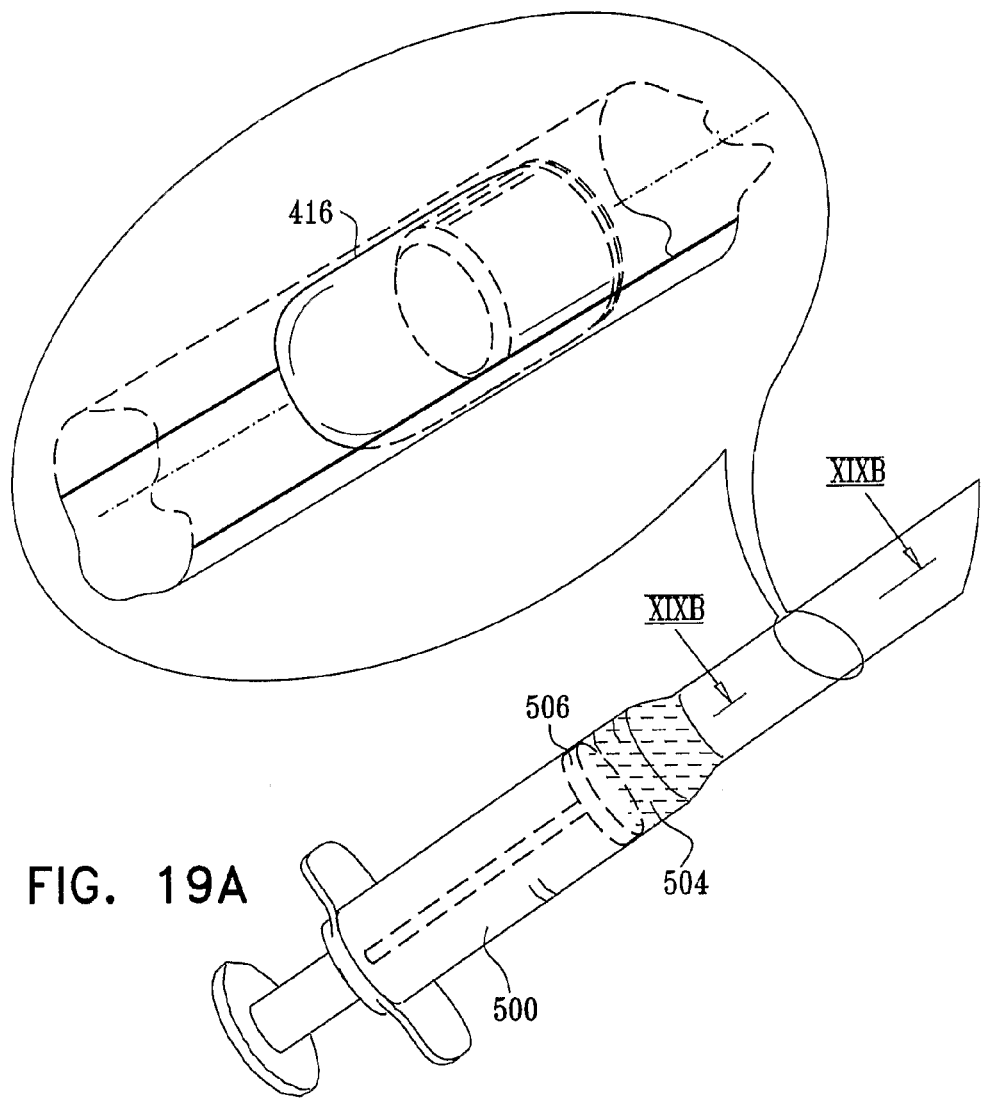
FIGS. 19A and 19B are simplified pictorial and sectional illustrations of the injectable intraocular implant of FIGS. 16A-16C located in a delivery syringe.
Figure 19B:
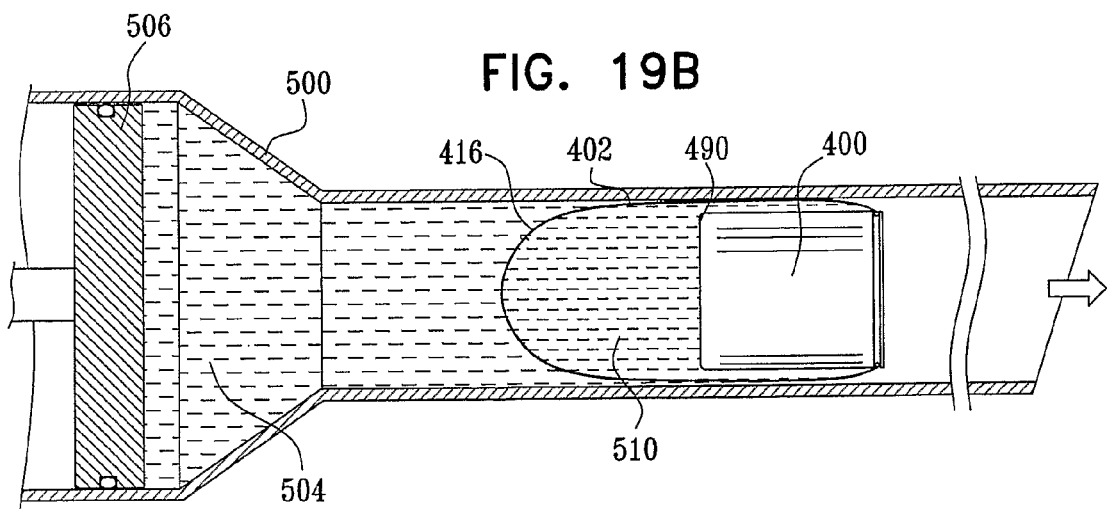

Reference is now made to FIGS. 19A and 19B, which are simplified pictorial and sectional illustrations of the injectable intraocular implant of FIGS. 16A-16C located in a fluid-filled delivery syringe and to FIGS. 20A, 20B, 20C and 20D, which are simplified sectional illustrations of four stages of the injection of the intraocular implant of FIGS. 16A-16C in the delivery syringe arrangement of FIGS. 19A and 19B into the eye of a patient.

As seen in FIGS. 19A-19B, prior to injection of the intraocular implant of FIGS. 16A-16C into an eye, outward facing wall portion 416 of haptics portion 402 is pulled over an outward facing end 490 of optics portion 400 and the intraocular implant is inserted into a fluid-filled delivery syringe 500. As seen in FIGS. 19A-19B, the pulling of wall portion 416 over end 490 causes haptics portion 402 to be temporarily deformed into an elongated generally cylindrical orientation overlying optics portion 400. Fluid, such as biocompatible fluid 504, is located forward of a piston 506 of delivery syringe 500 and rearward of the implant.

It is appreciated that haptics portion 402 may be filled, using any suitable method, with any suitable biocompatible fluid 510, such as saline or air, prior to insertion into delivery syringe 500. It is further appreciated that insertion of fluid 510 into haptics portion 402 provides cushioning for the intraocular implant during the injection thereof into an eye.

Figure 20A:
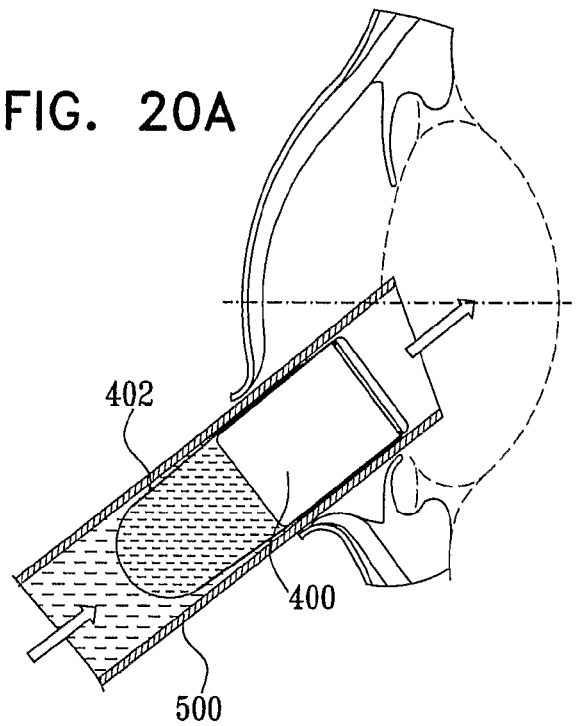
FIGS. 20A, 20B, 20C and 20D are simplified sectional illustrations of four stages of the injection of the intraocular implant of FIGS. 16A-16C in the delivery syringe arrangement of FIGS. 19A and 19B into the eye of a patient.

FIG. 20A shows initial insertion of the tip of delivery syringe 500 into the lens capsule of the eye. It is appreciated that the temporary deforming of haptics portion 402 allows haptics portion 402 to closely overly optics portion 400 inside syringe 500.

Figure 20B:
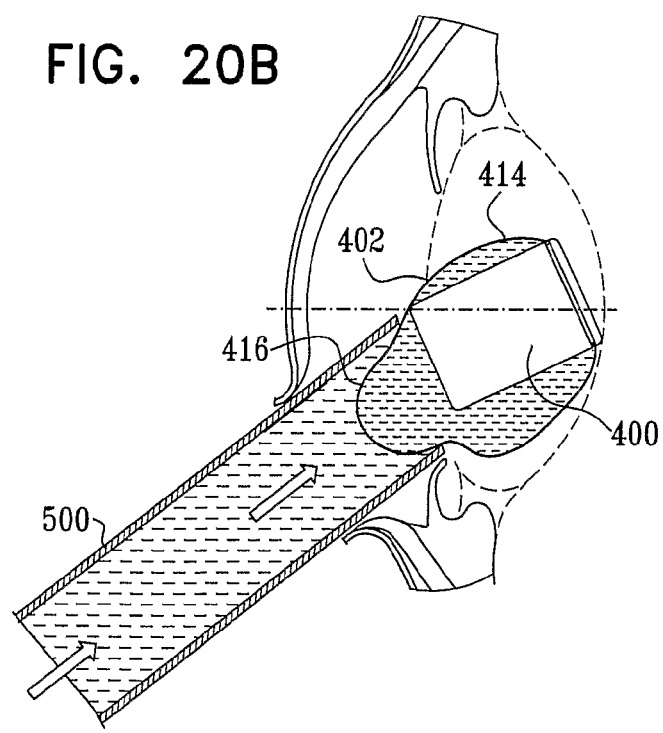

As seen further in FIG. 20B, following placement of the delivery syringe 500 into the lens capsule, the implant is forced out of the syringe 500 into the lens capsule. As seen in FIG. 20B, haptics portion 402 expands outwardly from the optics portion 400 as wall portions 414 and 416 of haptics portion 402 return to their generally circular orientation. Syringe 500 is subsequently removed from the lens capsule.

Figures 20C, 20D:
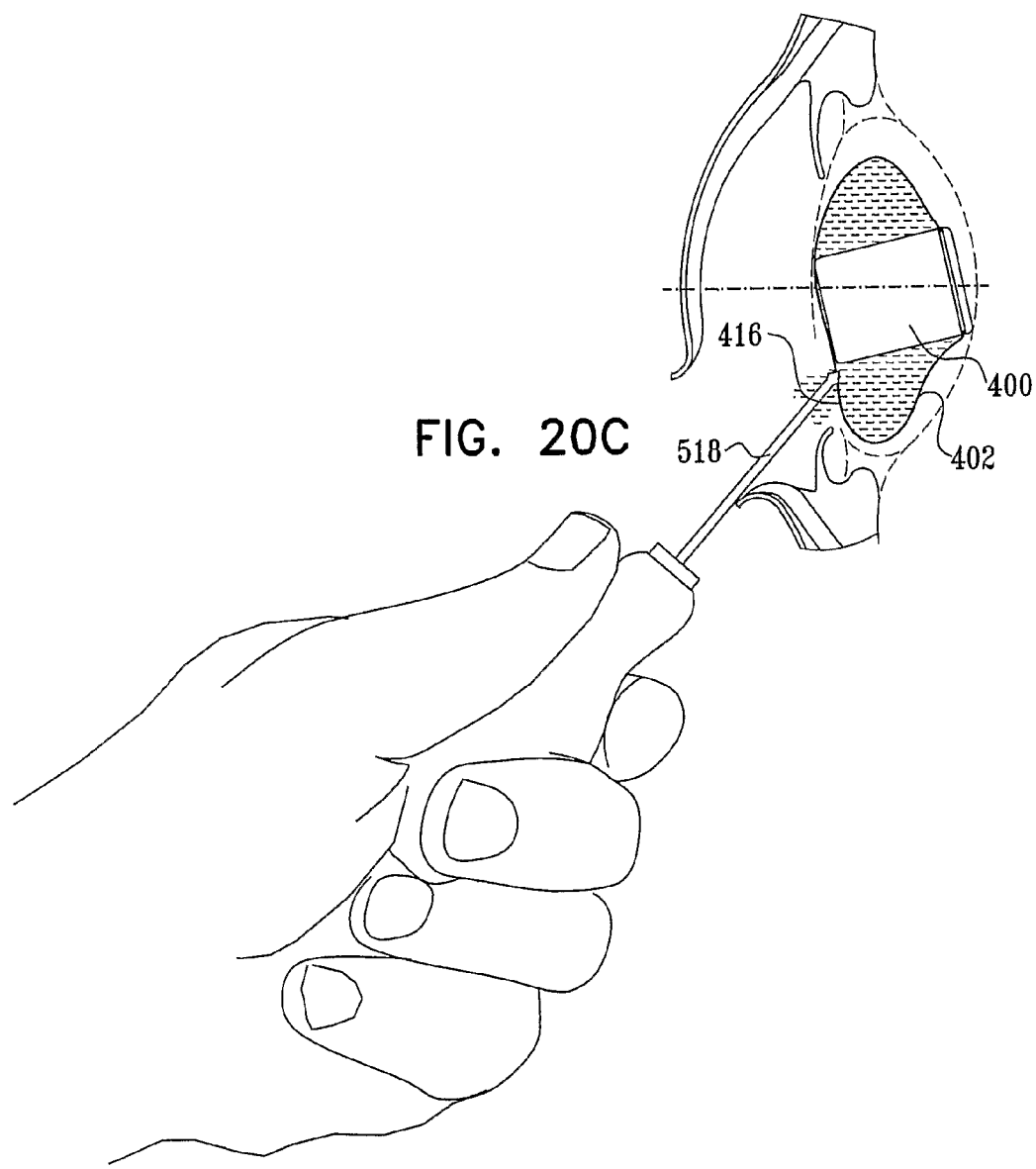

As seen further in FIG. 20C, an aperture is made in wall portion 416, preferably through puncturing wall portion 416 with a hook 518, to allow aqueous fluid from the eye to flow into the area between optics portion 400 and haptics portion 402 and mix with biocompatible fluid 510. Alternatively, haptics portion 402 is not filled with biocompatible fluid 510 prior to insertion into delivery syringe 500 and the puncturing of wall portion 416 allows aqueous fluid from the eye to flow into the area between optics portion 400 and haptics portion 402.

As seen further in FIG. 20D, following the removal of hook 518, haptics portion 402 returns to its original form providing proper orientation of the implant, including fully deployed haptics portion 402 and optics portion 400, within the lens capsule.

Reference is now made to FIGS. 21A and 21B, which are a simplified exploded view illustration and a simplified pictorial illustration of an injection assembly for an intraocular implant, constructed and operative in accordance with a further preferred embodiment of the present invention.

As seen in FIGS. 21A and 21B, the injection assembly preferably comprises a plunger 600 which cooperates with a syringe 610. Syringe 610 is movably located in a housing element 620, which is arranged along a longitudinal axis 622. An intraocular implant 630 is pre-positioned for injection by a positioning assembly including a rearward positioning element 640, which cooperates with syringe 610, and a forward positioning element 650. A compression spring 660 is seated between forward positioning element 650 and an intraocular implant displacer element 670 which engages a forward end of housing 620.

Reference is now made to FIGS. 22 and 23, which are, respectively, a simplified pictorial illustration and a simplified sectional illustration of plunger 600, forming part of the injection assembly of FIGS. 21A and 21B. Plunger 600 is preferably formed of a single piece of plastic, as by injection molding and includes a rearward axial portion 672, arranged along axis 622, which terminates in a generally disc-like engagement surface 674. Forward of rearward axial portion 672 there is provided a first disc-like plunger portion 676. Forward of plunger portion 676 and coaxial with rearward axial portion 672 is a forward axial portion 678, which terminates in a second, cylindrical plunger portion 680.

Reference is now made to FIGS. 24 and 25, which are, respectively, a simplified pictorial illustration and a simplified sectional illustration of syringe 610. Syringe 610 preferably includes a generally cylindrical rear portion 682, having an open rearward end 684 and opposite side apertures 686. Forward of cylindrical rear portion 682 is a tapered portion 688 which terminates in a generally cylindrical forward portion 690 having a sharpened and angled forward edge 692.

Forward portion 690 includes a rearward part 694, having a wall thickness similar to that of cylindrical rear portion 682, and a forward part 696, having a wall thickness substantially less than that of cylindrical rear portion 682 and being formed with opposite side apertures 698. Intermediate rear part 694 and forward part 696 there is provided a tapered ring part 700. Rearwardly of tapered ring part 700 finger engagement protrusions 702 extend from rear part 694.

As seen in FIG. 25, along an outer surface of forward part 696 there is preferably formed a shoulder 704, at which the outer diameter of the outer surface changes. The outer diameter of an outer surface forward of shoulder 704 is less than the outer diameter of the outer surface rearward of shoulder 704.

Figure 26:
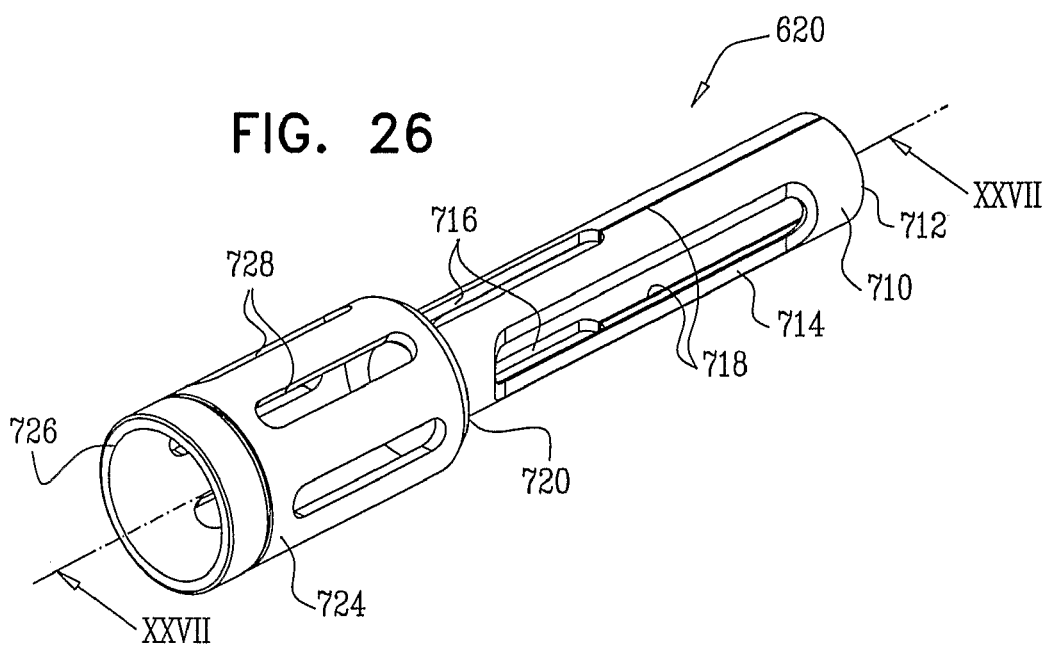
FIG. 26 is a simplified pictorial illustration of a housing element forming part of the injection assembly of FIGS. 21A and 21B.
Figure 27:
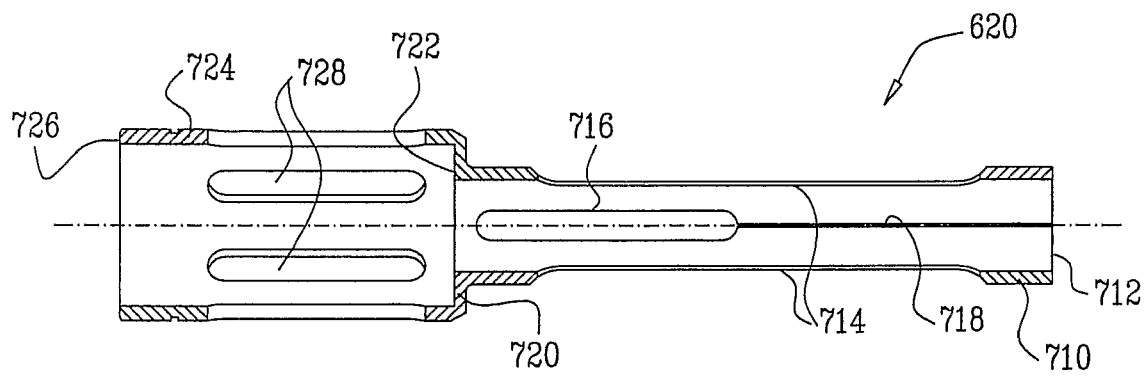
FIG. 27 is a simplified sectional illustration of the housing element of FIG. 26, taken along section lines XXVII-XXVII in FIG. 26.

Reference is now made to FIGS. 26 and 27, which are, respectively, a simplified pictorial illustration and a simplified sectional illustration of housing element 620. Housing element 620 preferably includes a generally cylindrical rear portion 710, having an open rearward end 712 and two pairs of opposite axially elongated side slots, respectively designated by reference numerals 714 and 716. Side slots 714 are preferably angularly offset by 90 degrees with respect to side slots 716. Side slots 716 are configured to slidably accommodate finger engagement protrusions 702 (FIGS. 24 and 25).

It is noted that generally cylindrical rear portion 710 is preferably formed of a resilient material, and is partially bifurcated along lines 718 to permit insertion thereinto of syringe 610.

Forward of cylindrical rear portion 710 and integrally joined thereto by a ring portion 720, defining a shoulder 722, is a generally cylindrical forward portion 724, having an open forward end 726 and being formed with multiple axially elongated slots 728.

Figure 28A:
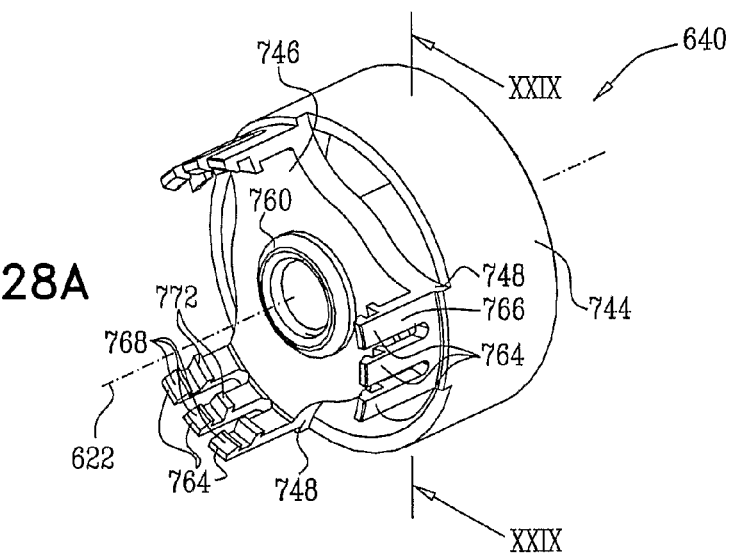
FIGS. 28A and 28B are simplified pictorial illustrations of a rearward positioning element forming part of the injection assembly of FIGS. 21A and 21B.
Figure 28B:
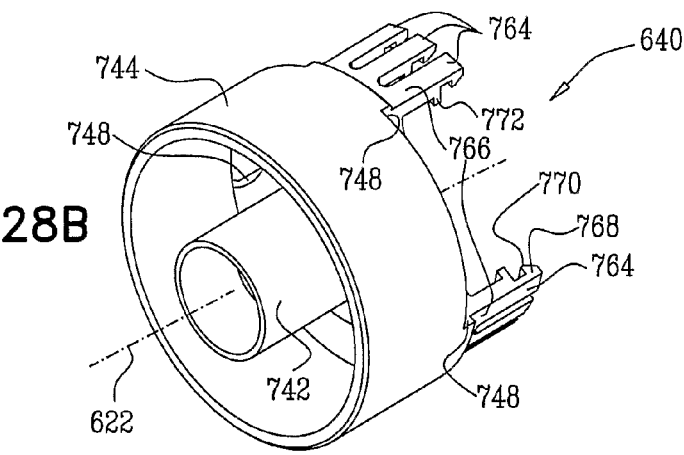
Figure 29:
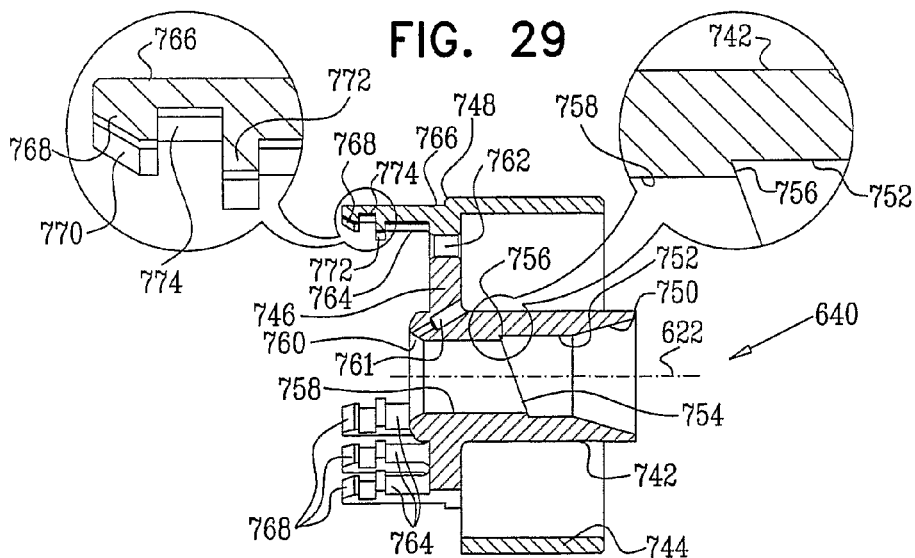
FIG. 29 is a simplified sectional illustration of the rearward positioning element of FIGS. 28A and 28B, taken along section lines XXIX-XXIX in FIG. 28A.

Reference is now made to FIGS. 28A, 28B and 29, which are, respectively, simplified pictorial illustrations and a simplified sectional illustration of rearward positioning element 640. The rearward positioning element 640 preferably comprises an inner generally cylindrical portion 742 and an outer generally cylindrical portion 744 which are joined by generally triangular-shaped portion 746, which engages the outer generally cylindrical portion 744 at three engagement locations 748 thereon.

The inner surface of inner generally cylindrical portion 742 includes a rearward facing tapered portion 750 which terminates forwardly in a generally cylindrical portion 752 having an angled forward edge 754 defining an angled shoulder 756. The angular orientation of angled shoulder 756 preferably is identical to that of edge 692 of syringe 610 (FIGS. 24 and 25).

Forward of angled shoulder 756 is a generally cylindrical portion 758 having a diameter which is less than the diameter of generally cylindrical portion 752. Disposed forwardly of generally cylindrical portion 758 is a tapered portion 760, which protrudes slightly forwardly from generally triangular-shaped portion 746. A lubrication bore 761 extends diagonally through cylindrical portion 758 and tapered portion 760.

An azimuthal registration aperture 762 is preferably formed in generally triangular-shaped portion 746 adjacent one of engagement locations 748.

Arranged at each of engagement locations 748 there are formed a plurality of snap-fit engagement elements 764, typically three in number, which extend parallel to axis 622. Each of snap-fit engagement elements 764 preferably has a smooth radially outwardly facing surface 766 which as seen in FIG. 29 is slightly recessed inwardly with respect to the outer surface of outer generally cylindrical portion 744. Each of snap-fit engagement elements 764 terminates in a radially inwardly directed protrusion 768 which has a radially inward facing tapered surface 770. Rearwardly of protrusion 768 and axially spaced therefrom is a radially inwardly directed protrusion 772, which extends radially inwardly to an extent greater than protrusion 768 and defines, together with protrusion 768, an undercut recess 774. Alternatively, protrusions 768 and 772 of snap-fit engagement elements may be radially outwardly directed.

Figure 30A:
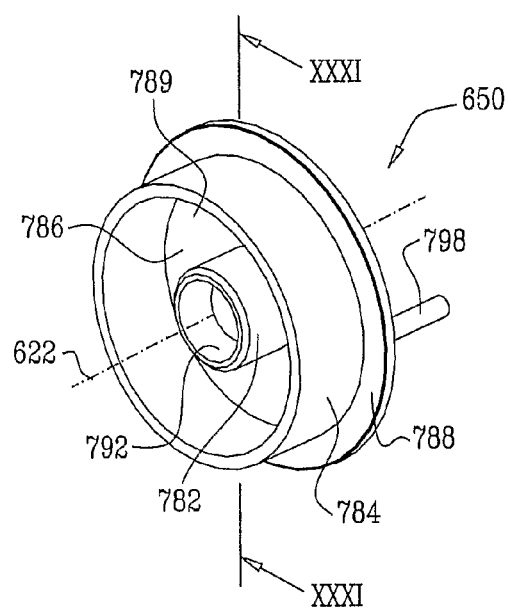
FIGS. 30A and 30B are simplified pictorial illustrations of a forward positioning element forming part of the injection assembly of FIGS. 21A and 21B.
Figure 30B:
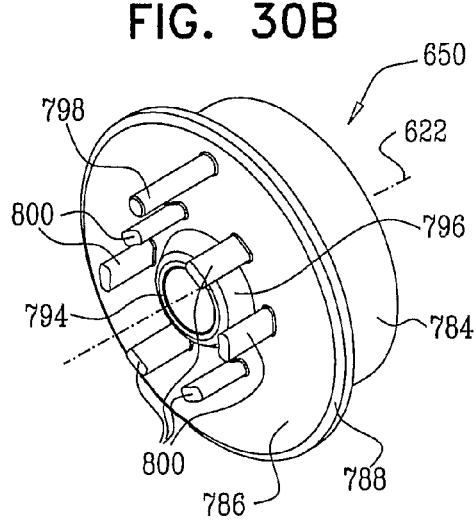
Figure 31:
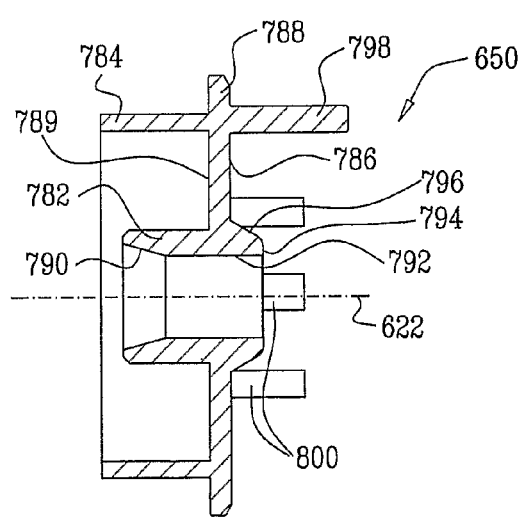
FIG. 31 is a simplified sectional illustration of the forward positioning element of FIGS. 30A and 30B, taken along section lines XXXI-XXXI in FIG. 30A.

Reference is now made to FIGS. 30A, 30B and 31, which are, respectively, simplified pictorial illustrations and a simplified sectional illustration of forward positioning element 650. The forward positioning element 650 preferably comprises an inner generally cylindrical portion 782 and an outer generally cylindrical portion 784 which are joined by a generally ring-shaped portion 786, which extends radially outwardly beyond outer generally cylindrical portion 784 to define a snap-fit engagement flange 788 which is configured for snap fit engagement with recesses 774 of rearward positioning element 640 (FIGS. 28A, 28B and 29). A spring seat for compression spring 660 is defined between inner generally cylindrical portion 782 and outer generally cylindrical portion 784 by a forwardly-facing surface 789 of generally ring-shaped portion 786.

The inner surface of inner generally cylindrical portion 782 includes a forward facing tapered portion 790 which terminates rearwardly in a generally cylindrical portion 792. A rearward edge 794 of generally cylindrical portion 792 has a tapered outer surface 796. An azimuthal registration pin 798 extends rearwardly of ring-shaped portion 786 and is configured to engage azimuthal registration aperture 762 of rearward positioning element 640 (FIGS. 28A, 28B and 29).

Rearwardly facing haptics positioning protrusions 800 also extend rearwardly from ring-shaped portion 786.

Figure 32A:
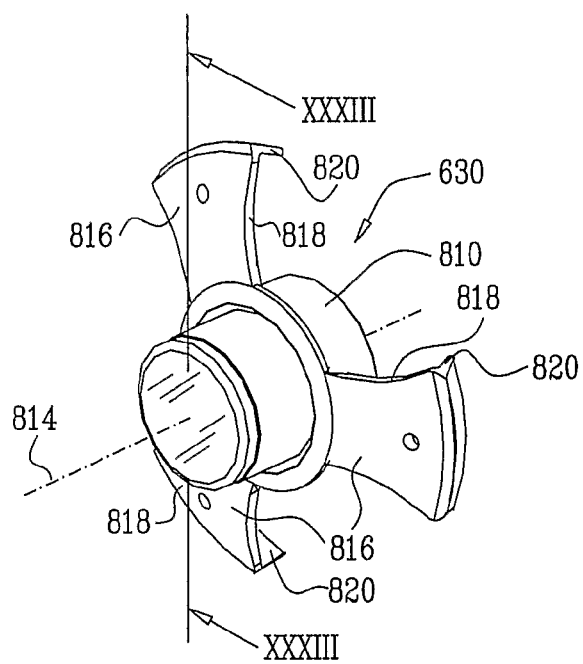
FIGS. 32A and 32B are simplified pictorial illustrations of an injectable intraocular implant forming part of the injection assembly of FIGS. 21A and 21B.
Figure 32B:
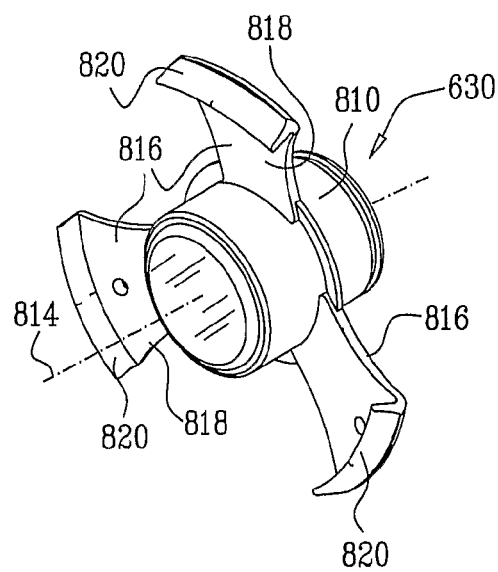
Figure 33:
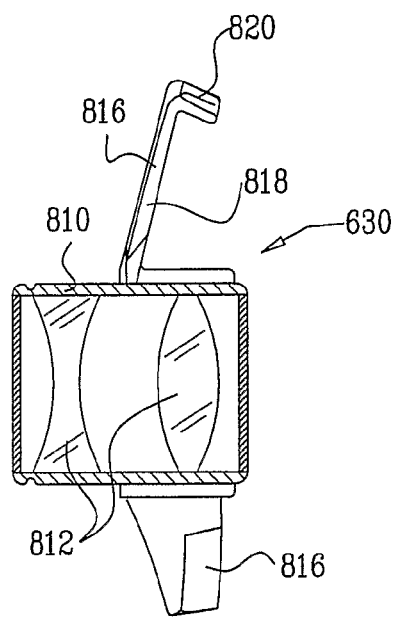
FIG. 33 is a simplified sectional illustration of the injectable intraocular implant of FIGS. 32A and 32B, taken along section lines XXXIII-XXXIII in FIG. 32A.

Reference is now made to FIGS. 32A, 32B and 33, which are, respectively, simplified pictorial illustrations and a simplified sectional illustration of injectable intraocular implant 630. The intraocular implant 630 may be constructed and operative in accordance with any suitable optical design and preferably incorporates the teachings of one or more of applicant/assignee's intraocular implants as described in U.S. Pat. Nos. 5,391,202; 5,354,335; 5,814,103; 5,876,442; 5,928,283; 6,007,579; 6,066,171; 6,569,199 and 6,596,026, and U.S. published applications U.S. Ser. Nos. 10/342,160 and 10/321,793, the disclosures of which are hereby incorporated by reference.

The injectable intraocular implant 630 preferably includes a generally cylindrical sealed capsule 810 containing one or more lenses 812 having an optical axis 814. Haptics 816 extend generally radially outwardly from capsule 810 and preferably include a generally resilient rearwardly slanted portion 818, terminating in a rearwardly- and inwardly-directed tapered portion 820.

It is appreciated that the haptics 816 are preferably formed of a material which allows passage of light through the haptics 816 at a level which is similar to the level of passage of light through the capsule 810.

Figure 34A:
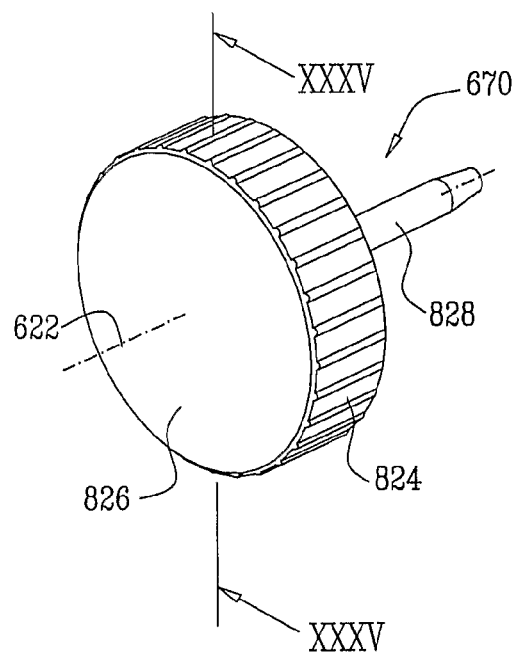
FIGS. 34A and 34B are simplified pictorial illustrations of an intraocular implant displacer element forming part of the injection assembly of FIGS. 21A and 21B.
Figure 34B:
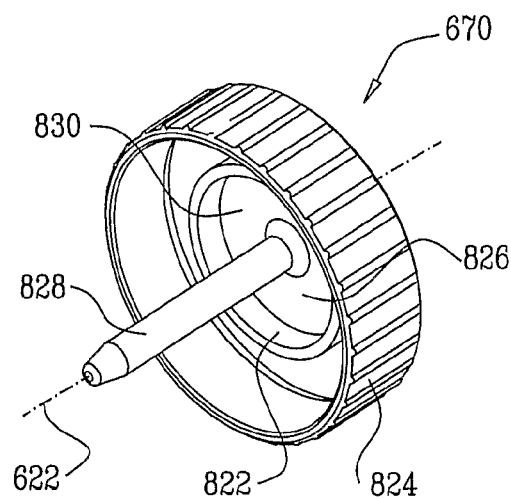
Figure 35:
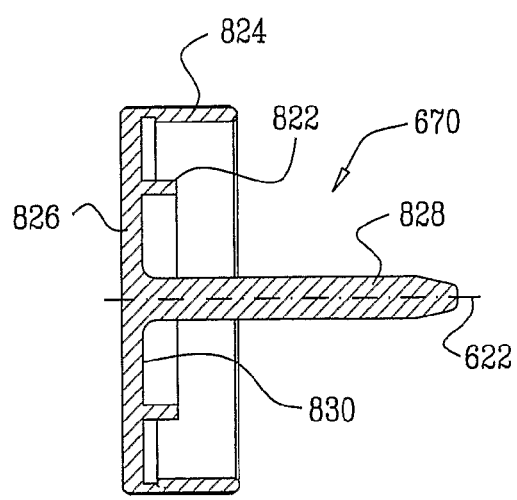
FIG. 35 is a simplified sectional illustration of the intraocular implant displacer element of FIGS. 34A and 34B, taken along section lines XXXV-XXXV in FIG. 34A.

Reference is now made to FIGS. 34A, 34B and 35, which are, respectively, simplified pictorial illustrations and a simplified sectional illustration of intraocular implant displacer element 670. The intraocular implant displacer element 670 preferably comprises an inner generally cylindrical portion 822 and an outer generally cylindrical portion 824 which are joined by a generally disc-shaped portion 826. A central shaft 828 extends rearwardly from generally disc-shaped portion 826 along axis 622. A spring seat for compression spring 660 is defined between shaft 828 and inner generally cylindrical portion 822 by a rearwardly-facing surface 830 of generally disc-shaped portion 826.

Figure 36:
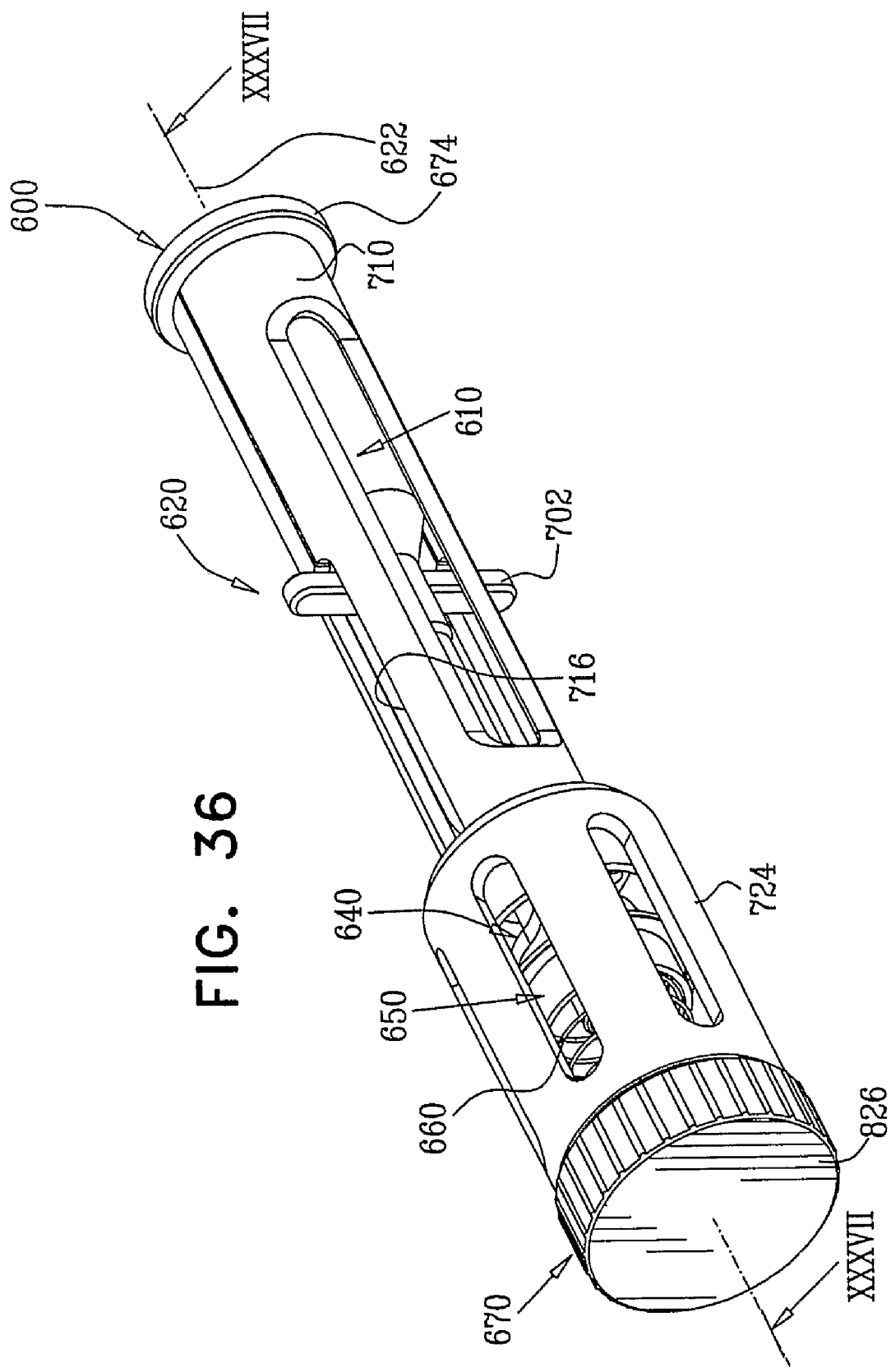
FIG. 36 is a simplified pictorial illustration of the injection assembly of FIGS. 21A and 21B in a storage orientation.
Figure 37:
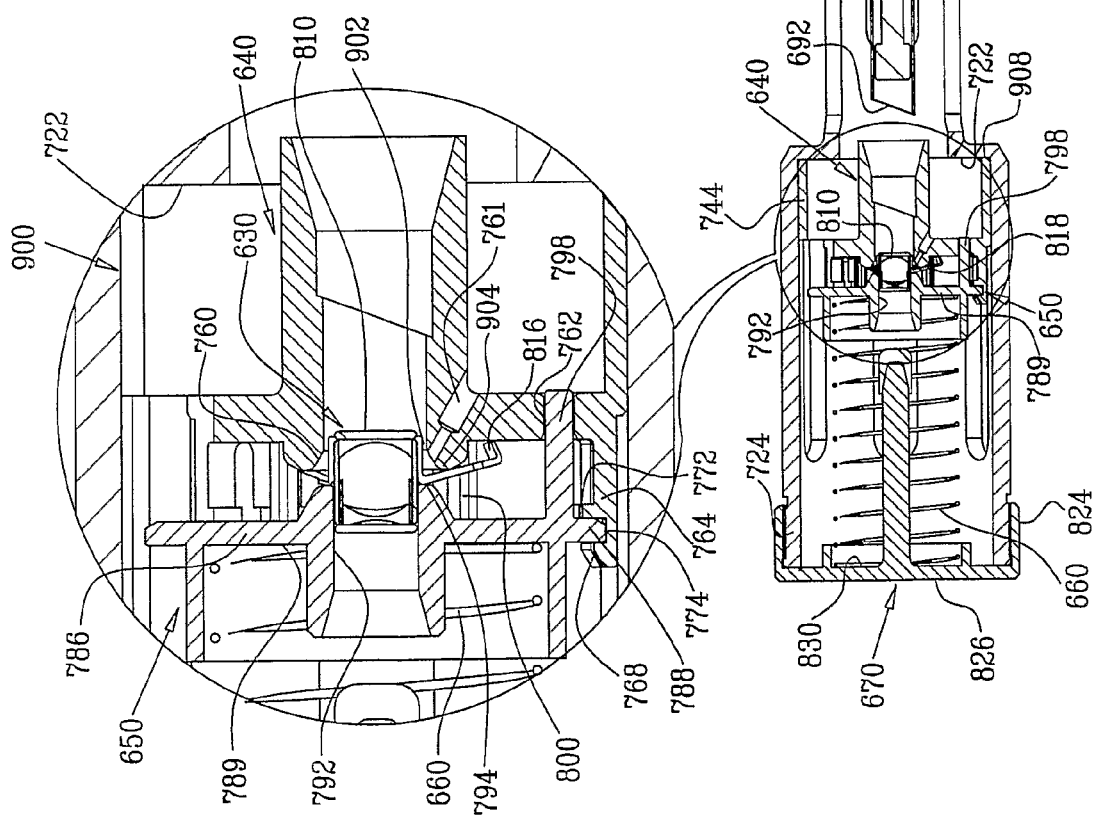
FIG. 37 is a simplified sectional illustration of the injection assembly of FIG. 36, taken along section lines XXXVII-XXXVII in FIG. 36.

Reference is now made to FIGS. 36 and 37, which are simplified pictorial and sectional illustrations of the injection assembly of FIGS. 21A and 21B in a storage orientation. Disposed in forward portion 724 of housing 620 is an intraocular implant mounting subassembly 900, including rearward positioning element 640 and forward positioning element 650 which together retain intraocular implant 630 in a desired orientation for injection into the eye.

As seen in the enlarged portion of FIG. 37, snap fit engagement elements 764 of rearward positioning element 640 lockingly engage flange 788 of forward positioning element 650. Flange 788 is lockingly engaged in undercut recess 774 of rearward positioning element 640, by protrusions 768 and 772 of rearward positioning element 640.

Relative rotation of rearward positioning element 640 and forward positioning element 650 is prevented by engagement of azimuthal registration pin 798 with azimuthal registration aperture 762.

Haptics 816 of intraocular implant 630 are retained between respective forward and rearward positioning elements 650 and 640. As seen, a radially inward end 902 of slanted portion 818 lies axially rearward of rearward edge 794 of forward positioning element 650 and a rearward facing intermediate part of slanted portion 818 lies against a forward edge 904 of rearward positioning element 640.

Capsule 810 of intraocular implant 630 lies within cylindrical portion 792 of forward positioning element 650 and extends rearwardly of tapered portion 760 of rearward positioning element 640. Desired azimuthal orientation of the intraocular implant 630 is maintained by location of the haptics 816 between haptics positioning protrusions 800.

A rearward facing edge 908 of outer generally cylindrical portion 744 of rearward positioning element 640 is urged against shoulder 722 of housing element 620 by compression spring 660, a rearward facing end of which is seated against forwardly facing surface 789 of ring shaped portion 786 of forward positioning element 650. A forward facing end of spring 660 is seated against rearwardly facing surface 830 of disc-shaped portion 826 of intraocular implant displacer element 670, which is preferably threaded onto cylindrical portion 724 of housing element 620 by engagement of outer generally cylindrical portion 824 of intraocular implant displacer element 670 with an outer surface of cylindrical portion 724 of housing element 620.

Syringe 610 is disposed within generally cylindrical rear portion 710 of housing element 620 and is arranged such that finger engagement protrusions 702 are slidably accommodated in side slots 716. In the storage orientation shown in FIGS. 36 and 37, the finger engagement protrusions 702 are fully retracted and thus lie against a rearward edge of side slots 716. As seen, engagement surface 674 of plunger 600 engages rearward end 712 of housing element 620.

It is a particular feature of the present invention that angled forward edge 754 of rearward positioning element 640, together with sharpened and angled edge 692 of syringe 610, azimuthal registration aperture 762 and azimuthal registration pin 798, are operative to provide predetermined azimuthal alignment between the intraocular implant 630, rearward positioning element 640, forward positioning element 650 and syringe 610, such that when intraocular implant 630 is injected from syringe 610 into the eye, one of haptics 816 will be aligned with the shorter portion of sharpened and angled edge 692 of syringe 610, as described hereinbelow with reference to FIGS. 48A-48D.

At this stage, a user preferably provides a viscoelastic lubricant into the rearward positioning element 640 via lubrication bore 761. The viscoelastic lubricant preferably lubricates external surfaces of intraocular implant 630 during the injection process described hereinbelow with reference to FIGS. 38-48D.

Figure 38:
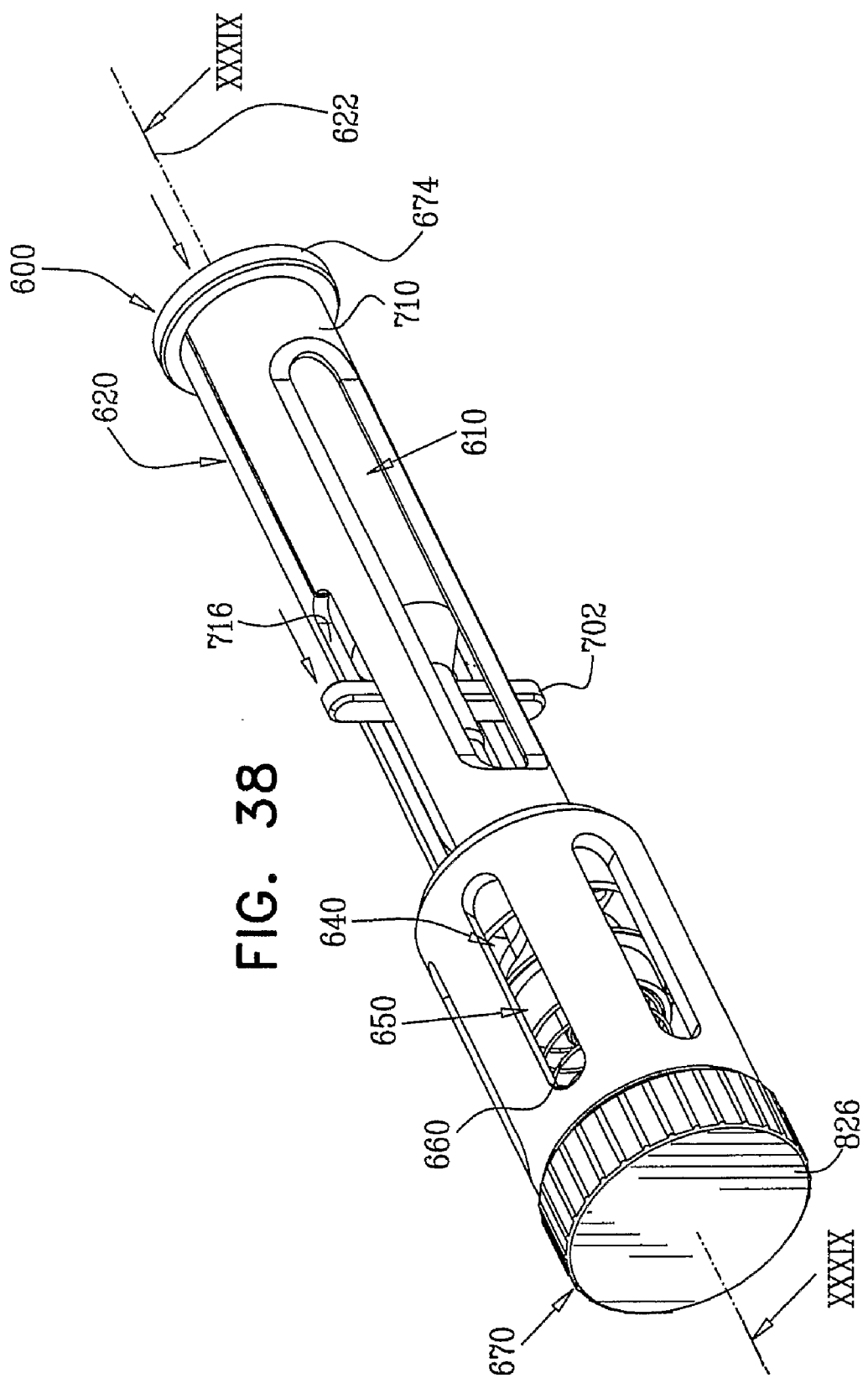
FIG. 38 is a simplified pictorial illustration of the injection assembly of FIGS. 36 and 37 in an intraocular implant pre-loading orientation.

Reference is now made to FIGS. 38 and 39, which are simplified pictorial and sectional illustrations of the injection assembly of FIGS. 36 and 37 in an intraocular implant pre-loading orientation. The injection assembly in its storage orientation as seen in FIGS. 36 and 37 is brought to the pre-loading orientation of FIGS. 38 and 39 by action of a user, pushing the finger engagement protrusions 702 of syringe 610 forwardly along axis 622, thereby forwardly displacing the syringe 610 with respect to housing element 620 and the plunger 600.

The forward displacement of syringe 610 along axis 622 preferably is stopped by engagement of sharpened and angled forward edge 692 of syringe 610 with angled shoulder 756 of rearward positioning element 640.

Figure 40:
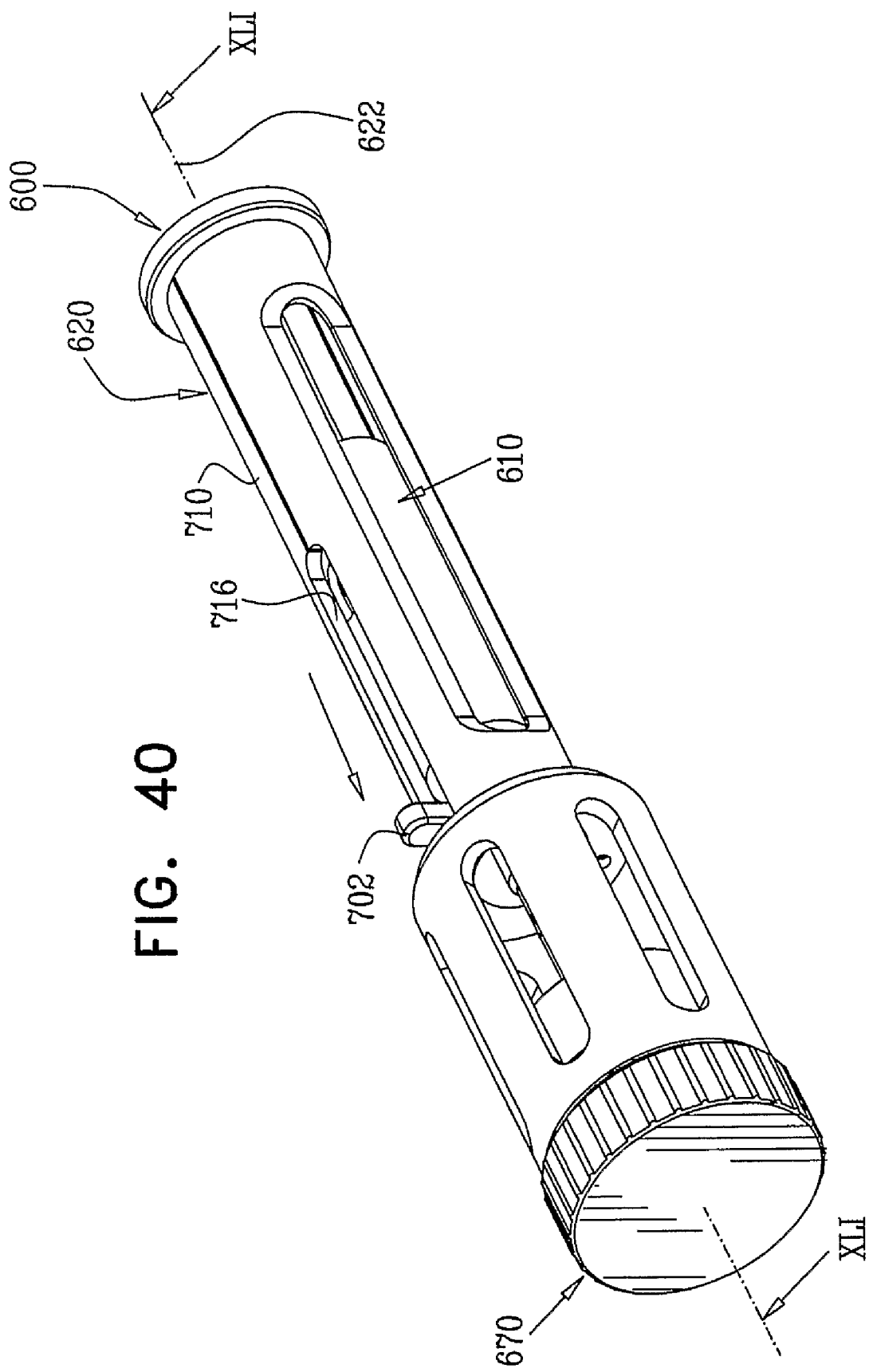
FIG. 40 is a simplified pictorial illustration of the injection assembly of FIGS. 38 and 39 in an intraocular implant loading orientation.

Reference is now made to FIGS. 40 and 41, which are simplified pictorial and sectional illustrations of the injection assembly of FIGS. 38 and 39 in an intraocular implant loading orientation. The injection assembly in its intraocular implant pre-loading orientation, as seen in FIGS. 38 and 39, is brought to the intraocular implant loading orientation of FIGS. 40 and 41 by continuing action of the user, pushing the finger engagement protrusions 702 of syringe 610 forwardly, thereby further forwardly displacing the syringe 610 along axis 622 with respect to housing element 620 and plunger 600. As shown, the finger engagement protrusions 702 preferably lie against a forward edge of side slots 716.

Due to the engagement between sharpened and angled forward edge 692 of syringe 610 and angled shoulder 756 of rearward positioning element 640, forward displacement of syringe 610 results in forward displacement of rearward positioning element 640 with respect to housing element 620. The locking engagement between rearward positioning element 640 and forward positioning element 650, which together support intraocular implant 630 in a predetermined orientation, causes forward positioning element 650 and intraocular implant 630 to be forwardly displaced along axis 622 by rearward positioning element 640 with respect to housing element 620 against the urging of compression spring 660.

Forward displacement along axis 622 of rearward positioning element 640, together with forward positioning element 650 and intraocular implant 630 causes shaft 828 of intraocular implant displacer element 670 to engage a forward facing edge 910 of capsule 810 of intraocular implant 630. Shaft 828 is preferably covered by a cap portion which does not harm the capsule 810 when engaged therewith.

Continued forward displacement along axis 622 of forward and rearward positioning elements 650 and 640 and intraocular implant 630 with respect to intraocular implant displacer element 670 results in intraocular implant 630 being displaced rearwardly by shaft 828, with respect to forward and rearward positioning elements 650 and 640, into the interior of forward part 696 of forward portion 690 of syringe 610.

As seen with particular clarity in the enlarged portion of FIG. 41, the intraocular implant 630 is oriented within the interior of forward part 696 of forward portion 690 such that haptics 816 are folded over capsule 810 and extend forwardly thereof.

It is a particular feature of the present invention that the mechanical integrity of haptics 816 of intraocular implant 630 is maintained during loading thereof into syringe 610 by the particular configuration of the haptics 816 within subassembly 900. When capsule 810 is pushed rearwardly along axis 622 with respect to forward and rearward positioning elements 650 and 640 by shaft 828, slanted portions 818 (FIGS. 32A-33) of haptics 816 slide along and between tapered outer surface 796 of forward positioning element 650 and tapered portion 760 of rearward positioning element 640, and thus extend forwardly alongside capsule 810.

Figure 42:
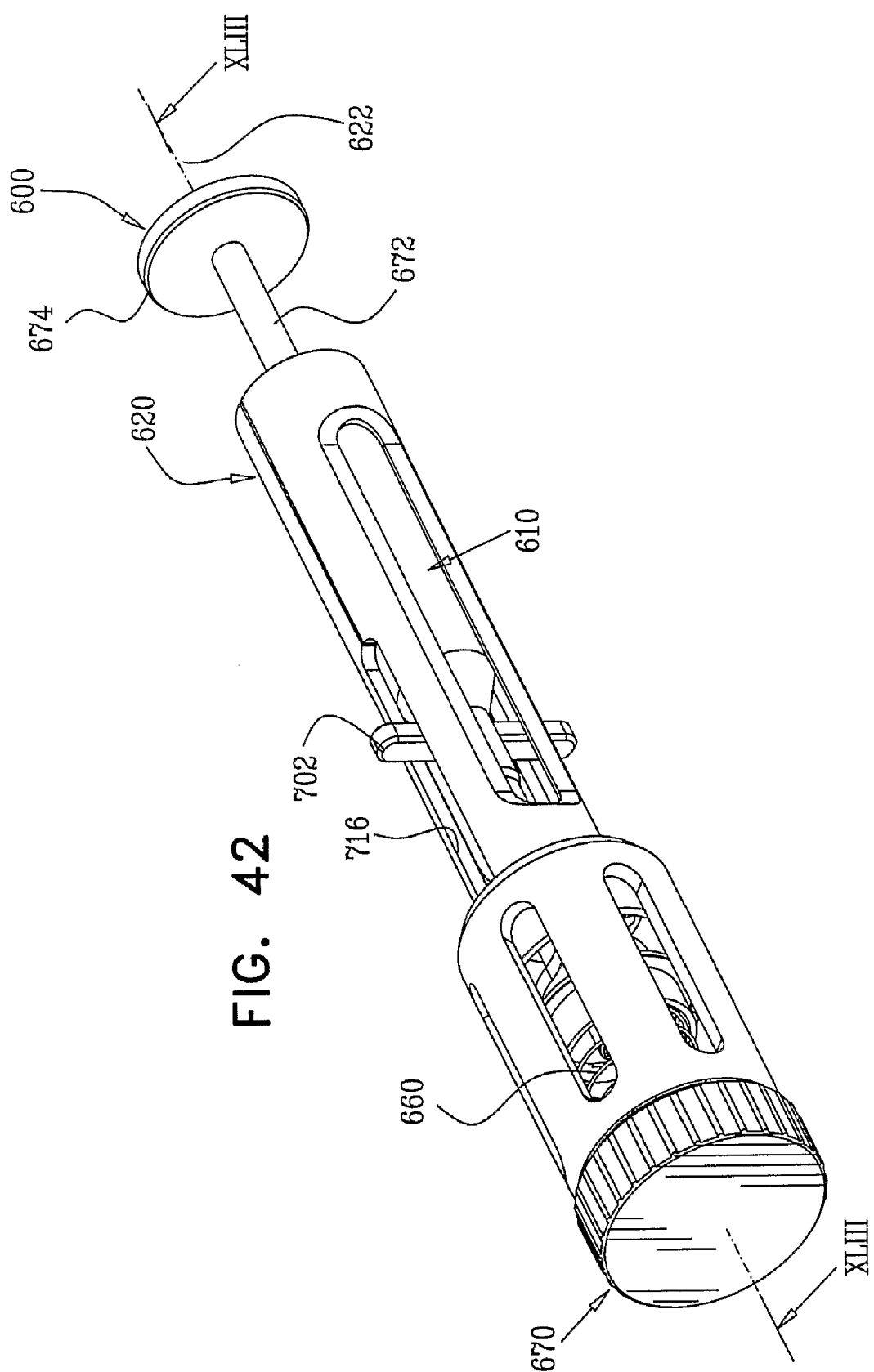
FIG. 42 is a simplified pictorial illustration of the injection assembly of FIGS. 40 and 41 in a partial syringe retraction orientation.
Figure 43:
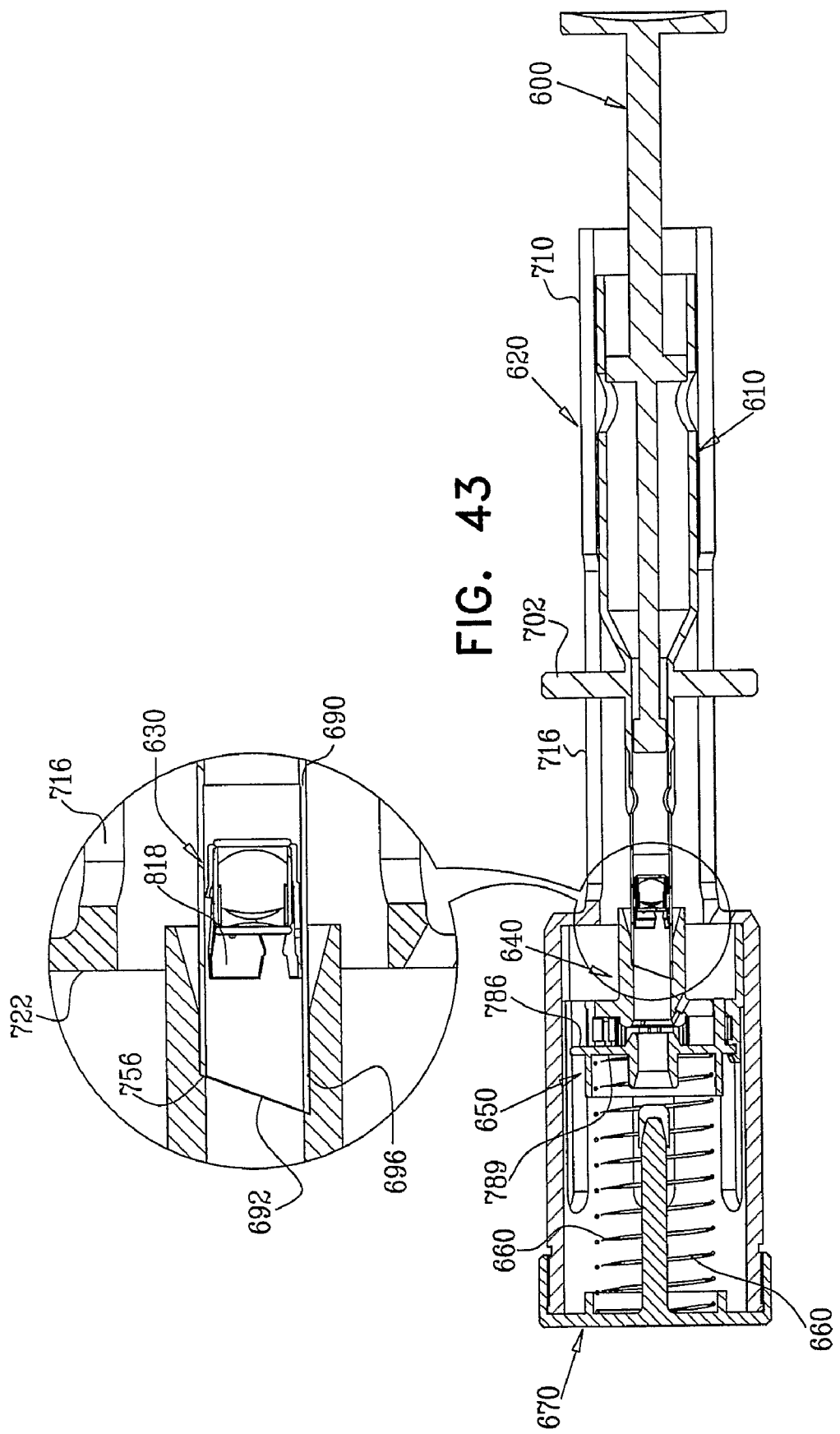
FIG. 43 is a simplified sectional illustration of the injection assembly of FIG. 42, taken along section lines XLIII-XLIII in FIG. 42.

Reference is now made to FIGS. 42 and 43, which are simplified pictorial and sectional illustrations of the injection assembly of FIGS. 40 and 41 in a partial syringe retraction orientation. The injection assembly in its intraocular implant loading orientation, as seen in FIGS. 40 and 41, is brought to the partial syringe retraction orientation of FIGS. 42 and 43 by the user releasing finger engagement protrusions 702 of syringe 610. Upon release of the finger engagement protrusions 702, the syringe 610, together with plunger 600, and rearward and forward positioning elements 640 and 650 are rearwardly displaced along axis 622 with respect to housing element 620 by compression spring 660, which preferably returns to a fully relaxed orientation.

Engagement of compression spring 660 with forward facing surface 789 of ring shaped portion 786 of forward positioning element 650, produces rearward displacement thereof with respect to housing element 620, and rearwardly displaces rearward positioning element 640. Preferably, forward and rearward positioning elements 650 and 640 return to their respective storage orientation positions shown in FIGS. 36 and 37. Due to the engagement between angled shoulder 756 of rearward positioning element 640 and sharpened and angled forward edge 692 of syringe 610, rearward displacement of rearward positioning element 640 results in rearward displacement of syringe 610, together with plunger 600 and intraocular implant 630 which is located at the interior of forward part 696 of forward portion 690 of syringe 610.

Reference is now made to FIGS. 44 and 45, which are simplified pictorial and sectional illustrations of the injection assembly of FIGS. 42 and 43 in a full syringe retraction orientation. The injection assembly in its partial syringe retraction orientation, as seen in FIGS. 42 and 43, is brought to the full syringe retraction orientation of FIGS. 44 and 45 by the user pushing finger engagement protrusions 702 of syringe 610 rearwardly along axis 622 with respect to housing element 620, thereby disengaging sharpened and angled forward edge 692 of syringe 610 from angled shoulder 756 of rearward positioning element 640.

In the orientation shown in FIGS. 44 and 45, finger engagement protrusions 702 of syringe 610 are fully retracted and thus lie against a rearward edge of side slots 716.

At this stage, the user typically continues to push finger engagement protrusions 702, thereby spreading apart bifurcated parts of cylindrical portion 710 of housing 620 along lines 718, and removes therefrom the syringe 610, which accommodates the plunger 600 and the intraocular implant 630.

Reference is now made to FIGS. 46 and 47, which are simplified pictorial and sectional illustrations of the syringe of FIGS. 21A and 21B in a ready to use orientation. As seen in FIGS. 46 and 47, the intraocular implant 630 remains within the interior of the forward part 696 of forward portion 690 of syringe 610. A forward surface 912 of second plunger portion 680 engages a rear surface of capsule 810.

Figure 48A:
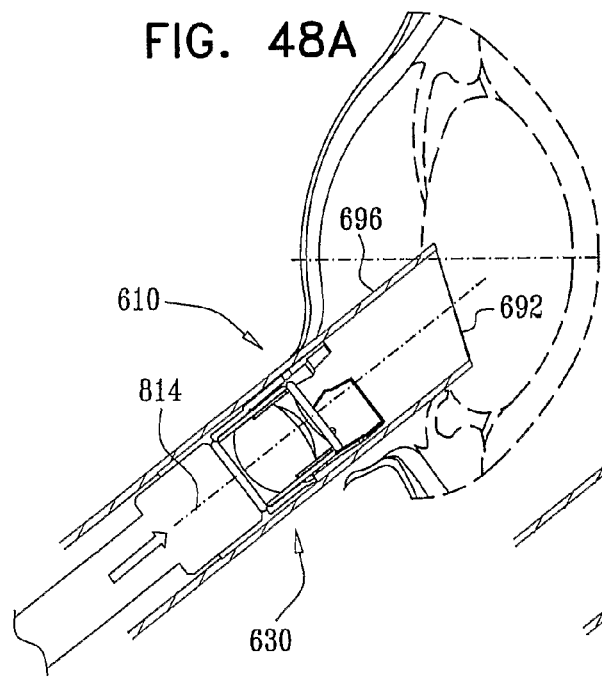
FIGS. 48A, 48B, 48C and 48D are simplified sectional illustrations of four stages of injection of the injectable intraocular implant of FIGS. 32A, 32B and 33 into the eye of a patient.

Reference is now made to FIGS. 48A, 48B, 48C and 48D, which are simplified sectional illustrations of four stages of the injection of the intraocular implant 630 located within forward part 696 of syringe 610 into the eye of a patient. FIG. 48A shows initial insertion of the sharpened and angled edge 692 of syringe 610 into the lens capsule of the eye.

Figure 48B:
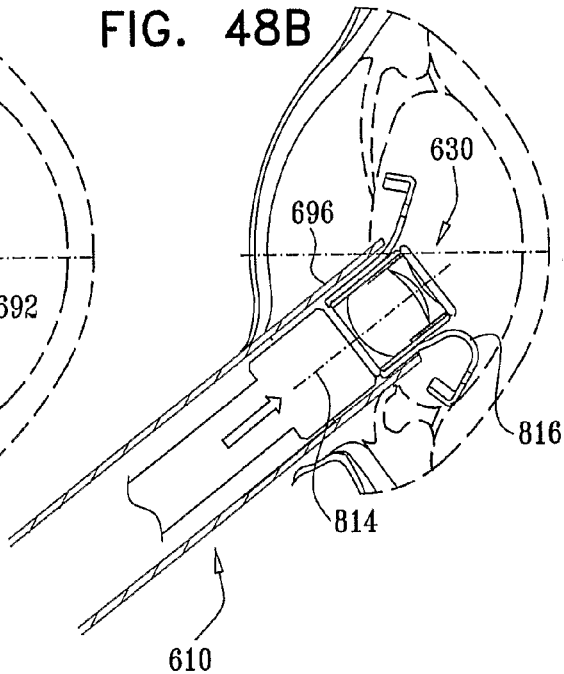
Figure 48C:
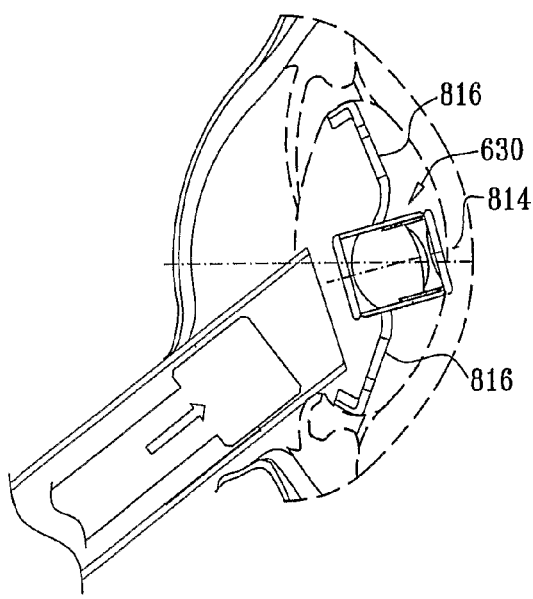
Figure 48D:
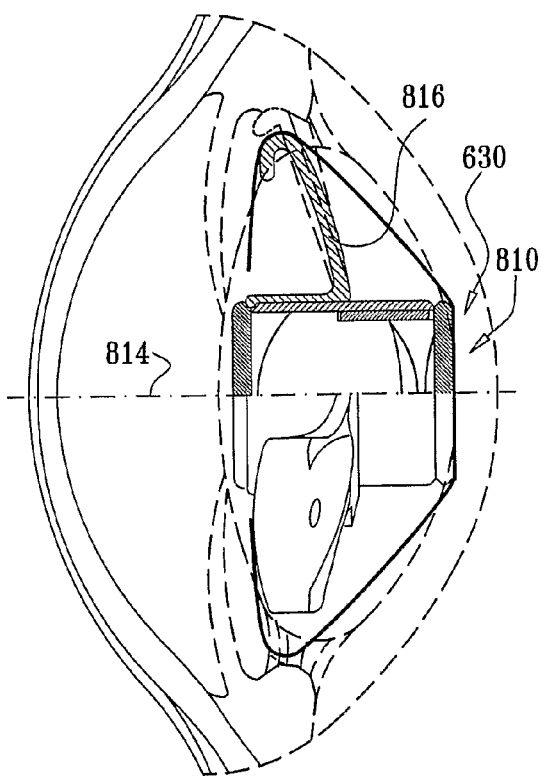

FIG. 48B shows the implant being forced out of syringe 610 into the lens capsule, such that one of haptics 816, which is located adjacent the shorter side of angled and sharpened edge 692 of syringe 610, unfolds inside the lens capsule. FIG. 48C shows unfolding of a second one of haptics 816 inside the lens capsule and FIG. 48D shows proper orientation of the implant, including fully deployed haptics 816, within the lens capsule.

As seen with particular clarity in FIGS. 48A-48C, the plunger 600 pushes the intraocular implant 630 along the axis 814 thereof.

It is a particular feature of the present invention that the haptics 816 are configured and arranged with respect to the lens capsule so as to urge the capsule 810 rearwardly away from the cornea in order to minimize, insofar as possible, engagement between the intraocular implant 630 and the endothelium.

It will be appreciated by persons skilled in the art that the present invention is not limited to what has been particularly shown and described hereinabove. Rather the scope of the present invention includes both combinations and subcombinations of features described hereinabove as well as variations and modifications thereof which would occur to a person skilled in the art upon reading the foregoing description, taken together with the drawings, and which are not in the prior art.

The invention claimed is:

1. An intraocular implant injection assembly comprising:
   a housing arranged along a longitudinal axis, said housing including a forward portion and a rearward portion;
   a syringe, positionable along said longitudinal axis in said rearward portion of said housing;
   an intraocular implant positioning subassembly, positioned along said longitudinal axis in said forward portion of said housing;
   an intraocular implant mounted in said intraocular implant positioning subassembly; and
   an intraocular implant displacer operative to displace said intraocular implant rearwardly along said longitudinal axis relative to said positioning subassembly into said syringe when said positioning subassembly is forwardly displaced relative to said housing by said syringe in response to a user displacing said syringe forwardly within said housing.

2. An intraocular implant injection assembly according to claim 1 and wherein said
   syringe comprises a user-sensible azimuthal orientation indicator.

3. An intraocular implant injection assembly according to claim 1, and wherein said intraocular implant positioning subassembly comprises:
   a rearward positioning element including an azimuthal registration aperture; and
   a forward positioning element including an azimuthal registration pin operative to engage said azimuthal registration aperture and to prevent relative rotation between said rearward positioning element and said forward positioning element.

4. An intraocular implant injection assembly according to claim 3 and wherein:
   said intraocular implant includes haptics; and
   a slanted portion of said haptics lies between a forward, inwardly facing, tapered portion of said rearward positioning element and a rearward, outwardly facing, tapered portion of said forward positioning element.

5. An intraocular implant injection assembly according to claim 4 and wherein said tapered portion of said rearward positioning element and said tapered portion of said forward positioning element are configured to guide said haptics while said intraocular implant is loaded into said syringe, thereby maintaining mechanical integrity of said haptics.

6. An intraocular implant injection assembly according to claim 1 and wherein said intraocular implant positioning subassembly includes a plurality of intraocular implant positioning protrusions operative to retain said intraocular implant.

7. An intraocular implant injection assembly according to claim 1 and wherein said intraocular implant positioning subassembly includes an angled shoulder having an angular orientation which is generally identical to that of a forward angled edge of said syringe and which is adapted to engage said forward angled edge.

8. An intraocular implant injection assembly according to claim 1, wherein:
   said intraocular implant includes haptics; and
   a forward angled edge of said syringe is configured to allow said haptics to unfold sequentially as said intraocular implant is injected into an eye.

9. An intraocular implant injection assembly according to claim 1, wherein:
   said intraocular implant includes haptics and a capsular body portion; and
   said haptics are adapted to urge said capsular body portion away from the cornea when said intraocular implant is implanted in the eye.

10. A system for injecting an intraocular implant into an eye, comprising:
    an intraocular implant including haptics and having an optical axis;
    an injector having an injector axis, adapted to have said intraocular implant arranged therein such that said optical axis is parallel to said injector axis; and
    an intraocular implant displacer operative to inject said intraocular implant into the eye by displacing said intraocular implant along an injection axis which is coaxial with said optical axis.

11. A system according to claim 10 and wherein said injector axis is adapted to have said intraocular implant arranged in said injector such that said injector axis is coaxial with said optical axis.

12. A system for injecting an intraocular implant into an eye according to claim 10 and also comprising an intraocular implant positioning subassembly operative to arrange said intraocular implant in said injector, said intraocular implant positioning subassembly comprising an intraocular implant positioning displacer including a shaft portion operative to push said intraocular implant from said positioning subassembly into said injector.

13. A system for injecting an intraocular implant into an eye according to claim 12 and wherein:
    said intraocular implant positioning displacer moves said intraocular implant in a first direction along said injection axis;
    said intraocular implant displacer moves said intraocular implant in a second direction along said injection axis; and
    said first direction being opposite said second direction.

14. An intraocular implant injection assembly according to claim 1, wherein:
    said intraocular implant includes haptics and a capsular body portion; and
    said housing, said syringe and said positioning subassembly are positioned relative to each other such that said displacer is operative to position said intraocular implant in said syringe such that said haptics are folded over said capsular body portion and extend forwardly thereof.

15. An intraocular implant injection assembly according to claim 1 and wherein said rearward portion of said housing comprises a partially bifurcated rear portion.

16. An intraocular implant injection assembly according to claim 1 and wherein said syringe is removable from said housing.

17. An intraocular implant injection assembly according to claim 1 and also comprising a plunger operative to displace said intraocular implant forwardly relative to said syringe.

18. An intraocular implant injection assembly according to claim 1 and wherein:
    said intraocular implant includes haptics and a capsular body portion;
    said syringe includes an angled forward edge; and
    said housing, said syringe and said positioning subassembly are positioned relative to each other such that said displacer is operative to position said intraocular implant in said syringe such that one of said haptics is located adjacent to a shorter side of said syringe at said forward edge.

* * * * *